US008298549B2

(12) United States Patent
Balint et al.

(10) Patent No.: US 8,298,549 B2
(45) Date of Patent: Oct. 30, 2012

(54) SEQUENTIAL ADMINISTRATION OF A REPLICATION DEFECTIVE ADENOVIRUS VECTOR IN VACCINATION PROTOCOLS

(75) Inventors: Joseph P. Balint, Seattle, WA (US); Frank R. Jones, Ellensburg, WA (US); Richard B. Gayle, III, Woodinville, WA (US)

(73) Assignee: Etubics Corporation, Seattle, WA (US)

( * ) Notice: Subject to any disclaimer, the term of this patent is extended or adjusted under 35 U.S.C. 154(b) by 51 days.

(21) Appl. No.: 12/651,836

(22) Filed: Jan. 4, 2010

(65) Prior Publication Data

US 2010/0183673 A1      Jul. 22, 2010

Related U.S. Application Data

(63) Continuation-in-part of application No. PCT/US2008/068924, filed on Jul. 1, 2008.

(60) Provisional application No. 60/947,601, filed on Jul. 2, 2007.

(51) Int. Cl.
*A61K 39/235* (2006.01)
*C12N 15/861* (2006.01)

(52) U.S. Cl. ............... 424/233.1; 424/205.1; 435/320.1

(58) Field of Classification Search .................. None
See application file for complete search history.

(56) References Cited

U.S. PATENT DOCUMENTS

| | | | |
|---|---|---|---|
| 6,057,158 A | 5/2000 | Chamberlain et al. | |
| 6,063,622 A | 5/2000 | Chamberlain et al. | |
| 6,083,750 A * | 7/2000 | Chamberlain et al. | 435/369 |
| 6,451,596 B1 | 9/2002 | Chamberlain et al. | |
| 7,786,278 B2 | 8/2010 | Parrington et al. | |
| 2004/0265274 A1 | 12/2004 | Wei et al. | |
| 2006/0222665 A1 | 10/2006 | Schreiber | |
| 2007/0042002 A1 | 2/2007 | Weeks-Levy et al. | |

FOREIGN PATENT DOCUMENTS

| | | |
|---|---|---|
| WO | WO 98/58956 A2 | 12/1998 |
| WO | WO 98/58956 A3 | 3/1999 |
| WO | WO 2006/033672 A2 | 3/2006 |
| WO | WO 2006/033672 A3 | 6/2006 |

OTHER PUBLICATIONS

Akiyama, et al. The transforming potential of the c-erbB-2 protein is regulated by its autophosphorylation at the carboxyl-terminal domain. Mol Cell Biol. Feb. 1991;11(2):833-42.
Amalfitano, et al. Improved adenovirus packaging cell lines to support the growth of replication-defective gene-delivery vectors. Proc Natl Acad Sci U S A 93:3352-6. (1996).
Amalfitano, et al. Isolation and characterization of packaging cell lines that coexpress the adenovirus E1, DNA polymerase, and preterminal proteins: implications for gene therapy. Gene Ther 4:258-63. (1997).
Amalfitano, et al. Production and characterization of improved adenovirus vectors with the E1, E2b, and E3 genes deleted. J Virol 72;926-33 (1998).
Amalfitano, et al. Separating fact from fiction: assessing the potential of modified adenovirus vectors for use in human gene therapy. Curr Gene Ther 2:111-133 (2002).
Amalfitano, et al. Systemic correction of the muscle disorder glycogen storage disease type II after hepatic targeting of a modified adenovirus vector encoding human acid-alpha-glucosidase. Proc Natl Acad Sci U S A 96;8861-6 (1999).
Amalfitano. Use of multiply deleted adenovirus vectors to probe adenovirus vector performance and toxicities: Curr Opin Mol Ther. 5:362-366 (2003).
Amara, et al. A new generation of HIV vaccines. Trends Mol Med 8;489-95 (2002).
Amara, et al. Different patterns of immune responses but similar control of a simian-human immunodeficiency virus 89.6P mucosal challenge by modified vaccinia virus Ankara (MVA) and DNA/MVA vaccines. J Virol 76;7625-31 (2002b).
Andre, et al. Increased immune response elicited by DNA vaccination with a synthetic gp120 sequence with optimized codon usage. J Virol. 72:1497-503 (1998).
Ashkar, et al. Local delivery of CpG oligodeoxynucleotides induces rapid changes in the genital mucosa and inhibits replication, but not entry, of herpes simplex virus type 2. J Virol 77;8948-56 (2003).
Badaro, et al. Successful use of a defined antigen/GM-CSF adjuvant vaccine to treat mucosal leishmaniasis refractory to antimony: a case report. Braz J Infect Dis 5, 223-232 (2001).
Badaro, et al. Immunotherapy for drug-refractory mucosal leishmaniasis. J Infect Dis 194:8 1151-59 (2006).
Balachandran, et al. Protection against lethal challenge of BALB/c mice by passive transfer of monoclonal antibodies to five glycoproteins of herpes simplex virus type 2. Infect Immun 37;1132-7. (1982).
Bangari, et al. Current strategies and future directions for eluding adenoviral vector immunity. Curr Gene Ther. Apr. 2006; 6(2):215-226.
Barjot, et al. Gutted adenoviral vector growth using E1/E2b/E3-deleted helper viruses. J Gene Med 4;480-9 (2002).
Barouch, et al. Adenovirus vector-based vaccines for human immunodeficiency virus type 1. Hum Gene Ther. 16:149-156 (2005).
Barouch, et al. Augmentation of immune responses to HIV-1 and simian immunodeficiency virus DNA vaccines by IL-2/Ig plasmid administration in rhesus monkeys. PNAS, 2000. 97(8): p. 4192-7.
Barouch, et al. Control of viremia and prevention of clinical AIDS in rhesus monkeys by cytokine-augmented DNA vaccination. Science 290;486-92 (2000).

(Continued)

*Primary Examiner* — Robert A Zeman
(74) *Attorney, Agent, or Firm* — Wilson Sonsini Goodrich & Rosati

(57) ABSTRACT

Methods for generating immune responses using adenovirus vectors that allow multiple vaccinations with the same adenovirus vector and vaccinations in individuals with preexisting immunity to adenovirus are provided.

26 Claims, 14 Drawing Sheets

OTHER PUBLICATIONS

Barouch, et al. Eventual AIDS vaccine failure in a rhesus monkey by viral escape from cytotoxic T lymphocytes. Nature 415;335-9 (2002).
Barouch, et al. Plasmid chemokines and colony-stimulating factors enhance the immunogenicity of DNA priming-viral vector boosting human immunodeficiency virus type 1 vaccines. J Virol 77;8729-35 (2003).
Barouch, et al. Reduction of simian-human immunodeficiency virus 89.6P viremia in rhesus monkeys by recombinant modified vaccinia virus Ankara vaccination. J Virol 75;5151-8 (2001).
Barratt-Boyes, et al. Broad cellular immunity with robust memory responses to simian immunodeficiency virus following serial vaccination with adenovirus 5- and 35-based vectors. J Gen Virol 87:.Pt 1 139-149 (2006).
Belkaid, et al. CD8+ T cells are required for primary immunity in C57BL/6 mice following low-dose, intradermal challenge with Leishmania major. J Immunol 168(8):3992-4000 (2002).
Betts, et al. HIV nonprogressors preferentially maintain highly functional HIV-specific CD8+ T-cells. Blood, 2006; 107(12):4781-4789.
Borges, et al. Potent Stimulation of the Innate Immune System by a Leishmania brasiliensis Recombinant Protein. Infect Immun 69, 5270-5277 (2001).
Borrow, et al. Virus-specific CD8+ cytotoxic T-lymphocyte activity associated with control of viremia in primary human immunodeficiency virus type 1 infection. J Virol 68;6103-10 (1994).
Brave, et al. Vaccine delivery methods using viral vectors. Mol Pharm 4:.1 18-32 (2007).
Campos-Neto, et al. Protection against cutaneous leishmaniasis induced by recombinant antigens in murine and nonhuman primate models of the human disease. Infect Immun 69, 4103-4108 (2001).
Campos-Neto, et al. Vaccination with plasmid DNA encoding TSA/LmSTI1 leishmanial fusion proteins confers protection against Leishmania major infection in susceptible BALB/c mice. Infect Immun 70:2828-36 (2002).
Caravokyri, et al. Constitutive episomal expression of polypeptide IX (pIX) in a 293-based cell line complements the deficiency of pIX mutant adenovirus type 5. J Virol. Nov. 1995;69(11):6627-33.
Casimiro, et al. Comparative immunogenicity in rhesus monkeys of DNA plasmid, recombinant vaccinia virus, and replication-defective adenovirus vectors expressing a human immunodeficiency virus type 1 Gag gene. J Virol 77;6305-13 (2003).
Chamberlain, et al. Deletion screening of the Duchenne muscular dystrophy locus via multiplex DNA amplification. Nucleic Acids Res 16;11141-56 (1988).
Chamberlain, et al. Packaging cell lines for generating replication-defective and gutted adenoviral vectors. Methods Mol Med 76;153-66 (2003).
Chartier, et al. Efficient generation of recombinant adenovirus vectors by homologous recombination in Escherichia coli. J Virol 70;4805-10 (1996).
Chen et al, Dissecting the multifactorial causes of immunodominance in class I-restricted T cell responses to viruses. Immunity, 2000. 12(1): p. 83-93.
Chirmule, et al. Immune responses to adenovirus and adeno-associated virus in humans. Gene Ther. 1999; 6:1574-83.
Chun, et al. Distribution fate and mechanism of immune modulation following mucosal delivery of plasmid DNA encoding IL-10. J Immunol 163;2393-402 (1999).
Cohen. Prevention cocktails: combining tools to prevents HIV's spread. Science. 309:1002-1005 (2005).
Coler, et al. Immunization with a polyprotein vaccine consisting of the T-Cell antigens thiol-specific antioxidant, Leishmania major stress-inducible protein 1, and Leishmania elongation initiation factor protects against leishmaniasis. Infect Immun 70:4215-25 (2002).
Coler, et al. Second-generation vaccines against leishmaniasis. Trends Parasitol 21:244-9 (2005).
Corey, et al. Recombinant glycoprotein vaccine for the prevention of genital HSV-2 infection: two randomized controlled trials. Chiron HSV Vaccine Study Group. JAMA 282;331-40. (1999).
Corey, et al. TRPA1 is a candidate for the mechanosensitive transduction channel of vertebrate hair cells. Nature. 432:723-730 (2004).
Dellorusso, et al. Functional correction of adult mdx mouse muscle using gutted adenoviral vectors expressing full-length dystrophin. Proc Natl Acad Sci U S A 99;12979-84 (2002).
Ding, et al. Efficacy of gene therapy for a prototypical lysosomal storage disease (GSD-II) is critically dependent on vector dose, transgene promoter, and the tissues targeted for vector transduction. Mol Ther 5;436-46 (2002).
Ding, et al. Long-term efficacy after [E1-, polymerase-] adenovirus-mediated transfer of human acid-alpha-glucosidase gene into glycogen storage disease type II knockout mice. Hum Gene Ther 12;955-65 (2001).
Dix, et al. Use of monoclonal antibody directed against herpes simplex virus glycoproteins to protect mice against acute virus-induced neurological disease. Infect Immun 34;192-9. (1981).
Eo, et al. Prime-boost immunization with DNA vaccine: mucosal route of administration changes the rules. J Immunol 166;5473-9 (2001).
Epstein, et al. Protection against multiple influenza A subtypes by vaccination with highly conserved nucleoprotein. Vaccine, 2005. 23(46-47): p. 5404-10.
Ertl, et al. Novel vaccine approaches. J Immunol. 156:3579-3582 (1996).
Evans, et al. Development of stable liquid formulations for adenovirus-based vaccines. J Pharm Sci 93:2458-475 (2004).
Everett, et al. Liver toxicities typically induced by first-generation adenoviral vectors can be reduced by use of E1, E2b-deleted adenoviral vectors. Hum Gene Ther, 2003. 14(18): p. 1715-26.
Fleming, et al. Herpes simplex virus type 2 in the United States, 1976 to 1994. N Engl J Med 337;1105-11. (1997).
Gabaglia, et al. A single intramuscular injection with an adenovirus-expressing IL-12 protects BALB/c mice against Leishmania major infection, while treatment with an IL-4-expressing vector increases disease susceptibility in B10.D2 mice.J Immunol 162:.2 753-760 (1999).
Gallichan, et al. Long-lived cytotoxic T lymphocyte memory in mucosal tissues after mucosal but not systemic immunization. J Exp Med 184;1879-90 (1996).
Gallichan, et al. Long-term immunity and protection against herpes simplex virus type 2 in the murine female genital tract after mucosal but not systemic immunization. J Infect Dis 177;1155-61 (1998).
Gallichan, et al. Mucosal immunity and protection after intranasal immunization with recombinant adenovirus expressing herpes simplex virus glycoprotein B. J Infect Dis 168;622-9. (1993).
Gallichan, et al. Mucosal immunization with a recombinant adenovirus vector induces local and systemic immunity and protection from herpes simplex virus. Adv Exp Med Biol, 1995. 371B: p. 1581-5.
Gao et al. Protection of mice and poultry from lethal H5N1 avian influenza virus through adenovirus-based immunization. J Virol, 2006. 80(4): p. 1959-64.
Gomez-Roman, et al. Adenoviruses as vectors for HIV vaccines. AIDS Rev 5;178-85 (2003).
Gorziglia, et al. Elimination of both E1 and E2 from adenovirus vectors further improves prospects for in vivo human gene therapy. J Virol. Jun. 1996;70(6):4173-8.
Greene, et al. Envelope glycoprotein mutations mediate equine amplification and virulence of epizootic venezuelan equine encephalitis virus. J Virol 79:9128-33. (2005).
Haglund, et al. Robust recall and long-term memory T-cell responses induced by prime-boost regimens with heterologous live viral vectors expressing human immunodeficiency virus type 1 Gag and Env proteins. J Virol 76;7506-17 (2002).
Handman. Leishmaniasis: current status of vaccine development. Clin Microbiol Rev 14:.2 229-243 (2001).
Hanke, et al. Effective induction of simian immunodeficiency virus-specific cytotoxic T lymphocytes in macaques by using a multiepitope gene and DNA prime-modified vaccinia virus Ankara boost vaccination regimen. J Virol 73;7524-32. (1999).
Harandi, et al. A protective role of locally administered immunostimulatory CpG oligodeoxynucleotide in a mouse model of genital herpes infection. J Virol 77;953-62 (2003).
Harindranath, et al. Structure of the VH and VL segments of polyreactive and monoreactive human natural antibodies to HIV-1 and *Escherichia coli* ?-galactosidase. International Immunology. Dec. 1993; 5(12): 1523-1533. Abstract only.

Harris, et al. Acute regression of advanced and retardation of early aortic atheroma in immunocompetent apolipoprotein-E (apoE) deficient mice by administration of a second generation [E1(-), E3(-), polymerase(-)] adenovirus vector expressing human apoE. Hum Mol Genet 11;43-58 (2002).

Hartigan-O'Connor, et al. Developments in gene therapy for muscular dystrophy. Microsc Res Tech 48;223-38 (2000).

Hartigan-O'Connor, et al. Efficient rescue of gutted adenovirus genomes allows rapid production of concentrated stocks without negative selection. Hum Gene Ther 13;519-31. (2002b).

Hartigan-O'Connor, et al. Generation and growth of gutted adenoviral vectors. Methods Enzymol 346;224-46 (2002).

Hartigan-O'Connor, et al. Immune evasion by muscle-specific gene expression in dystrophic muscle. Mol Ther 4;525-33 (2001).

Hartigan-O'Connor, et al. Improved production of gutted adenovirus in cells expressing adenovirus preterminal protein and DNA polymerase. J Virol 73;7835-7841 (1999a).

Hartman, et al. Adenoviral infection induces a multi-faceted innate cellular immune response that is mediated by the toll-like receptor pathway in A549 cells. Virology. Feb. 20, 2007;358(2):357-72. Epub Oct. 5, 2006.

Hartman, et al. Adenovirus infection triggers a rapid, MyD88-regulated transcriptome response critical to acute-phase and adaptive immune responses in vivo. J Virol. Feb. 2007;81(4):1796-812. Epub Nov. 22, 2006.

Harui, et al. Vaccination with helper-dependent adenovirus enhances the generation of transgene-specific CTL. Gene Ther. 11:1617-26 (2004).

Hauser, et al. Analysis of muscle creatine kinase regulatory elements in recombinant adenoviral vectors. Mol Ther 2;16-25 (2000).

Hauser, et al. Improved adenoviral vectors for gene therapy of Duchenne muscular dystrophy. Neuromuscul Disord 7;277-83 (1997).

Hodges, et al. Adenovirus vectors with the 100K gene deleted and their potential for multiple gene therapy applications. J Virol. Jul. 2001;75(13):5913-20.

Hodges, et al. Multiply deleted [E1, polymerase-, and pTP-] adenovirus vector persists despite deletion of the preterminal protein. J Gene Med 2;250-9 (2000).

Hoelscher, et al. Development of adenoviral-vector-based pandemic influenza vaccine against antigenically distinct human H5N1 strains in mice. Lancet, 2006. 367(9509): p. 475-81.

Hu, et al. Persistence of an [E1-, polymerase-] adenovirus vector despite transduction of a neoantigen into immune-competent mice. Hum Gene Ther 10;355-64 (1999).

Huang, et al. Human immunodeficiency virus type 1-specific immunity after genetic immunization is enhanced by modification of Gag and Pol expression. J Virol. 75:4947-51 (2001).

Imler. Adenovirus vectors as recombinant viral vaccines. Vaccine. 13:1143-1151 (1995).

International search report and written opinion dated Dec. 29, 2008 for PCT/US2008/068924.

Jin, et al. Dramatic rise in plasma viremia after CD8(+) T cell depletion in simian immunodeficiency virus-infected macaques. J Exp Med 189;991-8 (1999).

Jooss, et al. Transduction of dendritic cells by DNA viral vectors directs the immune response to transgene products in muscle fibers. J Virol 72;4212-23 (1998).

Kafri, et al. Cellular immune response to adenoviral vector infected cells does not require de novo viral gene expression: implications for gene therapy. Proc Natl Acad Sci U S A 95;11377-82 (1998).

Karem, et al. Protective immunity against herpes simplex virus (HSV) type 1 following oral administration of recombinant *Salmonella typhimurium* vaccine strains expressing HSV antigens. J Gen Virol 78 ( Pt 2);427-34 (1997).

Kemp, et al. Dichotomy of the human T cell response to *Leishmania* antigens. I. Th1-like response to *Leishmania* major promastigote antigens in individuals recovered from cutaneous leishmaniasis. Clin Exp Immunol 96:.3 410-15 (1994).

Khanam, et al. An adenovirus prime/plasmid boost strategy for induction of equipotent immune responses to two dengue virus serotypes. BMC Biotechnol 7:.1-11 (2007).

Kiang, et al. Fully deleted Ad persistently expressing GAA accomplishes long-term skeletal muscle glycogen correction in tolerant and nontolerant GSD-II mice. Mol Ther, 2006. 13(1):127.

Kiang, et al. Multiple innate inflammatory responses induced after systemic adenovirus vector delivery depend on a functional complement system. Mol Ther. Oct. 2006;14(4):588-98. Epub Jun. 2, 2006.

Kinney, et al. Nucleotide sequences of the 26S mRNAs of the viruses defining the Venezuelan equine encephalitis antigenic complex. Am J Trop Med Hyg 59:952-64. (1998).

Kirk, et al. Gene-modified dendritic cells for use in tumor vaccines. Hum Gene Ther 11;797-806 (2000).

Kirk, et al. T cell-dependent antitumor immunity mediated by secondary lymphoid tissue chemokine: augmentation of dendritic cell-based immunotherapy. Cancer Res 61;2062-70 (2001b).

Kirk, et al. The dynamics of the T-cell antitumor response: chemokine-secreting dendritic cells can prime tumor-reactive T cells extranodally. Cancer Res 61;8794-802 (2001a).

Kong, et al. Immunogenicity of multiple gene and Glade human immunodeficiency virus type 1 DNA vaccines. J Virol. 77:12764-72 (2003).

Koup, et al. Temporal association of cellular immune responses with the initial control of viremia in primary human immunodeficiency virus type 1 syndrome. J Virol 68;4650-5 (1994).

Kuklin, et al. Role of mucosal immunity in herpes simplex virus infection. J Immunol 160;5998-6003 (1998).

Kumar-Singh, et al. Encapsidated adenovirus minichromosomes allow delivery and expression of a 14 kb dystrophin cDNA to muscle cells. Hum Mol Genet 5;913-21 (1996).

Lemiale, et al. Enhanced mucosal immunoglobulin A response of intranasal adenoviral vector human immunodeficiency virus vaccine and localization in the central nervous system. J Virol 77;10078-87 (2003).

Letvin, et al. Heterologous envelope immunogens contribute to AIDS vaccine protection in rhesus monkeys. J Virol. 78;7490-7 (2004).

Logan, et al. Adenovirus tripartite leader sequence enhances translation of mRNAs late after infection. Proc Natl Acad Sci U S A. Jun. 1984;81(12):3655-9.

Lozier, et al. Toxicity of a first-generation adenoviral vector in rhesus macaques. Hum Gene Ther 13;113-24 (2002).

Lubaroff, et al. Clinical protocol: phase I study of an adenovirus/prostate-specific antigen vaccine in men with metastatic prostate cancer. Hum Gene Ther. 17:220-229 (2006).

Luebke, et al. A modified adenovirus can transfect cochlear hair cells in vivo without compromising cochlear function. Gene Ther. 8:789-794 (2001).

Maione, et al. An improved helper-dependent adenoviral vector allows persistent gene expression after intramuscular delivery and overcomes preexisting immunity to adenovirus. Proc Natl Acad Sci U S A. May 22, 2001;98(11):5986-91. Epub May 15, 2001.

Manickan, et al. Vaccination with recombinant vaccinia viruses expressing ICP27 induces protective immunity against herpes simplex virus through CD4+ Th1+ T cells. J Virol 69;4711-6 (1995a).

Mata, et al. The MHC class I-restricted immune response to HIV-Gag in BALB/c mice selects a single epitope that does not have a predictable MHC-binding motif and binds to Kd through interactions between a glutamine at P3 and pocket D. J Immunol 161;2985-93 (1998).

McCoy, et al. Effect of preexisting immunity to adenovirus human serotype 5 antigens on the immune responses of nonhuman primates to vaccine regimens based on human- or chimpanzee-derived adenovirus vectors. J Virol 81:6594-6604 (2007).

McDermott, et al. Cytotoxic T-Lymphocyte Escape Does Not Always Explain the Transient Control of Simian Immunodeficiency Virus SIVmac239 Viremia in Adenovirus-Boosted and DNAna-Primed Mamu-A*01-Positive Rhesus Macaques. J Virol. 79:15556-66 (2005).

McDermott, et al. Immunity in the female genital tract after intravaginal vaccination of mice with an attenuated strain of herpes simplex virus type 2. J Virol 51;747-53 (1984).

McDermott, et al. Protection of mice against lethal challenge with herpes simplex virus by vaccination with an adenovirus vector expressing HSV glycoprotein B. Virology 169;244-7. (1989b).

Milligan, et al. T lymphocytes are required for protection of the vaginal mucosae and sensory ganglia of immune mice against reinfection with herpes simplex virus type 2 J Immunol 160;6093-100 (1998).

Mitani, et al. Rescue, propagation, and partial purification of a helper virus-dependent adenovirus vector. Proc Natl Acad Sci U S A. Apr. 25, 1995;92(9):3854-8.

Mole, et al. The impact of active herpes simplex virus infection on human immunodeficiency virus load. J Infect Dis 176;766-70 (1997).

Moog, et al. Autologous and heterologous neutralizing antibody responses following initial seroconversion in human immunodeficiency virus type 1-infected individuals. J Virol 71;3734-41 (1997).

Moore, et al. Effects of antigen and genetic adjuvants on immune responses to human immunodeficiency virus DNA vaccines in mice. J Virol 76;243-50 (2002).

Moorhead, et al. A replication-incompetent adenovirus vector with the preterminal protein gene deleted efficiently transduces mouse ears. J Virol. 73:1046-53 (1999).

Morse, et al. Synergism from combined immunologic and pharmacologic inhibition of HER2 in vivo. Int J Cancer: Jun. 15, 2010;126(12):2893-903.

Morsy, et al. An adenoviral vector deleted for all viral coding sequences results in enhanced safety and extended expression of a leptin transgene. Proc Natl Acad Sci U S A 95;7866-71 (1998).

Najera, et al. Pol gene quasispecies of human immunodeficiency virus: mutations associated with drug resistance in virus from patients undergoing no drug therapy. J Virol 69;23-31 (1995).

Nazir, et al. Innate immune response to adenovirus. J Investig Med. 53:292-304 (2005).

Nemunaitis, et al. Pilot trial of intravenous infusion of a replication-selective adenovirus (ONYX-015) in combination with chemotherapy or IL-2 treatment in refractory cancer patients. Cancer Gene Ther. 10:341-352 (2003).

Openshaw, et al. Immune responses and disease enhancement during respiratory syncytial virus infection. Clin Microbiol Rev, 2005. 18(3): p. 541-55.

Parr, et al. Immunoglobulin G is the main protective antibody in mouse vaginal secretions after vaginal immunization with attenuated herpes simplex virus type 2. J Virol 71;8109-15. (1997).

Parr, et al. Mucosal immunity to herpes simplex virus type 2 infection in the mouse vagina is impaired by in vivo depletion of T lymphocytes. J Virol 72;2677-85 (1998).

Perkins, et al. Boosting with an adenovirus-based vaccine improves protective efficacy against Venezuelan equine encephalitis virus following DNA vaccination. Vaccine. 2006; 24:3440-5.

Phillpotts, et al. Intranasal immunization with defective adenovirus serotype 5 expressing the Venezuelan equine encephalitis virus E2 glycoprotein protects against airborne challenge with virulent virus. Vaccine 23:1615-1623. (2005).

Posavad, et al. Severe genital herpes infections in HIV-infected individuals with impaired herpes simplex virus-specific CD8+ cytotoxic T lymphocyte responses. Proc Natl Acad Sci U S A 94;10289-94 (1997).

Posavad, et al. T cell immunity to herpes simplex viruses in seronegative subjects: silent infection or acquired immunity? J Immunol 170;4380-8 (2003).

Pyles, et al. Use of immunostimulatory sequence-containing oligonucleotides as topical therapy for genital herpes simplex virus type 2 infection. J Virol 76;11387-96 (2002).

Qiu, et al. Evaluation of novel human immunodeficiency virus type 1 Gag DNA vaccines for protein expression in mammalian cells and induction of immune responses. J Virol. 73:9145-52 (1999).

Reddy, et al. Sustained human factor VIII expression in hemophilia A mice following systemic delivery of a gutless adenoviral vector. Mol Ther 5;63-73 (2002).

Renzi, et al. Herpes simplex virus type 2 infection as a risk factor for human immunodeficiency virus acquisition in men who have sex with men. J Infect Dis 187;19-25. (2003).

Roberts, et al. Hexon-chimaeric adenovirus serotype 5 vectors circumvent pre-existing anti-vector immunity. Nature, 2006. 441(7090):239-43.

Rodriques, et al. Importance of CD8 T cell-mediated immune response during intracellular parasitic infections and its implications for the development of effective vaccines. An Acad Bras Cienc 75:.4 443-468 (2003).

Sandig, et al. Optimization of the helper-dependent adenovirus system for production and potency in vivo. Proc Natl Acad Sci U S A 97;1002-7 (2000).

Santosuosso, et al. Mucosal luminal manipulation of T cell geography switches on protective efficacy by otherwise ineffective parenteral genetic immunization. J Immunol 178:.4 2387-395 (2007).

Schaack, et al. E1A and E1B proteins inhibit inflammation induced by adenovirus. Proc Natl Acad Sci U S A. 101:3124-9 (2004).

Schaack. Induction and inhibition of innate inflammatory responses by adenovirus early region proteins. Viral Immunol. 18:79-88 (2005).

Schacker, et al. Frequent recovery of HIV-1 from genital herpes simplex virus lesions in HIV-1-infected men. Jama 280;61-6 (1998).

Schiedner, et al. Genomic DNA transfer with a high-capacity adenovirus vector results in improved in vivo gene expression and decreased toxicity [published erratum appears in Nat Genet Mar. 1998;18(3):298]. Nature Genetics 18;180-3 (1998).

Schmitz, et al. Control of viremia in simian immunodeficiency virus infection by CD8+ lymphocytes. Science 283;857-60 (1999).

Schneider, et al. Inactivation of the human immunodeficiency virus type 1 inhibitory elements allows Rev-independent expression of Gag and Gag/protease and particle formation. J Virol. 71:4892-903 (1997).

Scott, et al. Gutted adenoviral vectors for gene transfer to muscle. Methods Mol Biol 219;19-28 (2003).

Scott, et al. Viral vectors for gene transfer of micro-, mini-, or full-length dystrophin. Neuromuscul Disord 12 Suppl 1;S23-9 (2002).

Shiver, et al. Recent advances in the development of HIV-1 vaccines using replication-incompetent adenovirus vectors. Annu Rev Med. 55;355-72 (2004).

Shiver, et al. Replication-incompetent adenoviral vaccine vector elicits effective anti-immunodeficiency-virus immunity. Nature 415;331-5 (2002).

Sjolander, et al. Induction of a Th1 immune response and simultaneous lack of activation of a Th2 response are required for generation of immunity to leishmaniasis. J Immunol 160:.8 3949-957.(1998).

Skeiky, et al. LeIF: a recombinant *Leishmania* protein that induces an IL-12-medicated Th 1 cytokine profile. J Immunol 161, 6171-6179 (1998).

Skeiky, et al. A recombinant *Leishmania* antigen that stimulates human peripheral blood mononuclear cells to express a Th1-type cytokine profile and to produce interleukin 12. J Exp Med 181, 1527-1537 (1995).

Smith, et al., Transient immunosuppression permits successful repetitive intravenous administration of an adenovirus vector. Gene Ther, 1996. 3(6): p. 496-502.

Stanberry, et al. Glycoprotein-D-adjuvant vaccine to prevent genital herpes. N Engl J Med 347;1652-61. (2002).

Sullivan, et al. Development of a preventive vaccine for Ebola virus infection in primates. Nature 408;605-9 (2000).

Tan, et al. A re-evaluation of the frequency of CD8+ T cells specific for EBV in healthy virus carriers. J Immunol, 1999. 162(3): p. 1827-35.

Tatsis, et al. A CD46-binding Chimpanzee Adenovirus Vector as a Vaccine Carrier. Mol Ther (2007).

Tatsis, et al. Adenoviruses as vaccine vectors. Mol Ther. 10:616-629 (2004).

Thomas, et al. Peripheral infection with adenovirus causes unexpected long-term brain inflammation in animals injected intracranially with first-generation, but not with high-capacity, adenovirus vectors: toward realistic long-term neurological gene therapy for chronic diseases. Proc Natl Acad Sci U S A 97;7482-7 (2000).

Thorner, et al. Immunogenicity of heterologous recombinant adenovirus prime-boost vaccine regimens is enhanced by circumventing vector cross-reactivity. J Virol. Dec. 2006;80(24):12009-16. Epub Oct. 11, 2006.

Treanor, et al. Safety and immunogenicity of an inactivated subviron influenza A (H5N1) N Engl J Med. 354:1343-1351 (2006).

UNAIDS. Epidemiology. http://www.unaids.org/en/resources/epidemiology.asp. Accessed Sep. 1, 2003.

Van Kampen, et al. Safety and immunogenicity of adenovirus-vectored nasal and epicutaneous influenza vaccines in humans. Vaccine, 2005. 23(8): p. 1029-36.

Varnavski, et al. Evaluation of toxicity from high-dose systemic administration of recombinant adenovirus vector in vector-naive and pre-immunized mice. Gene Ther 12:.5 427-436.(2005).

VaxGen I. VaxGen Announces Initial Results of its Phase III AIDS Vaccine Trial. http://www.corporate-ir.net/ireye/ir_site.zhtml?ticker=VXGN&script=410&layout=-6&item_id=385014. Accessed Jul. 14, 2003.

Wald, et al. Polymerase Chain Reaction for Detection of Herpes Simplex Virus (HSV) DNA on Mucosal Surfaces: Comparison with HSV Isolation in Cell Culture. J Infect Dis 188;1345-51 (2003).

Wald, et al.. Risk of human immunodeficiency virus infection in herpes simplex virus type 2-seropositive persons: a meta-analysis. J Infect Dis 185;45-52. (2002).

Wallace, et al. The cytotoxic T-cell response to herpes simplex virus type 1 infection of C57BL/6 mice is almost entirely directed against a single immunodominant determinant. J Virol 73;7619-26 (1999).

Wang, et al. Episomal segregation of the adenovirus enhancer sequence by conditional genome rearrangement abrogates late viral gene expression. J Virol. 2000; 74:11296-303.

Webb, et al. Human and murine immune responses to a novel *Leishmania* major recombinant protein encoded by members of a multicopy gene family. Infect Immun 66, 3279-3289 (1998).

Wille-Reece, et al. Toll-like receptor agonists influence the magnitude and quality of memory T cell responses after prime-boost immunization in nonhuman primates. J Exp Med 203:.5 1249-258 (2006).

Wit, et al. Outcome and predictors of failure of highly active antiretroviral therapy: one-year follow-up of a cohort of human immunodeficiency virus type 1-infected persons. J Infect Dis 179;790-8 (1999).

Wong, et al. Rapid development of T cell memory. J Immunol 172:.12 7239-245 (2004).

Yang, et al. Overcoming immunity to a viral vaccine by DNA priming before vector boosting. J Virol 77;799-803 (2003).

Yang, et al. Role of viral antigens in destructive cellular immune responses to adenovirus vector-transduced cells in mouse lungs. J Virol 70;7209-12 (1996).

Yeh, et al. Efficient dual transcomplementation of adenovirus E1 and E4 regions from a 293-derived cell line expressing a minimal E4 functional unit. J Virol. Jan. 1996;70(1):559-65.

Zhao, et al. Enhanced cellular immunity to SIV Gag following co-administration of adenoviruses encoding wild-type or mutant HIV Tat and SIV Gag. Virology 342:.1 1-12 (2005).

Gaynor, et al. Cis-acting induction of adenovirus transcription. Cell. Jul. 1983;33(3):683-93.

Krougliak, et al. Development of cell lines capable of complementing E1, E4, and protein IX defective adenovirus type 5 mutants. Hum Gene Ther. Dec. 1995;6(12):1575-86.

McMichael, et al. The quest for an AIDS vaccine: is the CD8+ T-cell approach feasible? Nat Rev Immunol. Apr. 2002;2(4):283-91.

Morral, et al. High doses of a helper-dependent adenoviral vector yield supraphysiological levels of alpha1-antitrypsin with negligible toxicity. Hum Gene Ther. Dec. 10, 1998;9(18):2709-16.

Nevins. Mechanism of activation of early viral transcription by the adenovirus E1A gene product. Cell. Oct. 1981;26(2 Pt 2):213-20.

Oualikene, et al. Protease-deleted adenovirus vectors and complementing cell lines: potential applications of single-round replication mutants for vaccination and gene therapy. Hum Gene Ther. Jun. 10, 2000;11(9):1341-53.

Pronk, et al. Adenovirus DNA replication: the function of the covalently bound terminal protein. Chromosoma. 1992;102(1 Suppl):S39-45.

Sumida, et al. Neutralizing antibodies and CD8+ T lymphocytes both contribute to immunity to adenovirus serotype 5 vaccine vectors. J Virol. Mar. 2004;78(6):2666-73.

Thomas, et al. DNA replication and the early to late transition in adenovirus infection. Cell. Nov. 1980;22(2 Pt 2):523-33.

Wang, et al. A packaging cell line for propagation of recombinant adenovirus vectors containing two lethal gene-region deletions. Gene Ther. Dec. 1995;2(10):775-83.

\* cited by examiner

SEQUENTIAL ADMINISTRATION OF A REPLICATION DEFECTIVE ADENOVIRUS VECTOR IN VACCINATION PROTOCOLS

CROSS-REFERENCES TO RELATED APPLICATIONS

This application is a continuation-in-part of PCT Patent Application No. PCT/US2008/068924, filed Jul. 1, 2008, now pending, which application is incorporated herein by reference in its entirety.

This application claims the benefit under 35 U.S.C. §119 (e) of U.S. Provisional Patent Application No. 60/947,601, filed Jul. 2, 2007; where this provisional application is incorporated herein by reference in its entirety.

STATEMENT OF GOVERNMENT INTEREST

This invention was made with government support under Contract No. 1 R43AI071733-01 awarded by the National Institutes of Health, National Institutes of Allergy and Infectious Diseases; Contract No. 2R44AI 1071733-03 awarded by the National Institutes of Health; Contract No. 1R43CA 134063-01 awarded by the National Institutes of Health; and Contract No. 1 R43CA 139663-01 awarded by the National Institutes of Health. The government may have certain rights in this invention.

BACKGROUND

1. Technical Field

The present invention relates to methods for generating immune responses using adenovirus vectors that allow for multiple vaccination regimens.

2. Description of the Related Art

The most difficult problem with adenovirus vectors has been their inability to sustain long-term transgene expression due largely to the host immune response that eliminates the adenovirus vector and virally transduced cells in immune-competent subjects. Thus, the use of First Generation adenovirus vector vaccines is severely limited by preexisting or induced immunity of vaccines to adenovirus (Ad) (Yang, et al. J Virol 77/799-803 (2003); Casimiro, et al. J Virol 77/6305-6313 (2003)). One group reported that a preponderance of humans have antibody against adenovirus type 5 (Ad5), the most widely used serotype for gene transfer vectors, and that two-thirds of humans studied have lymphoproliferative responses against Ad (Chirmule, et al. Gene Ther 6/1574-1583 (1999)). In another study, an adenovirus vector vaccine carrying an HIV-1 envelope gene was incapable of reimmunizing a primed immune response using non-adjuvanted DNA (Barouch, et al. J. Virol 77/8729-8735 (2003)). Another group reported that non-human primates having pre-existing immunity against Ad5 due to a single immunization with Ad5 were unable to generate transgene-specific antibodies to HIV proteins, as well as altering the overall T cell responses (McCoy, et al. J Virol 81/6594-6604 (2007)).

There are numerous mechanisms by which preexisting immunity interferes with adenovirus vector vaccines but the simplest is the presence of neutralizing antibody followed by cell mediated immune elimination of Ad infected antigen harboring cells. Both of these responses are directed to several Ad proteins. Several approaches have been proposed to overcome the barrier of preexisting anti-vector immunity. Perhaps the most straightforward approach would be to increase the vector vaccine dose. Although there is evidence that increasing vaccine doses can increase induction of desired cell mediated immune (CMI) responses in Ad-immune animals (Barouch, et al. J. Virol 77/8729-8735 (2003)), it often results in unacceptable adverse effects in animals and humans. Consequently, most investigators using First Generation Ad5 vector vaccines use the approach of a heterologous prime-boost regimen, using naked (non-vectored) DNA as the priming vaccination, followed by an Ad5 vector immunization. This protocol also results in a subsequent immune response against Ad5 such that one cannot administer a further re-immunization (boost) with the same (or a different) adenovirus vector vaccine that utilizes the same viral backbone. Therefore, with the current First Generation of Ad5 vectors, using this approach also abrogates any further use of Ad5 vector immunization in the Ad5 immunized vaccinee.

First Generation (E1 deleted) adenovirus vector vaccines express Ad late genes, albeit at a decreased level and over a longer time period than wild-type Ad virus (Nevins, et al. Cell 26/213-220 (1981); Gaynor, et al. Cell 33/683-693 (1983); Yang, et al. J Virol 70/7209-7212 (1996)). When using First Generation adenovirus vectors for immunization, vaccine antigens are presented to the immune system simultaneously with highly immunogenic Ad capsid proteins. The major problem with these adenovirus vectors is that the immune responses generated are less likely to be directed to the desired vaccine epitopes (McMichael, et al. Nat Rev Immunol 2/283-291 (2002)) and more likely to be directed to the adenovirus-derived antigens, i.e., antigenic competition. There is controversy about the mechanism by which First Generation adenovirus vectors are potent immunogens. It has been hypothesized that the composition of the Ad capsid or a toxic effect of viral genes creates generalized inflammation resulting in a nonspecific immune stimulatory effect. The E1 proteins of Ad act to inhibit inflammation following infection (Schaack, et al. PNAS 101/3124-3129 (2004)). Removal of the gene segments for these proteins, which is the case for First Generation adenovirus vectors, results in increased levels of inflammation (Schaack, et al. PNAS 101/3124-3129 (2004); Schaack, et al. Viral Immunol 18/79-88 (2005)). It has been reported that adenovirus vectors efficiently infect antigen-presenting cells (APC) such as dendritic cells and less immunogenic viral vectors do not (Jooss, et al. J Virol 72/4212-4223 (1998)). Antigen presenting cells (APC), such as dendritic cells, are responsible for initiation of CMI responses (Kirk, et al. Hum Gene Ther 11/797-806 (2000)). It has been reported that prevention of gene expression in dendritic cells greatly reduces the intensity of the CMI response (Hartigan-O'Connor, et al. Mol Ther 4/525-533 (2001)).

Thus, it is apparent that there remains a need for a more effective vaccine vector candidate. In particular, there remains a need in the art for Ad vaccine vectors that allow multiple vaccinations and vaccinations in individuals with preexisting immunity to Ad. In addition, there is no homologous vaccine delivery vector that can be employed in a prime reimmunization protocol for vaccination. The present invention provides this and other advantages.

BRIEF SUMMARY

One aspect of the invention provides a method of generating an immune response against one or more target antigens in an individual comprising administering to the individual an adenovirus vector comprising: a) a replication defective adenovirus vector, wherein the adenovirus vector has a deletion in the E2b region, and b) a nucleic acid encoding the one or more target antigens; and readministering the adenovirus vector at least once to the individual; thereby generating an immune response against the one or more target antigens.

Another aspect of the invention provides a method for generating an immune response against one or more target antigens in an individual, wherein the individual has preexisting immunity to adenovirus, comprising: administering to the individual an adenovirus vector comprising: a) a replication defective adenovirus vector, wherein the adenovirus vector has a deletion in the E2b region, and b) a nucleic acid encoding the one or more target antigens; and readministering the adenovirus vector at least once to the individual; thereby generating an immune response against the one or more target antigens.

In one embodiment of the methods described herein, the target antigen comprises an HIV protein, a human papilloma virus protein, a herpes simplex virus protein, a hepatitis C virus protein, a malaria protein, a plague protein, a *M. tuberculosis* protein, or a *Streptococcus pneumonia* protein, or an immunogenic fragment or variant thereof. In certain embodiments, the HIV protein is an HIV-gag protein. In a further embodiment, the target antigen comprises an antigen derived from a Venezuelan Equine Encephalitis Virus (VEEV), Western Equine Encephalitis Virus, or Japanese Encephalitis Virus protein. In yet further embodiments, the target antigen comprises a *Leishmania* protein, a cancer protein such as carcinoembryonic antigen, Her2/Neu, a human papilloma virus protein, or WT-1, or a variant or fragment thereof. In a particular embodiment, the human papilloma virus protein is E6. In another embodiment, the human papilloma virus protein is E7. In certain embodiments, the target antigen is a variant having one or more reduced biological activities as compared to the wild type target antigen. In particular embodiments, a target antigen is a variant that is modified to have reduced oncogenicity as compared to the wild type target antigen.

In one embodiment, the target antigen comprises an antigen derived from an influenza virus protein, or a variant or fragment thereof. In this regard, the influenza protein may be derived from the H5N1 influenza virus. In a further embodiment, the influenza virus protein may be derived from any influenza virus, including but not limited to H3N2, H9N1, H1N1, H2N2, H7N7, H1N2, H9N2, H7N2, H7N3, or H10N7. In certain embodiments, the influenza virus protein may be any influenza protein, including but not limited to, haemagglutinin, neuraminidase, or matrix protein M1.

A further aspect of the invention provides a method of generating an immune response against one or more target antigens in an individual comprising: administering to the individual a first adenovirus vector comprising: a) a replication defective adenovirus vector, wherein the adenovirus vector has a deletion in the E2b region, and b) a nucleic acid encoding at least one target antigen; and administering to the individual a second adenovirus vector comprising: a) a replication defective adenovirus vector, wherein the adenovirus vector has a deletion in the E2b region, and b) a nucleic acid encoding at least one target antigen, wherein the at least one target antigen of the second adenovirus vector is the same or different from the at least one target antigen of the first adenovirus vector; thereby generating an immune response against one or more target antigens.

In one embodiment of the methods provided herein, the adenovirus vector is not a gutted vector. In another embodiment of the methods provided herein, the individual has preexisting immunity to adenovirus. In a further embodiment, the at least one target antigen of the first and the second adenovirus vectors are derived from the same infectious organism. In another embodiment, the at least one target antigen of the first and the second adenovirus vectors are derived from different infectious organisms.

In yet another embodiment of the methods of the invention, the at least one target antigen of the first adenovirus vector comprises an HIV protein. In a further embodiment, the at least one target antigen of the first adenovirus vector comprises an HIV protein and the at least one target antigen of the second adenovirus vector comprises an HIV protein. In another embodiment, the at least one target antigen of the first adenovirus vector comprises an HIV protein and the at least one target antigen of the second adenovirus vector comprises an HIV protein that is different from the HIV protein of the first adenovirus vector. In a further embodiment, the HIV protein of the first or second adenovirus vector is an HIV-gag protein. In a yet further embodiment, the first adenovirus vector comprises an HIV-gag protein and the second adenovirus vector comprises β-galactosidase. In certain embodiments, the β-galactosidase is an *E. coli* β-galactosidase.

In certain embodiments of the methods provided herein, the at least one target antigen of the first adenovirus vector comprises a cancer protein (e.g., a Her2/neu antigen, a human papilloma virus protein or a carcinoembryonic protein), or a fragment or variant thereof. In other embodiments, the at least one target antigen of the first adenovirus vector comprises a bacterial antigen, a viral antigen, an antigen derived from a protozoan protein, an antigen derived from a fungal protein, an antigen derived from a mold protein, an antigen derived from any mammalian protein, or an antigen derived from an avian protein, or a fragment or variant thereof. In certain embodiments, the target antigen is a variant having one or more reduced biological activities as compared to the wild type target antigen. In particular embodiments, a target antigen is a variant that is modified to have reduced oncogenicity as compared to the wild type target antigen.

In a further related embodiment, the present invention includes an adenovirus vector comprising: i) a replication defective adenovirus vector, wherein the adenovirus vector has a deletion in the E2b region, and ii) a nucleic acid encoding one or more target antigens, wherein said one or more target antigens comprises a modified cancer protein having one or more reduced activities. In one embodiment, the modified cancer protein has reduced oncogenic activity. In one embodiment, the modified cancer protein is a modified Her2/neu protein having reduced kinase activity. In one embodiment, the modified cancer protein is a modified human papillomavirus E6 protein having reduced binding to p53. In one embodiment, the modified cancer protein is a modified human papillomavirus E7 protein having reduced binding to Rb.

DETAILED DESCRIPTION

Figure 1:
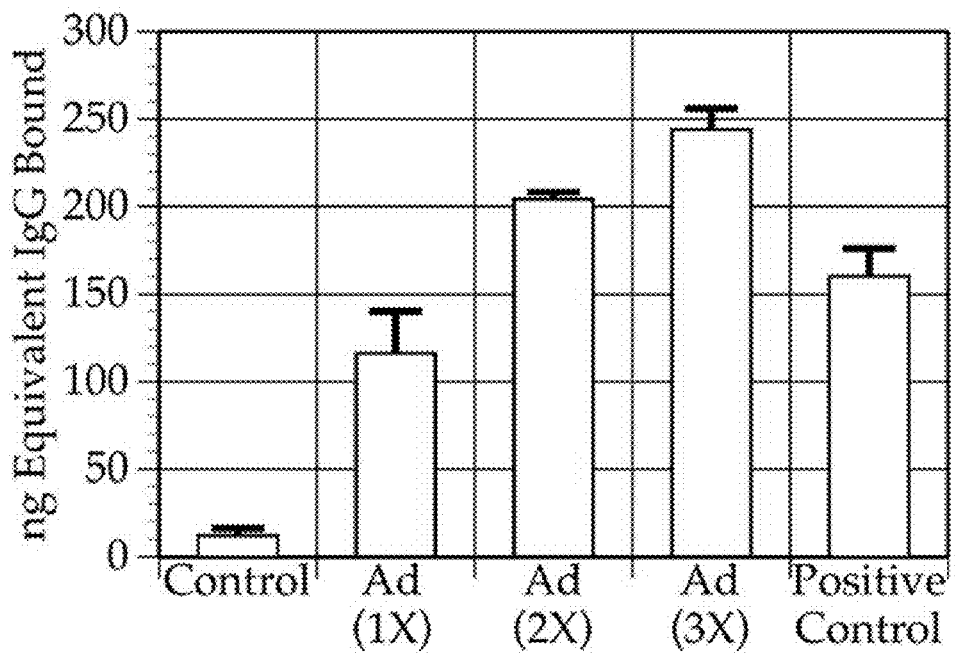
FIG. 1 is a bar graph showing antibody levels from mice immunized with Ad5Null. Mice were immunized three times with Ad5Null viral particles at 14 day intervals. Note the presence of increasing anti-Ad antibody levels after each immunization.

The present invention relates to methods and adenovirus vectors for generating immune responses against target antigens. In particular, the present invention provides an improved adenovirus (Ad)-based vaccine such that multiple vaccinations against one or more antigenic target entity can be achieved. Importantly, vaccination can be performed in the presence of preexisting immunity to the Ad and/or administered to subjects previously immunized multiple times with the adenovirus vector of the present invention or other adenovirus vectors. The adenovirus vectors of the invention can be administered to subjects multiple times to induce an immune response against an antigen of interest, including but not limited to, the production of antibodies and cell-mediated immune responses against one or more target antigens.

To facilitate an understanding of the present invention, a number of terms and phrases are defined below.

The term "adenovirus" or "Ad" refers to a group of non-enveloped DNA viruses from the family Adenoviridae. In addition to human hosts, these viruses can be found in, but are not limited to, avian, bovine, porcine and canine species. The present invention contemplates the use of any adenovirus from any of the four genera of the family Adenoviridae (e.g., Aviadenovirus, Mastadenovirus, Atadenovirus and Siadenovirus) as the basis of an E2b deleted virus vector, or vector containing other deletions as described herein. In addition, several serotypes are found in each species. Ad also pertains to genetic derivatives of any of these viral serotypes, including but not limited to, genetic mutation, deletion or transposition of homologous or heterologous DNA sequences.

A "helper adenovirus" or "helper virus" refers to an Ad that can supply viral functions that a particular host cell cannot (the host may provide Ad gene products such as E1 proteins). This virus is used to supply, in trans, functions (e.g., proteins) that are lacking in a second virus, or helper dependent virus (e.g., a gutted or gutless virus, or a virus deleted for a particular region such as E2b or other region as described herein); the first replication-incompetent virus is said to "help" the second, helper dependent virus thereby permitting the production of the second viral genome in a cell.

The term "Adenovirus5 null (Ad5null)", as used herein, refers to a non-replicating Ad that does not contain any heterologous nucleic acid sequences for expression.

The term "First Generation adenovirus", as used herein, refers to an Ad that has the early region 1 (E1) deleted. In additional cases, the nonessential early region 3 (E3) may also be deleted.

The term "gutted" or "gutless", as used herein, refers to an adenovirus vector that has been deleted of all viral coding regions.

The term "transfection" as used herein refers to the introduction of foreign nucleic acid into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign nucleic acid, DNA or RNA, into the genome of the transfected cell. The term "stable transfectant" refers to a cell which has stably integrated foreign DNA into the genomic DNA.

The term "reporter gene" indicates a nucleotide sequence that encodes a reporter molecule (including an enzyme). A "reporter molecule" is detectable in any of a variety of detection systems, including, but not limited to enzyme-based detection assays (e.g., ELISA, as well as enzyme-based histochemical assays), fluorescent, radioactive, and luminescent systems. In one embodiment, the present invention contemplates the E. coli β-galactosidase gene (available from Pharmacia Biotech, Pistacataway, N.J.), green fluorescent protein (GFP) (commercially available from Clontech, Palo Alto, Calif.), the human placental alkaline phosphatase gene, the chloramphenicol acetyltransferase (CAT) gene; other reporter genes are known to the art and may be employed.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The nucleic acid sequence thus codes for the amino acid sequence.

The term "heterologous nucleic acid sequence", as used herein, refers to a nucleotide sequence that is ligated to, or is manipulated to become ligated to, a nucleic acid sequence to which it is not ligated in nature, or to which it is ligated at a different location in nature. Heterologous nucleic acid may include a nucleotide sequence that is naturally found in the cell into which it is introduced or the heterologous nucleic acid may contain some modification relative to the naturally occurring sequence.

The term "transgene" refers to any gene coding region, either natural or heterologous nucleic acid sequences or fused homologous or heterologous nucleic acid sequences, introduced into the cells or genome of a test subject. In the current invention, transgenes are carried on any viral vector that is used to introduce the transgenes to the cells of the subject.

The term "Second Generation Adenovirus", as used herein, refers to an Ad that has all or parts of the E1, E2, E3, and, in certain embodiments, E4 DNA gene sequences deleted (removed) from the virus.

The term "subject", as used herein, refers to any animal, e.g., a mammal or marsupial. Subjects of the present invention include but are not limited to humans, non-human primates (e.g., rhesus or other types of macaques), mice, pigs, horses, donkeys, cows, sheep, rats and fowl of any kind.

Adenovirus Vectors

Compared to First Generation adenovirus vectors, certain embodiments of the Second Generation E2b deleted adenovirus vectors of the present invention contain additional deletions in the DNA polymerase gene (pol) and deletions of the pre-terminal protein (pTP). E2b deleted vectors have up to a 13 kb gene-carrying capacity as compared to the 5 to 6 kb capacity of First Generation adenovirus vectors, easily providing space for nucleic acid sequences encoding any of a variety of target antigens, including for example, the Gag, Pol and Nef genes of HIV (Amalfitano, et al. Curr Gene Ther 2/111-133 (2002)). The E2b deleted adenovirus vectors also have reduced adverse reactions as compared to First Generation adenovirus vectors (Morral, et al Hum Gene Ther 9/2709-2716 (1998); Hodges, et al. J Gene Med 2/250-259

(2000); DelloRusso, et al. Proc Natl Acad Sci USA 99/12979-12984 (2002); Reddy, et al. Mol Ther 5/63-73 (2002); (Amalfitano and Parks, et al. Curr Gene Ther 2/111-133 (2002); Amalfitano Curr Opin Mol Ther 5/362-366 (2003); Everett, et al. Human Gene Ther 14/1715-1726 (2003)) E2b deleted vectors have reduced expression of viral genes (Hodges, et al. J Gene Med 2/250-259 (2000); Amalfitano, et al. J Virol 72/926-933 (1998); Hartigan-O'Connor, et al. Mol Ther 4/525-533 (2001)), and this characteristic has been reported to lead to extended transgene expression in vivo (Hu, et al. Hum Gene Ther 10/355-364 (1999); DelloRusso, et al. Proc Natl Acad Sci USA 99/12979-12984 (2002); Reddy, et al. Mol Ther 5/63-73 (2002); (Amalfitano and Parks, et al. Curr Gene Ther 2/111-133 (2002); Amalfitano Curr Opin Mol Ther 5/362-366 (2003); Everett, et al. Human Gene Ther 14/1715-1726 (2003)).

The innate immune response to wild type Ad can be complex, and it appears that Ad proteins expressed from adenovirus vectors play an important role (Moorhead, et al. J Virol 73/1046-1053 (1999); Nazir, et al. J Investig Med 53/292-304 (2005); Schaack, et al. Proc Natl Acad Sci USA 101/3124-3129 (2004); Schaack, et al. Viral Immunol 18/79-88 (2005); Kiang, et al. Mol Ther 14/588-598 (2006); Hartman, et al. J Virol 81/1796-1812 (2007); Hartman, et al. Virology 358/357-372 (2007)). Specifically, the deletions of pre-terminal protein and DNA polymerase in the E2b deleted vectors appear to reduce inflammation during the first 24 to 72 hours following injection, whereas First Generation adenovirus vectors stimulate inflammation during this period (Schaack, et al. Proc Natl Acad Sci USA 101/3124-3129 (2004); Schaack, et al. Viral Immunol 18/79-88 (2005); Kiang, et al. Mol Ther 14/588-598 (2006); Hartman, et al. J Virol 81/1796-1812 (2007); Hartman, et al. Virology 358/357-372 (2007)). In addition, it has been reported that the additional replication block created by E2b deletion also leads to a 10,000 fold reduction in expression of Ad late genes, well beyond that afforded by E1, E3 deletions alone (Amalfitano et al. J. Virol. 72/926-933 (1998); Hodges et al. J. Gene Med. 2/250-259 (2000)). The decreased levels of Ad proteins produced by E2b deleted adenovirus vectors effectively reduce the potential for competitive, undesired, immune responses to Ad antigens, responses that prevent repeated use of the platform in Ad immunized or exposed individuals. The reduced induction of inflammatory response by Second Generation E2b deleted vectors results in increased potential for the vectors to express desired vaccine antigens during the infection of antigen presenting cells (i.e. dendritic cells), decreasing the potential for antigenic competition, resulting in greater immunization of the vaccine to the desired antigen relative to identical attempts with First Generation adenovirus vectors. E2b deleted adenovirus vectors provide an improved Ad-based vaccine candidate that is safer, more effective, and more versatile than previously described vaccine candidates using First Generation adenovirus vectors.

Thus, the present invention contemplates the use of E2b deleted adenovirus vectors, such as those described in U.S. Pat. Nos. 6,063,622; 6,451,596; 6,057,158: and 6,083,750. As described in the '622 patent, in order to further cripple viral protein expression, and also to decrease the frequency of generating replication competent Ad (RCA), the present invention provides adenovirus vectors containing deletions in the E2b region. Propagation of these E2b deleted adenovirus vectors requires cell lines that express the deleted E2b gene products. The present invention also provides such packaging cell lines; for example E.C7 (formally called C-7), derived from the HEK-203 cell line (Amalfitano, et al. Proc Natl Acad Sci USA 93/3352-3356 (1996); Amalfitano, et al. Gene Ther 4/258-263 (1997)).

Further, the E2b gene products, DNA polymerase and preterminal protein, can be constitutively expressed in E.C7, or similar cells along with the E1 gene products. Transfer of gene segments from the Ad genome to the production cell line has immediate benefits: (1) increased carrying capacity of the recombinant DNA polymerase and preterminal protein-deleted adenovirus vector, since the combined coding sequences of the DNA polymerase and preterminal proteins that can be theoretically deleted approaches 4.6 kb; and, (2) a decreased potential of RCA generation, since two or more independent recombination events would be required to generate RCA. Therefore, the E1, Ad DNA polymerase and preterminal protein expressing cell lines used in the present invention enable the propagation of adenovirus vectors with a carrying capacity approaching 13 kb, without the need for a contaminating helper virus [Mitani et al. (1995) Proc. Natl. Acad. Sci. USA 92:3854; Hodges, et al., 2000 J Gene Med 2:250-259; (Amalfitano and Parks, Curr Gene Ther 2/111-133 (2002)]. In addition, when genes critical to the viral life cycle are deleted (e.g., the E2b genes), a further crippling of Ad to replicate or express other viral gene proteins occurs. This will decrease immune recognition of virally infected cells, and allows for extended durations of foreign transgene expression.

The most important attribute of E1, DNA polymerase, and preterminal protein deleted vectors, however, is their inability to express the respective proteins from the E1 and E2b regions, as well as a predicted lack of expression of most of the viral structural proteins. For example, the major late promoter (MLP) of Ad is responsible for transcription of the late structural proteins L1 through L5 [Doerfler, In Adenovirus DNA, The Viral Genome and Its Expression (Martinus Nijhoff Publishing Boston, 1986)]. Though the MLP is minimally active prior to Ad genome replication, the highly toxic Ad late genes are primarily transcribed and translated from the MLP only after viral genome replication has occurred [Thomas and Mathews (1980) Cell 22:523]. This cis-dependent activation of late gene transcription is a feature of DNA viruses in general, such as in the growth of polyoma and SV-40. The DNA polymerase and preterminal proteins are absolutely required for Ad replication (unlike the E4 or protein IX proteins) and thus their deletion is extremely detrimental to adenovirus vector late gene expression, and the toxic effects of that expression in cells such as APCs.

In certain embodiments, the adenovirus vectors contemplated for use in the present invention include E2b deleted adenovirus vectors that have a deletion in the E2b region of the Ad genome and the E1 region but do not have any other regions of the Ad genome deleted. In another embodiment, the adenovirus vectors contemplated for use in the present invention include E2b deleted adenovirus vectors that have a deletion in the E2b region of the Ad genome and deletions in the E1 and E3 regions, but no other regions deleted. In a further embodiment, the adenovirus vectors contemplated for use in the present invention include adenovirus vectors that have a deletion in the E2b region of the Ad genome and deletions in the E1, E3 and partial or complete removal of the E4 regions but no other deletions. In another embodiment, the adenovirus vectors contemplated for use in the present invention include adenovirus vectors that have a deletion in the E2b region of the Ad genome and deletions in the E1 and E4 regions but no other deletions. In an additional embodiment, the adenovirus vectors contemplated for use in the present invention include adenovirus vectors that have a deletion in the E2a, E2b and E4 regions of the Ad genome but no other deletions. In one embodiment, the adenovirus vectors for use herein comprise vectors having the E1 and DNA polymerase functions of the E2b region deleted but no other deletions. In a further embodiment, the adenovirus vectors for use herein have the E1 and the preterminal protein functions of the E2b region deleted and no other deletions. In another embodiment, the adenovirus vectors for use herein have the E1, DNA polymerase and the preterminal protein functions deleted, and no other deletions. In one particular embodiment, the adenovirus vectors contemplated for use herein are deleted for at least a portion of the E2b region and the E1 region, but are not "gutted" adenovirus vectors. In this regard, the vectors may be deleted for both the DNA polymerase and the preterminal protein functions of the E2b region. In an additional embodiment, the adenovirus vectors for use in the present invention include adenovirus vectors that have a deletion in the E1, E2b and 100K regions of the adenovirus genome. In one embodiment, the adenovirus vectors for use herein comprise vectors having the E1, E2b and protease functions deleted but no other deletions. In a further embodiment, the adenovirus vectors for use herein have the E1 and the E2b regions deleted, while the fiber genes have been modified by mutation or other alterations (for example to alter Ad tropism). Removal of genes from the E3 or E4 regions may be added to any of the mentioned adenovirus vectors. In certain embodiments, the adenovirus vector may be a "gutted" adenovirus vector.

The term "E2b deleted", as used herein, refers to a specific DNA sequence that is mutated in such a way so as to prevent expression and/or function of at least one E2b gene product. Thus, in certain embodiments, "E2b deleted" refers to a specific DNA sequence that is deleted (removed) from the Ad genome. E2b deleted or "containing a deletion within the E2b region" refers to a deletion of at least one base pair within the E2b region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, the deletion is of more than 150, 160, 170, 180, 190, 200, 250, or 300 base pairs within the E2b region of the Ad genome. An E2b deletion may be a deletion that prevents expression and/or function of at least one E2b gene product and therefore, encompasses deletions within exons encoding portions of E2b-specific proteins as well as deletions within promoter and leader sequences. In certain embodiments, an E2b deletion is a deletion that prevents expression and/or function of one or both of the DNA polymerase and the preterminal protein of the E2b region. In a further embodiment, "E2b deleted" refers to one or more point mutations in the DNA sequence of this region of an Ad genome such that one or more encoded proteins is non-functional. Such mutations include residues that are replaced with a different residue leading to a change in the amino acid sequence that result in a nonfunctional protein.

As would be understood by the skilled artisan upon reading the present disclosure, other regions of the Ad genome can be deleted. Thus to be "deleted" in a particular region of the Ad genome, as used herein, refers to a specific DNA sequence that is mutated in such a way so as to prevent expression and/or function of at least one gene product encoded by that region. In certain embodiments, to be "deleted" in a particular region refers to a specific DNA sequence that is deleted (removed) from the Ad genome in such a way so as to prevent the expression and/or the function encoded by that region (e.g., E2b functions of DNA polymerase or preterminal protein function). "Deleted" or "containing a deletion" within a particular region refers to a deletion of at least one base pair within that region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted from a particular region. In another embodiment, the deletion is more than 150, 160, 170, 180, 190, 200, 250, or 300 base pairs within a particular region of the Ad genome. These deletions are such that expression and/or function of the gene product encoded by the region is prevented. Thus deletions encompass deletions within exons encoding portions of proteins as well as deletions within promoter and leader sequences. In a further embodiment, "deleted" in a particular region of the Ad genome refers to one or more point mutations in the DNA sequence of this region of an Ad genome such that one or more encoded proteins is non-functional. Such mutations include residues that are replaced with a different residue leading to a change in the amino acid sequence that result in a nonfunctional protein.

The deleted adenovirus vectors of the present invention can be generated using recombinant techniques known in the art (see e.g., Amalfitano et al., 1998 J. Virol. 72:926-933; Hodges, et al., 2000 J Gene Med 2:250-259).

As would be recognized by the skilled artisan, the adenovirus vectors for use in the present invention can be successfully grown to high titers using an appropriate packaging cell line that constitutively expresses E2b gene products and products of any of the necessary genes that may have been deleted. In certain embodiments, HEK-293-derived cells that not only constitutively express the E1 and DNA polymerase proteins, but also the Ad-preterminal protein, can be used. In one embodiment, E.C7 cells are used to successfully grow high titer stocks of the adenovirus vectors (see e.g., Amalfitano et al., J. Virol. 1998 72:926-933; Hodges, et al. J Gene Med 2/250-259 (2000))

In order to delete critical genes from self-propagating adenovirus vectors, the proteins encoded by the targeted genes have to first be coexpressed in HEK-293 cells, or similar, along with the E1 proteins. Therefore, only those proteins which are non-toxic when coexpressed constitutively (or toxic proteins inducibly-expressed) can be utilized. Coexpression in HEK-293 cells of the E1 and E4 genes has been demonstrated (utilizing inducible, not constitutive, promoters) [Yeh et al. (1996) J. Virol. 70:559; Wang et al. (1995) Gene Therapy 2:775; and Gorziglia et al. (1996) J. Virol. 70:4173]. The E1 and protein IX genes (a virion structural protein) have been coexpressed [Caravokyri and Leppard (1995) J. Virol. 69:6627], and coexpression of the E1, E4, and protein IX genes has also been described [Krougliak and Graham (1995) Hum. Gene Ther. 6:1575]. The E1 and 100 k genes have been successfully expressed in transcomplementing cell lines, as have E1 and protease genes (Oualikene, et al. Hum Gene Ther 11/1341-1353 (2000); Hodges, et al. J. Virol 75/5913-5920 (2001)).

Cell lines coexpressing E1 and E2b gene products for use in growing high titers of E2b deleted Ad particles are described in U.S. Pat. No. 6,063,622. The E2b region encodes the viral replication proteins which are absolutely required for Ad genome replication [Doerfler, supra and Pronk et al. (1992) Chromosoma 102:S39-S45]. Useful cell lines constitutively express the approximately 140 kD Ad-DNA polymerase and/or the approximately 90 kD preterminal protein. In particular, cell lines that have high-level, constitutive coexpression of the E1, DNA polymerase, and preterminal proteins, without toxicity (e.g. E.C7), are desirable for use in propagating Ad for use in multiple vaccinations. These cell lines permit the propagation of adenovirus vectors deleted for the E1, DNA polymerase, and preterminal proteins.

The recombinant Ad of the present invention can be propagated using techniques known in the art. For example, in certain embodiments, tissue culture plates containing E.C7 cells are infected with the adenovirus vector virus stocks at an appropriate MOI (e.g., 5) and incubated at 37.0° C. for 40-96 h. The infected cells are harvested, resuspended in 10 mM Tris-Cl (pH 8.0), and sonicated, and the virus is purified by two rounds of cesium chloride density centrifugation. In certain techniques, the virus containing band is desalted over a Sephadex CL-6B column (Pharmacia Biotech, Piscataway, N.J.), sucrose or glycerol is added, and aliquots are stored at −80° C. In some embodiments, the virus will be placed in a solution designed to enhance its stability, such as A195 (Evans, et al. J Pharm Sci 93/2458-2475 (2004)) The titer of the stock is measured (e.g., by measurement of the optical density at 260 nm of an aliquot of the virus after SDS lysis). In another embodiment, plasmid DNA, either linear or circular, encompassing the entire recombinant E2b deleted adenovirus vector can be transfected into E.C7, or similar cells, and incubated at 37.0° C. until evidence of viral production is present (e.g. the cytopathic effect). The conditioned media from these cells can then be used to infect more E.C7, or similar cells, to expand the amount of virus produced, before purification. Purification can be accomplished by two rounds of cesium chloride density centrifugation or selective filtration. In certain embodiments, the virus may be purified by column chromatography, using commercially available products (e.g. Adenopure from Puresyn, Inc., Malvern, Pa.) or custom made chromatographic columns.

Generally, the recombinant Ad of the present invention comprises enough of the virus to ensure that the cells to be infected are confronted with a certain number of viruses. Thus, the present invention provides a stock of recombinant Ad, preferably an RCA-free stock of recombinant Ad. The preparation and analysis of Ad stocks is well known in the art. Viral stocks vary considerably in titer, depending largely on viral genotype and the protocol and cell lines used to prepare them. The viral stocks of the present invention can have a titer of at least about $10^6$, $10^7$, or $10^8$ pfu/ml, and many such stocks can have higher titers, such as at least about $10^9$, $10^{10}$, $10^{11}$, or $10^{12}$ pfu/ml. Depending on the nature of the recombinant virus and the packaging cell line, it is possible that a viral stock of the present invention can have a titer of even about $10^{13}$ particles/ml or higher.

Further information on viral delivery systems is known in the art and can be found, for example, in Fisher-Hoch et al., *Proc. Natl. Acad. Sci. USA* 86:317-321, 1989; Flexner et al., *Ann. N.Y. Acad. Sci.* 569:86-103, 1989; Flexner et al., *Vaccine* 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627, 1988; Rosenfeld et al., *Science* 252:431-434, 1991; Kolls et al., *Proc. Natl. Acad. Sci. USA* 91:215-219, 1994; Kass-Eisler et al., *Proc. Natl. Acad. Sci. USA* 90:11498-11502, 1993; Guzman et al., *Circulation* 88:2838-2848, 1993; and Guzman et al., *Cir. Res.* 73:1202-1207, 1993.

Heterologous Nucleic Acid

The adenovirus vectors of the present invention also comprise heterologous nucleic acid sequences that encode one or more target antigens of interest, or variants, fragments or fusions thereof, against which it is desired to generate an immune response. In some embodiments, the adenovirus vectors of the present invention comprise heterologous nucleic acid sequences that encode one or more proteins, variants thereof, fusions thereof, or fragments thereof, that can modulate the immune response. In a further embodiment of the invention, the adenovirus vector of the present invention encodes one or more antibodies against specific antigens, such as anthrax protective antigen, permitting passive immunotherapy. In certain embodiments, the adenovirus vectors of the present invention comprise heterologous nucleic acid sequences encoding one or more proteins having therapeutic effect (e.g., anti-viral, anti-bacterial, anti-parasitic, or anti-tumor function). Thus the present invention provides the Second Generation E2b deleted adenovirus vectors that comprise a heterologous nucleic acid sequence.

As such, the present invention further provides nucleic acid sequences, also referred to herein as polynucleotides, that encode one or more target antigens of interest, or fragments or variants thereof. As such, the present invention provides polynucleotides that encode target antigens from any source as described further herein, vectors comprising such polynucleotides and host cells transformed or transfected with such expression vectors. The terms "nucleic acid" and "polynucleotide" are used essentially interchangeably herein. As will be also recognized by the skilled artisan, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials. An isolated polynucleotide, as used herein, means that a polynucleotide is substantially away from other coding sequences. For example, an isolated DNA molecule as used herein does not contain large portions of unrelated coding DNA, such as large chromosomal fragments or other functional genes or polypeptide coding regions. Of course, this refers to the DNA molecule as originally isolated, and does not exclude genes or coding regions later added to the segment recombinantly in the laboratory.

As will be understood by those skilled in the art, the polynucleotides of this invention can include genomic sequences, extra-genomic and plasmid-encoded sequences and smaller engineered gene segments that express, or may be adapted to express target antigens as described herein, fragments of antigens, peptides and the like. Such segments may be naturally isolated, or modified synthetically by the hand of man.

Polynucleotides may comprise a native sequence (i.e., an endogenous sequence that encodes a target antigen polypeptide/protein/epitope of the invention or a portion thereof) or may comprise a sequence that encodes a variant, fragment, or derivative of such a sequence. In certain embodiments, the polynucleotide sequences set forth herein encode target antigen proteins as described herein. In some embodiments, polynucleotides represent a novel gene sequence that has been optimized for expression in specific cell types (i.e. human cell lines) that may substantially vary from the native nucleotide sequence or variant but encode a similar protein antigen.

In other related embodiments, the present invention provides polynucleotide variants having substantial identity to native sequences encoding proteins (e.g., target antigens of interest) as described herein, for example those comprising at least 70% sequence identity, preferably at least 75%, 80%, 85%, 90%, 95%, 96%, 97%, 98%, or 99% or higher, sequence identity compared to a native polynucleotide sequence encoding the polypeptides of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the immunogenicity of the epitope of the polypeptide encoded by the variant polynucleotide or such that the immunogenicity of the heterologous target protein is not substantially diminished relative to a polypeptide encoded by the native polynucleotide sequence. As described elsewhere herein, the polynucleotide variants preferably encode a variant of the target antigen, or a fragment (e.g., an epitope) thereof wherein the propensity of the variant polypeptide or fragment (e.g., epitope) thereof to react with antigen-specific antisera and/or T-cell lines or clones is not substantially diminished relative to the native polypeptide. The term "variants" should also be understood to encompass homologous genes of xenogenic origin. In particular embodiments, variants or fragments of target antigens are modified such that they have one or more reduced biological activities. For example, an oncogenic protein target antigen may be modified to reduce or eliminate the oncogenic activity of the protein, or a viral protein may be modified to reduce or eliminate one or more activities or the viral protein. An example of a modified HER2 protein is a kinase-inactive HER2 having a K753A mutation that renders it non-oncogenic, as described in Morse, M. A. et al., Int. J. Cancer, 2009, Vol. 9999, Issue 999A, page NA, published online 23 Oct. 2009; and Akiyama, T. et al., Mol. Cell. Biol. 1991, 11(2): 833-842.

The present invention provides polynucleotides that comprise or consist of at least about 5, 10, 15, 20, 25, 30, 35, 40, 45, 50, 55, 60, 65, 70, 75, 80, 85, 90, 95, 100, 11, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, or 1000 or more contiguous nucleotides encoding a polypeptide, including target protein antigens, as described herein, as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. A polynucleotide sequence as described herein may be extended at one or both ends by additional nucleotides not found in the native sequence encoding a polypeptide as described herein, such as an epitope or heterologous target protein. This additional sequence may consist of 1, 2, 3, 4, 5, 6, 7, 8, 9, 10, 11, 12, 13, 14, 15, 16, 17, 18, 19, or 20 nucleotides or more, at either end of the disclosed sequence or at both ends of the disclosed sequence.

The polynucleotides of the present invention, or fragments thereof, regardless of the length of the coding sequence itself, may be combined with other DNA sequences, such as promoters, expression control sequences, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 1000, 2000, 3000, 4000, 5000, 6000, 7000, 8000, 9000, 10,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Washington D.C. Vol. 5, Suppl. 3, pp. 345-358; Hein J., *Unified Approach to Alignment and Phylogenes*, pp. 626-645 (1990); *Methods in Enzymology* vol. 183, Academic Press, Inc., San Diego, Calif.; Higgins, D. G. and Sharp, P. M., *CABIOS* 5:151-153 (1989); Myers, E. W. and Muller W., *CABIOS* 4:11-17 (1988); Robinson, E. D., *Comb. Theor* 11:105 (1971); Saitou, N. Nei, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, and expectation (E) of 10, and the BLOSUM62 scoring matrix (see Henikoff and Henikoff, *Proc. Natl. Acad. Sci. USA* 89:10915 (1989)) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a particular antigen of interest, or fragment thereof, as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Therefore, in another embodiment of the invention, a mutagenesis approach, such as site-specific mutagenesis, is employed for the preparation of variants and/or derivatives of the target antigen sequences, or fragments thereof, as described herein. By this approach, specific modifications in a polypeptide sequence can be made through mutagenesis of the underlying polynucleotides that encode them. These techniques provide a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the immunogenicity of an epitope comprised in a polypeptide or the oncogenicity of a target antigen. In certain embodiments, a kinase domain is inactivated in a target antigen. Assays to test the immunogenicity of a polypeptide or variant thereof are well known in the art and include, but are not limited to, T cell cytotoxicity assays (CTL/chromium release assays), T cell proliferation assays, intracellular cytokine staining, ELISA, ELISpot, etc. The techniques of site-specific mutagenesis are well known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

The preparation of sequence variants of the selected peptide-encoding DNA segments using site-directed mutagenesis provides a means of producing potentially useful species and is not meant to be limiting, as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982.

Polynucleotide segments or fragments encoding the polypeptides of the present invention may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202, by introducing selected sequences into recombinant vectors for recombinant production, and by other recombinant DNA techniques generally known to those of skill in the art of molecular biology (see for example, Current Protocols in Molecular Biology, John Wiley and Sons, NY, N.Y.).

In order to express a desired target antigen polypeptide or fragment or variant thereof, or fusion protein comprising any of the above, as described herein, the nucleotide sequences encoding the polypeptide, or functional equivalents, are inserted into an appropriate Ad as described elsewhere herein using recombinant techniques known in the art. The appropriate adenovirus vector contains the necessary elements for the transcription and translation of the inserted coding sequence and any desired linkers. Methods which are well known to those skilled in the art may be used to construct these adenovirus vectors containing sequences encoding a polypeptide of interest and appropriate transcriptional and translational control elements. These methods include in vitro recombinant DNA techniques, synthetic techniques, and in vivo genetic recombination. Such techniques are described, for example, in Amalfitano et al., 1998 J. Virol. 72:926-933; Hodges, et al., 2000 J Gene Med 2:250-259; Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of vector/host systems may be utilized to contain and produce polynucleotide sequences. These include, but are not limited to, microorganisms such as bacteria transformed with recombinant bacteriophage, plasmid, or cosmid DNA vectors; yeast transformed with yeast vectors; insect cell systems infected with virus vectors (e.g., baculovirus); plant cell systems transformed with virus vectors (e.g., cauliflower mosaic virus, CaMV; tobacco mosaic virus, TMV) or with bacterial vectors (e.g., Ti or pBR322 plasmids); or animal cell systems.

The "control elements" or "regulatory sequences" present in an adenovirus vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, sequences encoding a polypeptide of interest may be ligated into an Ad transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125-162). Specific termination sequences, either for transcription or translation, may also be incorporated in order to achieve efficient translation of the sequence encoding the polypeptide of choice.

A variety of protocols for detecting and measuring the expression of polynucleotide-encoded products (e.g., target antigens of interest), using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211-1216).

The adenovirus vectors of the present invention comprise nucleic acid sequences encoding one or more antigens of interest, or variants or fragments thereof. The nucleic acid sequence may also contain a product that can be detected or selected for. As referred to herein, a "reporter" gene is one whose product can be detected, such as by fluorescence, enzyme activity on a chromogenic or fluorescent substrate, and the like or selected for by growth conditions. Such reporter genes include, without limitation, green fluorescent protein (GFP), β-galactosidase, chloramphenicol acetyltransferase (CAT), luciferase, neomycin phosphotransferase, secreted alkaline phosphatase (SEAP), and human growth hormone (HGH). Selectable markers include drug resistances, such as neomycin (G418), hygromycin, and the like.

The nucleic acid encoding an antigen of interest may also comprise a promoter or expression control sequence. This is a nucleic acid sequence that controls expression of the nucleic acid sequence encoding a target antigen and generally is active or activatable in the targeted cell. The choice of the promoter will depend in part upon the targeted cell type and the degree or type of control desired. Promoters that are suitable within the context of the present invention include, without limitation, constitutive, inducible, tissue specific, cell type specific, temporal specific, or event-specific.

Examples of constitutive or nonspecific promoters include the SV40 early promoter (U.S. Pat. No. 5,118,627), the SV40 late promoter (U.S. Pat. No. 5,118,627), CMV early gene promoter (U.S. Pat. No. 5,168,062), bovine papilloma virus promoter, and adenovirus promoter. In addition to viral promoters, cellular promoters are also amenable within the context of this invention. In particular, cellular promoters for the so-called housekeeping genes are useful (e.g., β-actin). Viral promoters are generally stronger promoters than cellular promoters.

Inducible promoters may also be used. These promoters include MMTV LTR (PCT WO 91/13160), inducible by dexamethasone, metallothionein, inducible by heavy metals, and promoters with cAMP response elements, inducible by cAMP, heat shock, promoter. By using an inducible promoter, the nucleic acid may be delivered to a cell and will remain quiescent until the addition of the inducer. This allows further control on the timing of production of the protein of interest.

Event-type specific promoters are active or upregulated only upon the occurrence of an event, such as tumorigenicity or viral infection, for example. The HIV LTR is a well-known example of an event-specific promoter. The promoter is inactive unless the tat gene product is present, which occurs upon viral infection. Some event-type promoters are also tissue-specific. Preferred event-type specific promoters include promoters activated upon viral infection.

Examples of promoters discussed herein include, but are not limited to, promoters for alphafetoprotein, alpha actin, myo D, carcinoembryonic antigen, VEGF-receptor (GenBank Accession No. X89776); FGF receptor; TEK or tie 2 (GenBank Accession No. L06139); tie (GenBank Accession Nos. X60954; S89716); urokinase receptor (GenBank Accession No. S78532); E- and P-selectins (GenBank Accession Nos. M64485; L01874); VCAM-1 (GenBank Accession No. M92431); endoglin (GenBank Accession No. HSENDOG); endosialin (Rettig et al., PNAS 89:10832, 1992); alpha V-beta3 integrin (Villa-Garcia et al., Blood 3:668, 1994; Donahue et al., BBA 1219:228, 1994); endothelin-1 (GenBank Accession Nos. M25377; J04819; J05489); ICAM-3 (GenBank Accession No. S50015); E9 antigen (Wang et al., Int. J. Cancer 54:363, 1993); von Willebrand factor (GenBank Accession Nos. HUMVWFI; HUMVWFA); CD44 (GenBank Accession No. HUMCD44B); CD40 (GenBank Accession Nos. HACD40L; HSCD405FR); vascular-endothelial cadherin (Martin-Padura et al., J. Pathol. 175:51, 1995); notch 4 (Uyttendaele et al., Development 122:2251, 1996) high molecular weight melanoma-associated antigen; prostate specific antigen-1, probasin, FGF receptor, VEGF receptor, erb B2; erb B3; erb B4; MUC-1; HSP-27; int-1; int-2, CEA, HBEGF receptor; EGF receptor; tyrosinase, MAGE, IL-2 receptor; prostatic acid phosphatase, probasin, prostate specific membrane antigen, alpha-crystallin, PDGF receptor, integrin receptor, α-actin, SM1 and SM2 myosin heavy chains, calponin-h1, SM22 alpha angiotensin receptor, IL-1, IL-2, IL-3, IL-4, IL-5, IL-6, IL-7, IL-8, IL-9, IL-10, IL-11, IL-12, IL-13, IL-14, immunoglobulin heavy chain, immunoglobulin light chain, CD4, and the like are useful within the context of this invention.

In addition to the promoter, repressor sequences, negative regulators, or tissue-specific silencers may be inserted to reduce non-specific expression of the polynucleotide. Multiple repressor elements may be inserted in the promoter region. Repression of transcription is independent of the orientation of repressor elements or distance from the promoter. One type of repressor sequence is an insulator sequence. Such sequences inhibit transcription (Dunaway et al., Mol Cell Biol 17: 182-9, 1997; Gdula et al., Proc Natl Acad Sci USA 93:9378-83, 1996, Chan et al., J Virol 70: 5312-28, 1996; Scott and Geyer, EMBO J. 14: 6258-67, 1995; Kalos and Fournier, Mol Cell Biol 15: 198-207, 1995; Chung et al., Cell 74: 505-14, 1993) and will silence background transcription.

Negative regulatory elements have been characterized in the promoter regions of a number of different genes. The repressor element functions as a repressor of transcription in the absence of factors, such as steroids, as does the NSE in the promoter region of the ovalbumin gene (Haecker et al., Mol. Endocrinology. 9:1113-1126, 1995). These negative regulatory elements bind specific protein complexes from oviduct, none of which are sensitive to steroids. Three different elements are located in the promoter of the ovalbumin gene. Oligonucleotides corresponding to portions of these elements repress viral transcription of the TK reporter. One of the silencer elements shares sequence identity with silencers in other genes (TCTCTCCNA).

Repressor elements have also been identified in the promoter region of a variety of genes, including the collagen II gene, for example. Gel retardation studies showed that nuclear factors from HeLa cells bind specifically to DNA fragments containing the silencer region, whereas chondrocyte nuclear extracts did not show any binding activity (Savanger et al., J. Biol. Chem. 265(12):6669-6674, 1990). Repressor elements have also been shown to regulate transcription in the carbamyl phosphate synthetase gene (Goping et al., Nucleic Acid Research 23(10):1717-1721, 1995). This gene is expressed in only two different cell types, hepatocytes and epithelial cells of the intestinal mucosa. Negative regulatory regions have also been identified in the promoter region of the choline acetyltransferase gene, the albumin promoter (Hu et al., J. Cell Growth Differ. 3(9):577-588, 1992), phosphoglycerate kinase (PGK-2) gene promoter (Misuno et al., Gene 119(2):293-297, 1992), and in the 6-phosphofructo-2-kinase/fructose-2, 6-bisphosphatase gene, in which the negative regulatory element inhibits transcription in non-hepatic cell lines (Lemaigre et al., Mol. Cell. Biol. 11(2):1099-1106). Furthermore, the negative regulatory element Tse-1 has been identified in a number of liver specific genes, including tyrosine aminotransferase (TAT). TAT gene expression is liver specific and inducible by both glucocorticoids and the cAMP signaling pathway. The cAMP response element (CRE) has been shown to be the target for repression by Tse-1 and hepatocyte-specific elements (Boshart et al., Cell 61(5): 905-916, 1990). Accordingly, it is clear that varieties of such elements are known or are readily identified.

In certain embodiments, elements that increase the expression of the desired target antigen are incorporated into the nucleic acid sequence of the adenovirus vectors described herein. Such elements include internal ribosome binding sites (IRES; Wang and Siddiqui, Curr. Top. Microbiol. Immunol 203:99, 1995; Ehrenfeld and Semler, Curr. Top. Microbiol. Immunol. 203:65, 1995; Rees et al., Biotechniques 20:102, 1996; Sugimoto et al., Biotechnology 12:694, 1994). IRES increase translation efficiency. As well, other sequences may enhance expression. For some genes, sequences especially at the 5' end inhibit transcription and/or translation. These sequences are usually palindromes that can form hairpin structures. Any such sequences in the nucleic acid to be delivered are generally deleted. Expression levels of the transcript or translated product are assayed to confirm or ascertain which sequences affect expression. Transcript levels may be assayed by any known method, including Northern blot hybridization, RNase probe protection and the like. Protein levels may be assayed by any known method, including ELISA.

As would be recognized by the skilled artisan, the adenovirus vectors of the present invention comprising heterologous nucleic acid sequences can be generated using recombinant techniques known in the art, such as those described in Maione et al., 2001 Proc Natl Acad Sci USA, 98:5986-5991; Maione et al., 2000 Hum Gene Ther 11:859-868; Sandig et al. 2000 Proc Natl Acad Sci USA, 97:1002-1007; Harui et al. 2004 Gene Therapy, 11:1617-1626; Parks et al., 1996 Proc Natl Acad Sci USA, 93:13565-13570; DelloRusso et al., 2002 Proc Natl Acad Sci USA, 99:12979-12984; Current Protocols in Molecular Biology, John Wiley and Sons, NY, N.Y.).

As noted above, the adenovirus vectors of the present invention comprise nucleic acid sequences that encode one or more target proteins or antigens of interest. In this regard, the vectors may contain nucleic acid encoding 1, 2, 3, 4, 5, 6, 7, 8, 9, 10, 11, 12, 13, 14, 15, 16, 17, 18, 19, 20 or more different target antigens of interest. The target antigens may be a full length protein or may be a fragment (e.g., an epitope) thereof. The adenovirus vectors may contain nucleic acid sequences encoding multiple fragments or epitopes from one target protein of interest or may contain one or more fragments or epitopes from numerous different target proteins of interest.

The term "target antigen" or "target protein" as used herein refers to a molecule, such as a protein, against which an immune response is to be directed. The target antigen may comprise any substance against which it is desirable to generate an immune response but generally, the target antigen is a protein. A target antigen may comprise a full length protein or a fragment thereof that induces an immune response (i.e., an immunogenic fragment). A target antigen or fragment thereof may be modified, e.g., to reduce one or more biological activities of the target antigen or to enhance its immunogenicity.

An "immunogenic fragment," as used herein is a fragment of a polypeptide that is specifically recognized (i.e., specifically bound) by a B-cell and/or T-cell surface antigen receptor resulting in the generation of an immune response specifically against the fragment. In certain embodiments, immunogenic fragments bind to an MHC class I or class II molecule. As used herein, an immunogenic fragment is said to "bind to" an MHC class I or class II molecule if such binding is detectable using any assay known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., J. Immunol. 152:163, 1994). Alternatively, functional peptide competition assays that are known in the art may be employed. Immunogenic fragments of polypeptides may generally be identified using well known techniques, such as those summarized in Paul, Fundamental Immunology, 3rd ed., 243-247 (Raven Press, 1993) and references cited therein. Representative techniques for identifying immunogenic fragments include screening polypeptides for the ability to react with antigen-specific antisera and/or T-cell lines or clones. An immunogenic fragment of a particular target polypeptide is a fragment that reacts with such antisera and/or T-cells at a level that is not substantially less than the reactivity of the full length target polypeptide (e.g., in an ELISA and/or T-cell reactivity assay). In other words, an immunogenic fragment may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988.

Target antigens of the present invention include but are not limited to antigens derived from any of a variety of infectious agents or cancer cells. As used herein, an "infectious agent" is any living organism capable of infecting a host and "cancer" means a neoplastic cell. Infectious agents include, for example, bacteria, any variety of viruses, such as, single stranded RNA viruses, single stranded DNA viruses, fungi, parasites, and protozoa. Examples of infectious agents include, but are not limited to, *Actinobacillus* spp., *Actinomyces* spp., Adenovirus (types 1, 2, 3, 4, 5 et 7), Adenovirus (types 40 and 41), *Aerococcus* spp., *Aeromonas hydrophila, Ancylostoma duodenale, Angiostrongylus cantonensis, Ascaris lumbricoides, Ascaris* spp., *Aspergillus* spp., *Babesia* spp, *B. microti, Bacillus anthracis, Bacillus cereus, Bacteroides* spp., *Balantidium coli, Bartonella bacilliformis, Blastomyces dermatitidis*, Bluetongue virus, *Bordetella bronchiseptica, Bordetella pertussis, Borrelia afzelii, Borrelia burgdorferi, Borrelia garinii, Branhamella catarrhalis, Brucella* spp. (*B. abortus, B. canis, B. melitensis, B. suis*), *Brugia* spp., *Burkholderia, (Pseudomonas) mallei, Burkholderia (Pseudomonas) pseudomallei*, California serogroup, *Campylobacter fetus* subsp. *Fetus, Campylobacter jejuni, C. coli, C. fetus* subsp. *Jejuni, Candida albicans, Capnocytophaga* spp., Chikungunya virus, *Chlamydia psittaci, Chlamydia trachomatis, Citrobacter* spp., *Clonorchis sinensis, Clostridium botulinum, Clostridium difficile, Clostridium perfringens, Clostridium tetani, Clostridium* spp. (with the exception of those species listed above), *Coccidioides immitis*, Colorado tick fever virus, *Corynebacterium diphtheriae, Coxiella burnetii*, Coxsackievirus, Creutzfeldt-Jakob agent, Kuru agent, Crimean-Congo hemorrhagic fever virus, *Cryptococcus neoformans, Cryptosporidium parvum*, Cytomegalovirus, *Cyclospora cayatanesis*, Dengue virus (1, 2, 3, 4), Diphtheroids, Eastern (Western) equine encephalitis virus, Ebola virus, *Echinococcus granulosus, Echinococcus multilocularis*, Echovirus, *Edwardsiella tarda, Entamoeba histolytica, Enterobacter* spp., Enterovirus 70, *Epidermophyton floccosum, Ehrlichia* spp, *Ehrlichia sennetsu, Microsporum* spp. *Trichophyton* spp., Epstein-Barr virus, *Escherichia coli*, enterohemorrhagic, *Escherichia coli*, enteroinvasive, *Escherichia coli*, enteropathogenic, *Escherichia coli*, enterotoxigenic, *Fasciola hepatica, Francisella tularensis, Fusobacterium* spp., *Gemella haemolysans, Giardia lamblia*, Guanarito virus, *Haemophilus ducreyi, Haemophilus influenzae* (group b), Hantavirus, Hepatitis A virus, Hepatitis B virus, Hepatitis C virus, Hepatitis D virus, Hepatitis E virus, Herpes simplex virus, Herpesvirus simiae, Histoplasma capsulatum, Human coronavirus, Human immunodeficiency virus, Human papillomavirus, Human rotavirus, Human T-lymphotrophic virus, Influenza virus including H5N1, Junin virus/Machupo virus, *Klebsiella* spp., Kyasanur Forest disease virus, *Lactobacillus* spp., Lassa virus, *Legionella pneumophila, Leishmania major, Leishmania infantum, Leishmania* spp., *Leptospira interrogans, Listeria monocytogenes*, Lymphocytic choriomeningitis virus, Machupo virus, Marburg virus, Measles virus, *Micrococcus* spp., *Moraxella* spp., *Mycobacterium* spp. (other than *M. bovis, M. tuberculosis, M. avium, M. leprae*), *Mycobacterium tuberculosis, M. bovis, Mycoplasma hominis, M. orale, M. salivarium, M. fermentans, Mycoplasma pneumoniae, Naegleria fowleri, Necator americanus, Neisseria gonorrhoeae, Neisseria meningitides, Neisseria* spp. (other than *N. gonorrhoeae* and *N. meningitidis*), *Nocardia* spp., Norwalk virus, Omsk hemorrhagic fever virus, *Onchocerca volvulus, Opisthorchis* spp., Parvovirus B19, *Pasteurella* spp., *Peptococcus* spp., *Peptostreptococcus* spp., *Plasmodium falciparum, Plasmodium vivax, Plasmodium* spp., *Plesiomonas shigelloides*, Powassan encephalitis virus, *Proteus* spp., *Pseudomonas* spp. (other than *P. mallei, P. pseudomallei*), Rabies virus, Respiratory syncytial virus, Rhinovirus, *Rickettsia akari, Rickettsia prowazekii, R. Canada, Rickettsia rickettsii*, Rift Valley virus, Ross river virus/O'Nyong-Nyong virus, Rubella virus, *Salmonella choleraesuis, Salmonella paratyphi, Salmonella typhi, Salmonella* spp. (with the exception of those species listed above), *Schistosoma* spp., Scrapie agent, *Serratia* spp., *Shigella* spp., Sindbis virus, *Sporothrix schenckii*, St. Louis encephalitis virus, Murray Valley encephalitis virus, *Staphylococcus aureus, Streptobacillus moniliformis, Streptococcus agalactiae, Streptococcus faecalis, Streptococcus pneumoniae, Streptococcus pyogenes, Streptococcus salivarius, Taenia saginata, Taenia solium, Toxocara canis, T. cati, T. cruzi, Toxoplasma gondii, Treponema pallidum, Trichinella* spp., *Trichomonas vaginalis, Trichuris trichiura, Trypanosoma brucei, Trypanosoma cruzi, Ureaplasma urealyticum*, Vaccinia virus, Varicella-zoster virus, eastern equine encephalitis virus (EEEV), severe acute respiratory virus (SARS), Venezuelan equine encephalitis virus (VEEV), Vesicular stomatitis virus, *Vibrio cholerae*, serovar 01, *Vibrio parahaemolyticus*, West Nile virus, *Wuchereria bancrofti*, Yellow fever virus, *Yersinia enterocolitica, Yersinia pseudotuberculosis*, and *Yersinia pestis*.

Examples of infectious agents associated with human malignancies include Epstein-Barr virus, *Helicobacter pylori*, Hepatitis B virus, Hepatitis C virus, Human heresvirus-8, Human immunodeficiency virus, Human papillomavirus, Human T cell leukemia virus, liver flukes, and *Schistosoma haematobium*.

A number of viruses are associated with viral hemorrhagic fever, including filoviruses (e.g., Ebola, Marburg, and Reston), arenaviruses (e.g. Lassa, Junin, and Machupo), and bunyaviruses. In addition, phleboviruses, including, for example, Rift Valley fever virus, have been identified as etiologic agents of viral hemorrhagic fever. Etiological agents of hemorrhagic fever and associated inflammation may also include paramyxoviruses, particularly respiratory syncytial virus (Feldmann, H. et al. (1993) *Arch Virol Suppl.* 7:81-100). In addition, other viruses causing hemorrhagic fevers in man have been identified as belonging to the following virus groups: togavirus (Chikungunya), flavivirus (dengue, yellow fever, Kyasanur Forest disease, Omsk hemorrhagic fever), nairovirus (Crimian-Congo hemorrhagic fever) and hantavirus (hemorrhagic fever with renal syndrome, nephropathic epidemia). Furthermore, Sin Nombre virus was identified as the etiologic agent of the 1993 outbreak of hantavirus pulmonary syndrome in the American Southwest.

Target antigens may include proteins, or variants or fragments thereof, produced by any of the infectious organisms described herein, such as, but not limited to, viral coat proteins, i.e., influenza neuraminidase and hemagglutinin, HIV gp160 or derivatives thereof, HIV Gag, HIV Nef, HIV Pol, SARS coat proteins, herpes virion proteins, WNV proteins, etc. Target antigens may also include bacterial surface proteins including pneumococcal PsaA, PspA, LytA, surface or virulence associated proteins of bacterial pathogens such as *Nisseria gonnorhea*, outer membrane proteins or surface proteases.

Target antigens may also include proteins, or variants or fragments thereof, of infectious agents associated with human malignancies such as the human papillomavirus (HPV) oncoproteins E6 and E7. In certain embodiments, the oncoprotein may be modified to produce a non-oncogenic variant or a variant having reduced oncogenicity relative to the wild type protein. For example, the portion of the peptide that is responsible for binding a tumor suppressor protein (e.g., p53 and pRb) may be deleted or modified so that it no longer interacts with the tumor suppressor protein. As another example, an oncoprotein that is a kinase, such as Her2/neu, may be kinase-inactivated, e.g., by point mutation. In some instances, two or more target antigens may be used during immunization. For example, the E6 and E7 antigens can be combined in a fusion protein, or separate vectors containing heterologous nucleotides encoding the modified or unmodified E6 and E7 target antigens are used in combination. For example, an Ad5-E6 vector can be administered with an Ad5-E7 vector. In this example, the Ad5-E6 vector and Ad5-E7 vector may be administered simultaneously or they may be administered sequentially.

Target antigens of the present invention include but are not limited to antigens derived from a variety of tumor proteins. Illustrative tumor proteins useful in the present invention include, but are not limited to any one or more of, WT1, HPV E6, HPV E7, p53, MAGE-A1, MAGE-A2, MAGE-A3, MAGE-A4, MAGE-A6, MAGE-A10, MAGE-A12, BAGE, DAM-6, -10, GAGE-1, -2, -8, GAGE-3, -4, -5, -6, -7B, NA88-A, NY-ESO-1, MART-1, MC1R, Gp100, PSA, PSM, Tyrosinase, TRP-1, TRP-2, ART-4, CAMEL, CEA, Cyp-B, Her2/neu, BRCA1, hTERT, hTRT, iCE, MUC1, MUC2, PRAME, P15, RU1, RU2, SART-1, SART-3, WT1, AFP, β-catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, ETV6/AML, LDLR/FUT, Pml/RARα, and TEL/AML1. These and other tumor proteins are known to the skilled artisan.

In certain embodiments tumor antigens may be identified directly from an individual with cancer. In this regard, screens can be carried out using a variety of known technologies. For example, in one embodiment, a tumor biopsy is taken from a patient, RNA is isolated from the tumor cells and screened using a gene chip (for example, from Affymetrix, Santa Clara, Calif.) and a tumor antigen is identified. Once the tumor target antigen is identified, it may then be cloned, expressed and purified using techniques known in the art. This target molecule is then linked to one or more epitopes/cassettes of the present invention as described herein and administered to the cancer patient in order to alter the immune response to the target molecule isolated from the tumor. In this manner, "personalized vaccines" are contemplated within the context of the invention. In certain embodiments, cancers may include carcinomas or sarcomas.

The adenovirus vectors of the present invention may also include nucleic acid sequences that encode proteins that increase the immunogenicity of the target antigen. In this regard, the protein produced following immunization with the adenovirus vector containing such a protein may be a fusion protein comprising the target antigen of interest fused to a protein that increases the immunogenicity of the target antigen of interest.

In one embodiment, such an "immunological fusion partner" is derived from a *Mycobacterium* sp., such as a *Mycobacterium tuberculosis*-derived Ra12 fragment. Ra12 compositions and methods for their use in enhancing the expression and/or immunogenicity of heterologous polynucleotide/polypeptide sequences are described in U.S. Patent Application 60/158,585. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. Patent Application 60/158, 585; see also, Skeiky et al., *Infection and Immun.* 67:3998-4007 (1999), incorporated herein by reference). C-terminal fragments of the MTB32A coding sequence express at high levels and remain as soluble polypeptides throughout the purification process. Moreover, Ra12 may enhance the immunogenicity of heterologous immunogenic polypeptides with which it is fused. One Ra12 fusion polypeptide comprises a 14 KD C-terminal fragment corresponding to amino acid residues 192 to 323 of MTB32A. Other Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within another embodiment, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemagglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798, 1992). Within another embodiment, a repeat portion of LYTA may be incorporated into a fusion polypeptide. A repeat portion is found in the C-terminal region starting at residue 178. One particular repeat portion incorporates residues 188-305.

Methods of Use

The adenovirus vectors of the present invention can be used in a number of vaccine settings for generating an immune response against one or more target antigens as described herein. The adenovirus vectors are of particular importance because of the unexpected finding that they can be used to generate immune responses in subjects who have preexisting immunity to Ad and can be used in vaccination regimens that include multiple rounds of immunization using the adenovirus vectors, regimens not possible using previous generation adenovirus vectors.

Generally, generating an immune response comprises an induction of a humoral response and/or a cell-mediated response. In certain embodiments, it is desirable to increase an immune response against a target antigen of interest. In certain circumstances, generating an immune response may involve a decrease in the activity and/or number of certain cells of the immune system or a decrease in the level and/or activity of certain cytokines or other effector molecules. As such "generating an immune response" or "inducing an immune response" comprises any statistically significant change, e.g. increase or decrease, in the number of one or more immune cells (T cells, B cells, antigen-presenting cells, dendritic cells, neutrophils, and the like) or in the activity of one or more of these immune cells (CTL activity, HTL activity, cytokine secretion, change in profile of cytokine secretion, etc.).

The skilled artisan would readily appreciate that a number of methods for establishing whether an alteration in the immune response has taken place are available. A variety of methods for detecting alterations in an immune response (e.g. cell numbers, cytokine expression, cell activity) are known in the art and are useful in the context of the instant invention. Illustrative methods are described in *Current Protocols in Immunology*, Edited by: John E. Coligan, Ada M. Kruisbeek, David H. Margulies, Ethan M. Shevach, Warren Strober (2001 John Wiley & Sons, NY, N.Y.) Ausubel et al. (2001 *Current Protocols in Molecular Biology*, Greene Publ. Assoc. Inc. & John Wiley & Sons, Inc., NY, N.Y.); Sambrook et al. (1989 *Molecular Cloning*, Second Ed., Cold Spring Harbor Laboratory, Plainview, N.Y.); Maniatis et al. (1982 Molecular Cloning, Cold Spring Harbor Laboratory, Plainview, N.Y.) and elsewhere. Illustrative methods useful in this context include intracellular cytokine staining (ICS), ELISpot, proliferation assays, cytotoxic T cell assays including chromium release or equivalent assays, and gene expression analysis using any number of polymerase chain reaction (PCR) or RT-PCR based assays.

In certain embodiments, generating an immune response comprises an increase in target antigen-specific CTL activity of between 1.5 and 5 fold in a subject administered the adenovirus vectors of the invention as compared to a control. In another embodiment, generating an immune response comprises an increase in target-specific CTL activity of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold in a subject administered the adenovirus vectors as compared to a control.

In a further embodiment, generating an immune response comprises an increase in target antigen-specific HTL activity, such as proliferation of helper T cells, of between 1.5 and 5 fold in a subject administered the adenovirus vectors of the invention that comprise nucleic acid encoding the target antigen as compared to an appropriate control. In another embodiment, generating an immune response comprises an increase in target-specific HTL activity of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold as compared to a control. In this context, HTL activity may comprise an increase as described above, or decrease, in production of a particular cytokine, such as interferon-gamma (IFN-$\gamma$), interleukin-1 (IL-1), IL-2, IL-3, IL-6, IL-7, IL-12, IL-15, tumor necrosis factor-alpha (TNF-$\alpha$), granulocyte macrophage colony-stimulating factor (GM-CSF), granulocyte-colony stimulating factor (G-CSF), or other cytokine. In this regard, generating an immune response may comprise a shift from a Th2 type response to a Th1 type response or in certain embodiments a shift from a Th1 type response to a Th2 type response. In other embodiments, generating an immune response may comprise the stimulation of a predominantly Th1 or a Th2 type response.

In a further embodiment, generating an immune response comprises an increase in target-specific antibody production of between 1.5 and 5 fold in a subject administered the adenovirus vectors of the present invention as compared to an appropriate control. In another embodiment, generating an immune response comprises an increase in target-specific antibody production of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold in a subject administered the adenovirus vector as compared to a control.

Thus the present invention provides methods for generating an immune response against a target antigen of interest comprising administering to the individual an adenovirus vector comprising: a) a replication defective adenovirus vector, wherein the adenovirus vector has a deletion in the E2b region, and b) a nucleic acid encoding the target antigen; and readministering the adenovirus vector at least once to the individual; thereby generating an immune response against the target antigen. In certain embodiments, the present invention provides methods wherein the vector administered is not a gutted vector. In particular embodiments, the target antigen may be a wild-type protein, or a fragment or variant thereof.

In a further embodiment, the present invention provides methods for generating an immune response against a target antigen in an individual, wherein the individual has preexisting immunity to Ad, by administering to the individual an adenovirus vector comprising: a) a replication defective adenovirus vector, wherein the adenovirus vector has a deletion in the E2b region, and b) a nucleic acid encoding the target antigen; and readministering the adenovirus vector at least once to the individual; thereby generating an immune response against the target antigen. In particular embodiments, the target antigen may be a wild-type protein, or a fragment or variant thereof.

With regard to preexisting immunity to Ad, this can be determined using methods known in the art, such as antibody-based assays to test for the presence of Ad antibodies. Further, in certain embodiments, the methods of the present invention include first determining that an individual has preexisting immunity to Ad then administering the E2b deleted adenovirus vectors of the invention as described herein.

One embodiment of the invention provides a method of generating an immune response against one or more target antigens in an individual comprising administering to the individual a first adenovirus vector comprising a replication defective adenovirus vector, wherein the adenovirus vector has a deletion in the E2b region, and a nucleic acid encoding at least one target antigen; administering to the individual a second adenovirus vector comprising a replication defective adenovirus vector, wherein the adenovirus vector has a deletion in the E2b region, and a nucleic acid encoding at least one target antigen, wherein the at least one target antigen of the second adenovirus vector is the same or different from the at least one target antigen of the first adenovirus vector. In particular embodiments, the target antigen may be a wild-type protein, or a fragment or variant thereof.

Thus, the present invention contemplates multiple immunizations with the same E2b deleted adenovirus vector or multiple immunizations with different E2b deleted adenovirus vectors. In each case, the adenovirus vectors may comprise nucleic acid sequences that encode one or more target antigens as described elsewhere herein. In certain embodiments, the methods comprise multiple immunizations with an E2b deleted adenovirus encoding one target antigen, and re-administration of the same adenovirus vector multiple times, thereby inducing an immune response against the target antigen.

In a further embodiment, the methods comprise immunization with a first adenovirus vector that encodes one or more target antigens, and then administration with a second adenovirus vector that encodes one or more target antigens that may be the same or different from those antigens encoded by the first adenovirus vector. In this regard, one of the encoded target antigens may be different or all of the encoded antigens may be different, or some may be the same and some may be different. Further, in certain embodiments, the methods include administering the first adenovirus vector multiple times and administering the second adenovirus multiple times. In this regard, the methods comprise administering the first adenovirus vector 1, 2, 3, 4, 5, 6, 7, 8, 9, 10, 11, 12, 13, 14, 15, or more times and administering the second adenovirus vector 1, 2, 3, 4, 5, 6, 7, 8, 9, 10, 11, 12, 13, 14, 15, or more times. The order of administration may comprise administering the first adenovirus one or multiple times in a row followed by administering the second adenovirus vector one or multiple times in a row. In certain embodiments, the methods include alternating administration of the first and the second adenovirus vectors as one administration each, two administrations each, three administrations each, and so on. In certain embodiments, the first and the second adenovirus vectors are administered simultaneously. In other embodiments, the first and the second adenovirus vectors are administered sequentially.

As would be readily understood by the skilled artisan, more than two adenovirus vectors may be used in the methods of the present invention. Three, 4, 5, 6, 7, 8, 9, 10 or more different adenovirus vectors may be used in the methods of the invention. In certain embodiments, the methods comprise administering more than one E2b deleted adenovirus vector at a time. In this regard, immune responses against multiple target antigens of interest can be generated by administering multiple different adenovirus vectors simultaneously, each comprising nucleic acid sequences encoding one or more antigens.

The present invention provides methods of generating an immune response against any target antigen, such as those described elsewhere herein.

The present invention provides methods of generating an immune response against any infectious agent, such as those described elsewhere herein.

As noted elsewhere herein, the adenovirus vectors of the invention comprise nucleic acid sequences that encode one or more target antigens of interest from any one or more of the infectious agents against which an immune response is to be generated. For example, target antigens may include, but are not limited to, viral coat proteins, i.e., influenza neuraminidase and hemagglutinin, HIV gp160, p24, gp120, gp41, envelope, protease, or reverse transcriptase, or derivatives of any of these viral proteins; SARS coat proteins, herpes virion proteins, WNV proteins, etc. Target antigens may also include bacterial surface proteins including pneumococcal PsaA, PspA, LytA, surface or virulence associated proteins of bacterial pathogens such as *Nisseria gonnorhea*, outer membrane proteins or surface proteases. In particular embodiments, the target antigen may be a wild-type protein, or a fragment or variant thereof.

In certain embodiments, the adenovirus vectors are used to generate an immune response against a cancer. In this regard, the methods include generating an immune response against carcinomas or sarcomas such as solid tumors, lymphomas or leukemias. Thus, the adenovirus vectors described herein are used to generate an immune response against a cancer including but not limited to carcinomas or sarcomas such as neurologic cancers, melanoma, non-Hodgkin's lymphoma, Hodgkin's disease, leukemias, plasmocytomas, adenomas, gliomas, thymomas, breast cancer, prostate cancer, colo-rectal cancer, kidney cancer, renal cell carcinoma, uterine cancer, pancreatic cancer, esophageal cancer, lung cancer, ovarian cancer, cervical cancer, testicular cancer, gastric cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers.

Further, in this regard, the cancer target antigens may include but are not limited to antigens derived from a variety of tumor proteins. Illustrative tumor proteins useful in the present invention include, but are not limited to any one or more of, p53, HPV E6, HPV E7, MAGE-A1, MAGE-A2, MAGE-A3, MAGE-A4, MAGE-A6, MAGE-A10, MAGE-A12, BAGE, DAM-6, -10, GAGE-1, -2, -8, GAGE-3, -4, -5, -6, -7B, NA88-A, NY-ESO-1, MART-1, MC1R, Gp100, PSA, PSM, Tyrosinase, TRP-1, TRP-2, ART-4, CAMEL, CEA, Cyp-B, Her2/neu, hTERT, hTRT, iCE, MUC1, MUC2, PRAME, P15, RU1, RU2, SART-1, SART-3, WT1, AFP, β-catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, ETV6/AML, LDLR/FUT, Pml/RARα, and TEL/AML1. These and other tumor proteins are known to the skilled artisan.

Methods are also provided for treating or ameliorating the symptoms of any of the infectious diseases or cancers as described herein. The methods of treatment comprise administering the adenovirus vectors one or more times to individuals suffering from or at risk from suffering from an infectious disease or cancer as described herein. As such, the present invention provides methods for vaccinating against infectious diseases or cancers in individuals who are at risk of developing such a disease. Individuals at risk may be individuals who may be exposed to an infectious agent at some time or have been previously exposed but do not yet have symptoms of infection or individuals having a genetic predisposition to developing a cancer or being particularly susceptible to an infectious agent.

The present invention contemplates the use of adenovirus vectors for the in vivo delivery of nucleic acids encoding a target antigen, or a fragment or variant thereof. Once injected into a subject, the nucleic acid sequence is expressed resulting in an immune response against the antigen coded for by the sequence. The adenovirus vector vaccine is administered in an "effective amount", that is, an amount of adenovirus vector that is effective in a selected route or routes of administration to elicit an immune response as described elsewhere herein. In certain embodiments, an effective amount is one that induces an immune response effective to facilitate protection or treatment of the host against the target infectious agent or cancer. The amount of vector in each vaccine dose is selected as an amount which induces an immune, immunoprotective or other immunotherapeutic response without significant adverse effects generally associated with typical vaccines. Once vaccinated, subjects may be monitored to determine the efficacy of the vaccine treatment. Monitoring the efficacy of vaccination may be performed by any method known to a person of ordinary skill in the art. In some embodiments, blood or fluid samples may be assayed to detect levels of antibodies. In other embodiments, ELISpot assays may be performed to detect a cell-mediated immune response from circulating blood cells or from lymphoid tissue cells.

The adenovirus vectors of the invention are generally prepared as known in the art (see e.g., Hodges et al., 2000 supra; or Amalfitano et al., 1998 supra). For example, in certain embodiments, tissue culture plates containing E.C7 or C-7 cells are infected with the adenovirus vector virus stocks at an appropriate MOI (e.g., 5) and incubated at 37.0° C. for 40 h. The infected cells are harvested, resuspended in an appropriate buffer such as 10 mM Tris-Cl (pH 8.0), and sonicated, and the virus is purified by two rounds of cesium chloride density centrifugation. In certain techniques, the virus containing band is desalted over a Sephadex CL-6B column (Pharmacia Biotech, Piscataway, N.J.), glycerol is added to a concentration of 12%, and aliquots are stored at –80° C. The titer of the stock is measured (e.g., by measurement of the optical density at 260 nm of an aliquot of the virus after SDS lysis). GMP procedures for producing appropriate Ad stocks for human administration are used where appropriate.

For administration, the adenovirus vector stock is combined with an appropriate buffer, physiologically acceptable carrier, excipient or the like. In certain embodiments, an appropriate number of adenovirus vector particles are administered in an appropriate buffer, such as, sterile PBS. In certain circumstances it will be desirable to deliver the adenovirus vector compositions disclosed herein parenterally, intravenously, intramuscularly, or even intraperitoneally. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. In other embodiments, E2b deleted adenovirus vectors may be delivered in pill form, delivered by swallowing or by suppository.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria, molds and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the adenovirus vectors of the invention may be administered in conjunction with one or more immunostimulants, such as an adjuvant. An immunostimulant refers to essentially any substance that enhances or potentiates an immune response (antibody and/or cell-mediated) to an antigen. One type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is preferably one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within certain embodiments, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145-173, 1989.

Certain illustrative adjuvants for eliciting a predominantly Th1-type response include, for example, a combination of monophosphoryl lipid A, preferably 3-de-O-acylated monophosphoryl lipid A, together with an aluminum salt. MPL® adjuvants are available from GlaxoSmithKlein (Research Triangle Park, N.C.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another adjuvant for use in the present invention comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other formulations may include more than one saponin in the adjuvant combinations of the present invention, for example combinations of at least two of the following group comprising QS21, QS7, Quil A, β-escin, or digitonin.

In certain embodiments, the compositions may be delivered by intranasal sprays, inhalation, and/or other aerosol delivery vehicles. The delivery of drugs using intranasal microparticle resins (Takenaga et al., J Controlled Release 1998 Mar. 2; 52(1-2):81-7) and lysophosphatidyl-glycerol compounds (U.S. Pat. No. 5,725,871) are well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 July; 16(7):307-21; Takakura, Nippon Rinsho 1998 March; 56(3):691-5; Chandran et al., Indian J Exp Biol. 1997 August; 35(8):801-9; Margalit, Crit. Rev Ther Drug Carrier Syst. 1995; 12(2-3):233-61; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J Biol. Chem. 1990 Sep. 25; 265(27):16337-42; Muller et al., DNA Cell Biol. 1990 April; 9(3):221-9). Liposomes have been used effectively to introduce genes, various drugs, radiotherapeutic agents, enzymes, viruses, transcription factors, allosteric effectors and the like, into a variety of cultured cell lines and animals. Furthermore, the use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December; 24(12):1113-28). To avoid side effects due to intracellular polymeric overloading, such ultrafine particles (sized around 0.1 µm) may be designed using polymers able to be degraded in vivo. Such particles can be made as described, for example, by Couvreur et al., Crit. Rev Ther Drug Carrier Syst. 1988; 5(1):1-20; zur Muhlen et al., Eur J Pharm Biopharm. 1998 March; 45(2): 149-55; Zambaux et al. J Controlled Release. 1998 Jan. 2; 50(1-3):31-40; and U.S. Pat. No. 5,145,684.

Routes and frequency of administration of the therapeutic compositions described herein, as well as dosage, will vary from individual to individual, and from disease to disease, and may be readily established using standard techniques. In general, the pharmaceutical compositions and vaccines may be administered by injection (e.g., intracutaneous, intramuscular, intravenous or subcutaneous), intranasally (e.g., by aspiration), in pill form (e.g. swallowing, suppository for vaginal or rectal delivery). In certain embodiments, between 1 and 10 doses may be administered over a 52 week period. In certain embodiments, 6 doses are administered, at intervals of 1 month, and further booster vaccinations may be given periodically thereafter. Alternate protocols may be appropriate for individual patients. As such, 1, 2, 3, 4, 5, 6, 7, 8, 9, 10, 11, 12, 13, 14, 15, 16, 17, 18, 19, 20, or more doses may be administered over a 1 year period or over shorter or longer periods, such as over 35, 40, 45, 50, 55, 60, 65, 70, 75, 80, 85, 90, 95 or 100 week periods. Doses may be administered at 1, 2, 3, 4, 5, or 6 week intervals or longer intervals.

A suitable dose is an amount of an adenovirus vector that, when administered as described above, is capable of promoting a target antigen immune response as described elsewhere herein. In certain embodiments, the immune response is at least 10-50% above the basal (i.e., untreated) level. Such response can be monitored by measuring the target antigen(s) antibodies in a patient or by vaccine-dependent generation of cytolytic effector cells capable of killing patient tumor or infected cells in vitro, or other methods known in the art for monitoring immune responses. Such vaccines should also be capable of causing an immune response that leads to an improved clinical outcome of the disease in question in vaccinated patients as compared to non-vaccinated patients.

In general, an appropriate dosage and treatment regimen provides the adenovirus vectors in an amount sufficient to provide therapeutic and/or prophylactic benefit. Such a response can be monitored by establishing an improved clinical outcome for the particular disease being treated in treated patients as compared to non-treated patients. Such improvements in clinical outcome would be readily recognized by a treating physician. Increases in preexisting immune responses to a target protein generally correlate with an improved clinical outcome. Such immune responses may generally be evaluated using standard proliferation, cytotoxicity or cytokine assays, which may be performed using samples obtained from a patient before and after treatment.

While one advantage of the present invention is the capability to administer multiple vaccinations with the same or different adenovirus vectors, particularly in individuals with preexisting immunity to Ad, the adenoviral vaccines of this invention may also be administered as part of a prime and boost regimen. A mixed modality priming and booster inoculation scheme may result in an enhanced immune response. Thus, one aspect of this invention is a method of priming a subject with a plasmid vaccine, such as a plasmid vector comprising a target antigen of interest, by administering the plasmid vaccine at least one time, allowing a predetermined length of time to pass, and then boosting by administering the adenovirus vector. Multiple primings, e.g., 1-4, may be employed, although more may be used. The length of time between priming and boost may typically vary from about four months to a year, but other time frames may be used. In certain embodiments, subjects may be primed four times with plasmid vaccines, and then boosted 4 months later with the adenovirus vector.

EXAMPLES

Example 1

Multiple Injections of Ad5Null Adenovirus Vector Produces Anti-Adenovirus Antibodies This example shows that multiple injections of Ad5-null results in the production of anti-adenovirus antibodies in the injected subjects It was demonstrated that the Ad5Null adenovirus vector that does not contain any heterologous nucleic acid sequences, generates a neutralizing immune response in mice. In particular, in one experiment, female Balb/c mice aged 5-7 weeks were immunized with Ad5Null viral particles at 14 day intervals. To determine the presence of anti-adenovirus antibodies, an enzyme linked immunosorbent assay (ELISA) was used. For this ELISA, $10^9$ viral particles were coated onto microtiter wells in 100 µL of 0.05M carbonate/bicarbonate buffer, pH 9.6, and incubated overnight at room temperature. For a standard immunoglobulin G (IgG) reference curve, 200 ng, 100 ng, 50 ng, 25 ng, and 0 ng of purified mouse IgG (Sigma Chemicals) were coated onto microtiter wells as described above. After incubation, all wells were washed 3 times with 250 µL of 1% bovine serum albumin (BSA) in phosphate buffered saline (PBS), pH 7.4. After washing, 250 µL of BSA/PBS was added to all and incubated for 30 minutes at room temperature to block unbound sites. After incubation, all wells were washed 3 times with 250 µL of BSA/PBS. After washing, 200 µL of a 1/100 serum dilution in BSA/PBS was added to wells and incubated for 1 hour at room temperature. For a positive control, 200 µL of a 1/10000 dilution of anti-adenovirus antiserum (Biodesign International) in BSA/PBS were added to wells. Control wells contained BSA/PBS only. After incubation, all wells were washed 3 times with 250 µL of BSA/PBS. After washing, 200 µL of a 1/10000 dilution of peroxidase conjugated gamma chain specific goat anti-mouse IgG (Sigma Chemicals) in BSA/PBS were added to each well and incubated for 1 hour at room temperature. After incubation, all wells were washed 3 times with 250 µL of BSA/PBS. After washing, 200 µL of developing reagent (0.5 mg/mL 1,2 phenylenediamine in 0.2M potassium phosphate buffer, pH 5.0, containing 0.06% hydrogen peroxide) was added to each well and incubated for 30-40 minutes at room temperature. After incubation, the color reaction was stopped by addition of 50 µL 5N HCl to each well. All wells were then read in a microwell plate reader at 492 nm. After readings were obtained, the optical density readings of unknown samples were correlated with the standard IgG curve to obtain the nanograms of IgG bound per well. This was performed using the INSTAT statistical package.

As shown in FIG. 1, significant levels (P<0.001) of anti-adenovirus IgG antibody were detected in mice 2 weeks after a first injection with $10^{10}$ Ad-5-null. A significantly higher level (P<0.001) was observed 2 weeks after a second injection with $10^{10}$ adenovirus. Significantly higher (P<0.001) levels of antibody were continued to be observed 2 weeks after a third injection with $10^{10}$ Ad5-null. Each value represents the average of triplicate determinations from pooled sera of 5 mice in each group. These results indicate that multiple injections of Ad5-null results in the production of anti-adenovirus antibodies in the injected subjects.

To determine the presence of neutralizing antibody to Ad, the following assay was utilized. A HEK-293T cell line was cultured in 200 µL of culture medium consisting of DMEM containing 10% fetal calf serum (DMEM/FCS) in microwell tissue culture plates at a cell concentration of $2 \times 10^3$ cells per well for 24 hours at 37 C in 5% $CO_2$. After incubation, 100 µL of culture medium was removed from triplicate wells and mixed with 20 µL of DMEM/FCS containing viral particles (VP). After mixing, the 120 µL mixture was added back to the respective microwells. In another set of triplicate wells, 100 µL of culture medium was removed and mixed with 20 µL of heat inactivated (56 C for 1 hour) Ad immune mouse serum previously incubated with VP for one hour at room temperature. After mixing, the 120 µL mixture was added back to the respective wells. In triplicate cell control wells, 20 µL of DMEM/FCS was added to control for total culture medium volume. Triplicate medium only control wells contained 220 µL of DMEM/FCS. The tissue culture plate was incubated for an additional 3 days at 37 C in 5% $CO_2$. After incubation, 40 µL of PROMEGA cell viability reagent (Owen's reagent) was added to all wells and incubated for 75 minutes at 37 C in 5% $CO_2$. In this assay, the Owen's reagent (MTS tetrazolium compound) is bioreduced by viable cells into a colored formazan product that is soluble in tissue culture medium. The quantity of formazan product as measured by absorbance at 490 nm is directly proportional to the number of living cells in culture. After incubation, 150 µL was removed from each well and transferred to another microwell plate for optical density readings. Optical density readings at 492 nm were subsequently obtained using a microwell plate reader.

Figure 2:
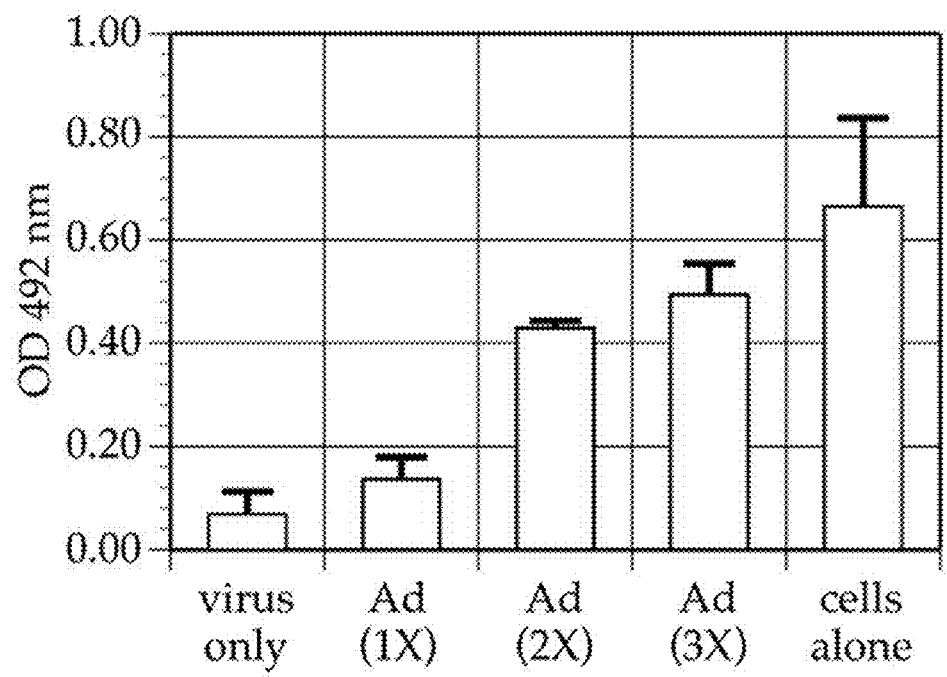
FIG. 2 is a bar graph showing neutralizing antibody levels from mice immunized with Ad5Null. Mice were immunized three times with Ad5Null viral particles at 14 day intervals. Note the presence of increasing neutralizing antibodies after each immunization. Optical density readings indicate the presence of viable target cells.

In an experiment to detect the presence of neutralizing antibodies to Ad, groups of 5 mice each were injected once, twice, or three times with $10^{10}$ Ad5null at two week intervals. Two weeks after the final injection of virus, mice were bled, pooled, and assessed for neutralizing antibody as described above using $4 \times 10^7$ VP incubated with or without heat inactivated sera. Cells cultured alone served as a control group. As shown in FIG. 2, normal mice and mice injected one time with Ad5null did not exhibit significant levels of neutralizing antibody. Mice injected two times with Ad exhibited significant (P<0.05) levels of neutralizing antibody as compared with cells incubated with virus only. Mice injected three times with Ad5-null also exhibited significant (P<0.01) levels of neutralizing antibody as compared with cells incubated with virus only.

Example 2

Multiple Injections of an E2b Deleted Adenovirus Vector Generates an Immune Response Against Target Antigens This example shows that multiple injections of an E2b deleted adenovirus vector containing HIV-gag results in the production of HIV-gag immunity.

Two groups of mice were used for this experiment. One group served as a normal control group. The second group was injected 3 times with E2b deleted Ad containing HIV-gag at 2 week intervals. Four weeks after the last injection, mice were bled and assessed for IgG antibody levels using an ELISA assay as follows: For this assay, 100 ng of a purified mixture of HIV-gag proteins p17/p24 were coated onto microtiter wells in 100 µL of 0.05M carbonate/bicarbonate buffer, pH 9.6, and incubated overnight at room temperature. For a standard IgG reference curve, purified mouse IgG (SigmaChemicals) in quantities of 200 ng, 100 ng, 50 ng, 25 ng, and 0 ng were coated onto microtiter wells as described above. After incubation, all wells were washed 3 times with 250 µL of 1% bovine serum albumin (BSA) in phosphate buffered saline (PBS), pH 7.4. After washing, 200 µL of BSA/PBS was added to wells and incubated for 30 minutes at room temperature to block any remaining sites in the microtiter wells. After incubation, all wells were washed 3 times with 250 µL of BSA/PBS. After washing, 200 µL of a 1/100 dilution of mouse serum in BSA/PBS was added to wells and incubated for one hour at room temperature. For a positive control, 100 ng of mouse monoclonal anti-p24 IgG antibody in BSA/PBS was added to wells. Blank control wells contained BSA/PBS only. After incubation, all wells were washed 3 times with 250 µL of BSA/PBS. After washing, 200 µL of a 1/10000 dilution of peroxidase conjugated gamma chain specific goat anti-mouse IgG (Sigma Chemicals) in BSA/PBS was added to each well and incubated for one hour at room temperature. After incubation, all wells were washed 3 times with 250 µL of BSA/PBS. After washing, 200 µL of developing reagent (0.5 mg/mL 1,2 phenylenediamine in 0.2M potassium phosphate buffer, pH 5.0, containing 0.06% hydrogen peroxide) was added to each well and incubated for 30-40 minutes at room temperature. After incubation, the color reaction was stopped by addition of 50 µL 5M HCl to each well. All wells were read in a microwell plate reader at 492 nm. After readings were obtained, the optical density readings of unknown samples were correlated with the standard IgG curve to obtain nanograms of IgG bound per well. This was performed utilizing the INSTAT statistical package.

Figure 3:
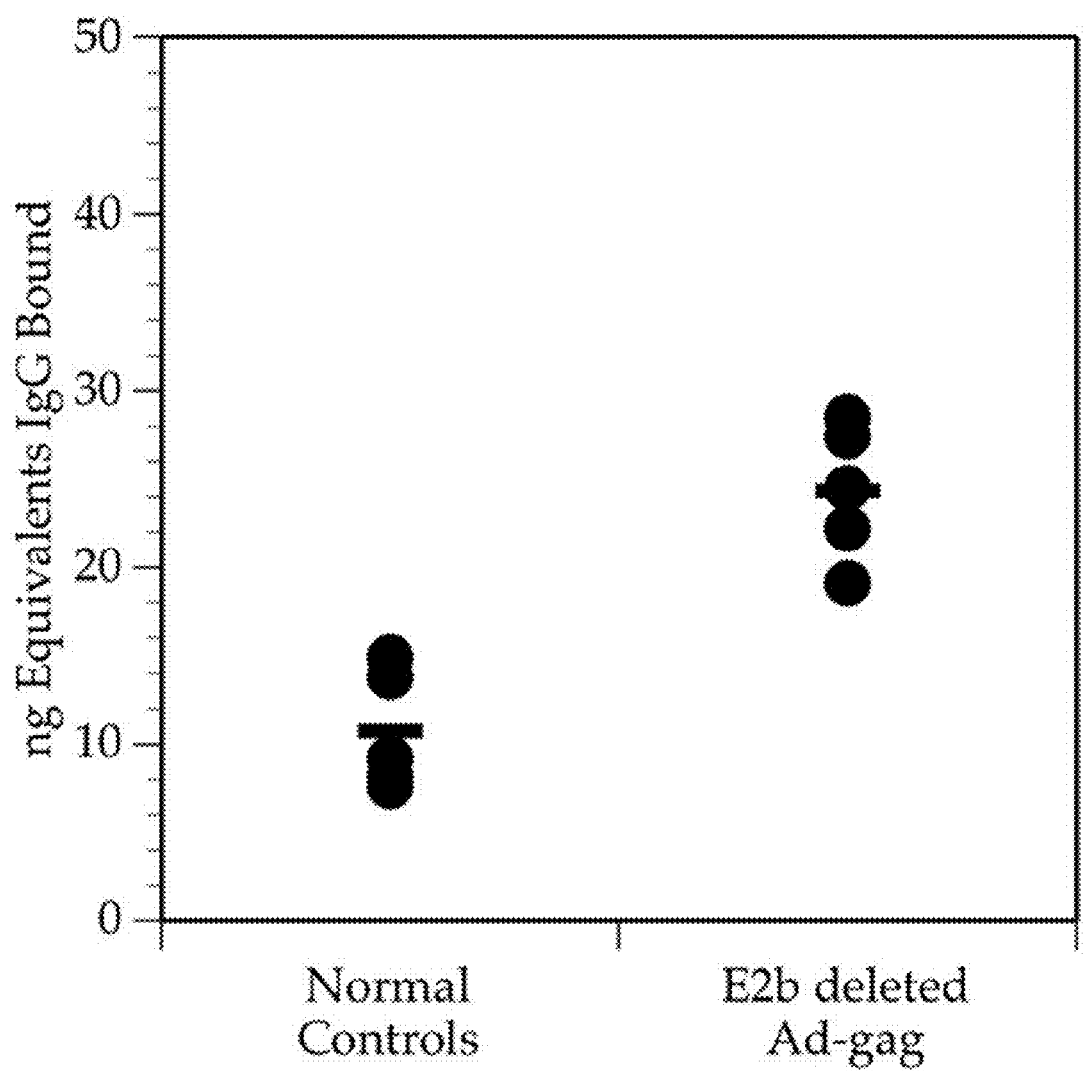
FIG. 3 shows the measured levels of antibody in immunized mice. Mice were injected three times with E2b deleted adenovirus vector containing the HIV-gag gene. Note the presence of significantly ($P<0.05$) elevated levels of Gag IgG antibody in experimental mice as compared to normal control mice. Horizontal bars represent the mean value.

As shown in FIG. 3, low but significant levels of Gag IgG were detected in mice 2 weeks after a second injection and 4 weeks after a third injection with $10^{10}$ E2b deleted Ad containing the HIV-gag gene. Moreover, when compared with respective pre-injections bleeds, low but significant levels ($P<0.01$) of detectable antibody were observed up to 8 weeks (Day 84) as well as 13 weeks (Day 119) post $3^{rd}$ injection with E2b deleted Ad-gag vector vaccine.

Example 3

Multiple Injections of an E2b Deleted Adenovirus Vector Generates an Immune Response Against Multiple Target Antigens This example demonstrates that mice injected multiple times with an E2b deleted adenovirus vector vaccine expressing a first target antigen (HIV-gag) and subsequently injected multiple times with an E2b deleted adenovirus vector expressing a second target antigen (β-galactosidase) produce an immune response against the first and the second antigen.

A group of five mice were injected 3 times at 2 week intervals with $10^{10}$ E2b deleted adenovirus vector vaccine containing the HIV-gag gene. Four weeks later, the mice were injected two times at a weekly interval with $10^{10}$ E2b deleted adenovirus vector vaccine containing β-galactosidase. A group of 5 mice served as a normal control group. Sera from mice injected only with E2b deleted Ad-βgal that showed high levels of β-galactosidase IgG antibody served as a positive control.

To determine the presence of β-galactosidase antibodies, an enzyme linked immunosorbent assay (ELISA) was used. For this ELISA, 100 ng of purified β-galactosidase was coated onto microtiter wells in 100 µL of 0.05M carbonate/bicarbonate buffer, pH 9.6 and incubated over night at room temperature. For a standard IgG reference curve, purified mouse IgG (Sigma Chemicals) in quantities of 200 ng, 100 ng, 50 ng, 25 ng, and 0 ng were coated onto microtiter wells as described above. After incubation, all wells were washed 3 times with 250 µL of 1% bovine serum albumin (BSA) in phosphate buffered saline (PBS), pH 7.4. After washing, 250 µL of BSA/PBS was added to all wells and incubated for 30 minutes at room temperature. After incubation, all were washed 3 times with 250 µL of BSA/PBS. After washing, 200 µL of a 1/100 of serum in BSA/PBS was added to wells and incubated for 1 hour at room temperature. Blank control wells contained BSA/PBS only. After incubation, all wells were washed 3 times with 250 µL of BSA/PBS. After washing, 200 µL of a 1/10000 dilution of peroxidase conjugated gamma chain specific goat anti-mouse IgG (Sigma Chemicals) in BSA/PBS was added to each well and incubated for 1 hour at room temperature. After incubation, all wells were washed 3 times with 250 µL of BSA/PBS. After washing, 200 µL of developing reagent (0.5 mg/mL 1, 2 phenylenediamine in 0.2M potassium phosphate buffer, pH 5.0, containing 0.06% hydrogen peroxide) was added to each well and incubated for 30-40 minutes at room temperature. After incubation, the color reaction was stopped by addition of 50 µL 5N HCl to each well. All wells were then read in a microwell plate reader at 492 nm. After readings were obtained, the optical density readings of unknown samples were correlated with the standard IgG curve to obtain the nanograms of IgG bound per well. This was performed utilizing the INSTAT statistical package.

Figure 4:
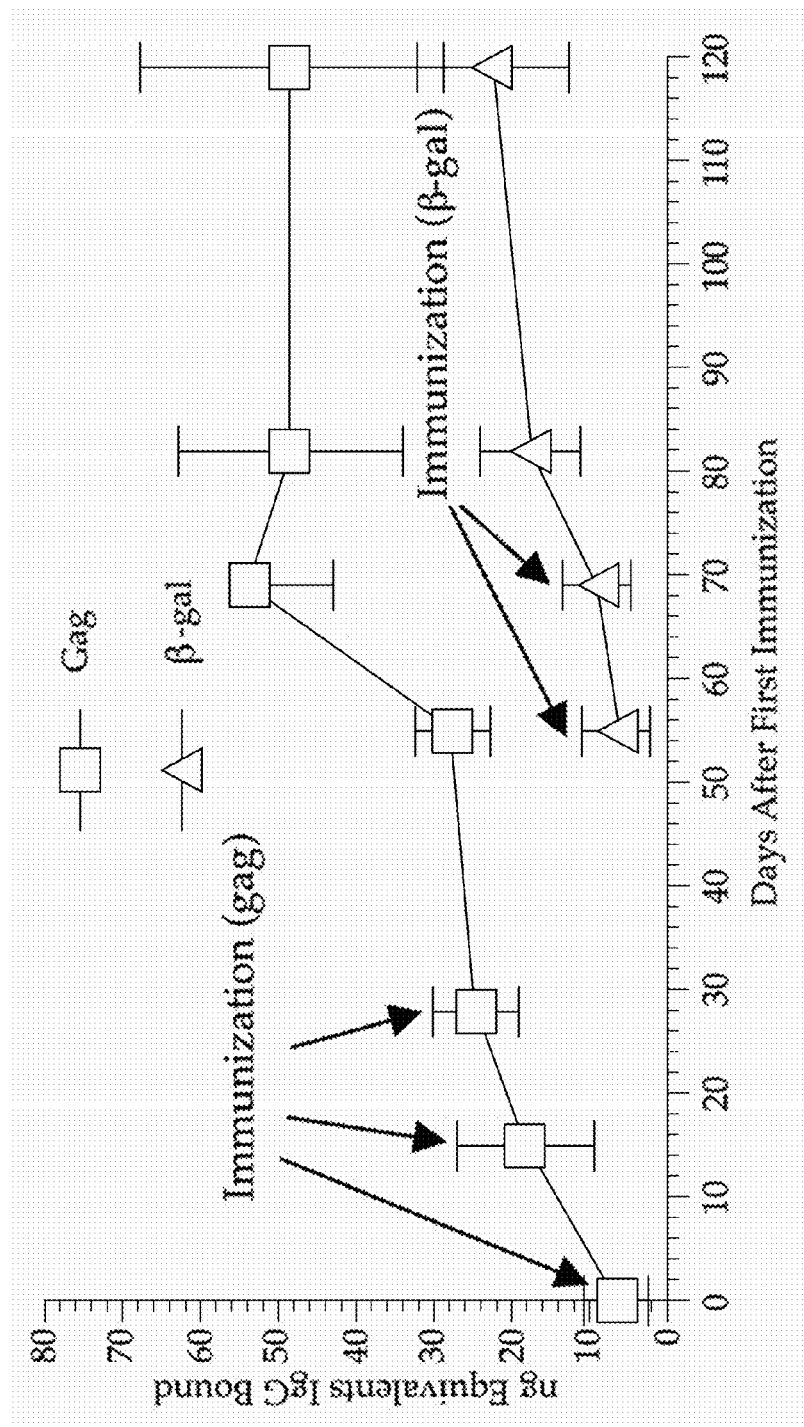
FIG. 4 is a graph showing antibody levels over time in mice immunized with two different E2b deleted adenovirus vectors each with a different target antigen. Mice were immunized with E2b deleted adenovirus vector containing the HIV-gag gene three times at 14 day intervals. Four weeks later, the same group of mice was immunized two additional times at 14 day intervals with E2b deleted adenovirus vector containing the *Escherichia coli* β-galactosidase gene. Note the presence of increasing levels of HIV-Gag IgG antibody levels after multiple immunizations as compared to pre-immunization levels. Moreover, note the presence of increasing levels of β-galactosidase IgG antibody after two injections in the same group of mice as compared to pre-immunization levels.

As shown in FIG. 4, sera assessed 2 weeks after the last injection from mice injected with E2b deleted adenovirus vector containing *E. coli* β-galactosidase exhibited significantly ($P<0.01$) higher levels of anti-β-galactosidase IgG antibodies as compared to normal control mice. Detectable levels of anti-β-galactosidase antibody persisted up to 5 weeks after the last injection. Moreover, significant levels of HIV-gag immunity were still readily detected and levels of these antibodies even increased.

In a related experiment, cellular immune responses in mice were assessed after multiple immunizations. Mice were immunized with E2b deleted adenovirus vector vaccine containing the HIV-gag gene three times at 14 day intervals. Four weeks later, the mice were subsequently immunized with E2b deleted adenovirus vector vaccine containing the β-galactosidase gene twice at 14 day intervals. ELISpot assays were performed to determine cellular mediated immune responses in vaccinated subjects. ELISpot assay kits were obtained from eBioscience and assay plates were prepared according to manufacturer's specifications. The assay was performed as described in the manufacturer's instructions. Briefly, capture antibody was coated onto ELISpot assay plates per instructions and coated overnight. After washing and blocking unbound sites, mitogen, specific antigen, and controls were added to wells in complete RPMI-1640 culture medium at 100 μL per well. Spleen cells from mice were harvested and prepared for cell culture. Cells were then added to wells in a 100 μL volume at the desired cell density. The ELISpot plates were then incubated at 37 C in a 5% $CO_2$ humidified incubator for approximately 48 hours. After incubation, the ELISpot plates were developed according to manufacturer's instructions. The data was expressed as the number of spot forming cells (SPC) per $10^6$ splenocytes.

Figure 5A:
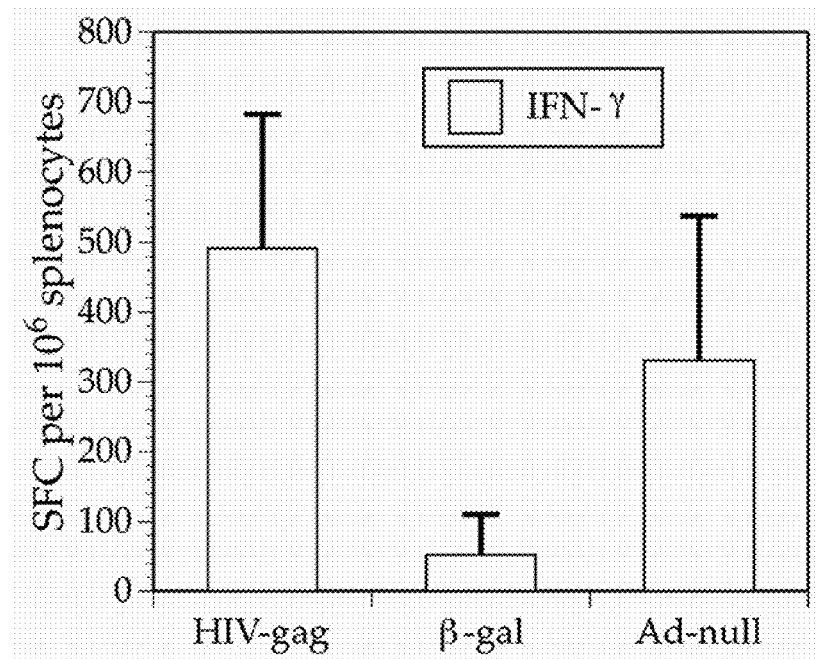
FIG. 5A and FIG. 5B are bar graphs showing numbers of T-cells expressing IFN-γ and IL-2, respectively. Mice were immunized with E2b deleted adenovirus vector containing the HIV-gag gene three times at 14 day intervals. Four weeks later, the same group of mice was immunized two additional times at 14 day intervals with E2b deleted adenovirus vector containing the β-galactosidase gene. To assess cell-mediated immune responses, ELISPOT assays were performed to determine the number of interferon-γ (IFN-γ) or interleukin-2 (IL-2) secreting cells following stimulation with the HIV-Gag protein, β-galactosidase, or Ad5Null virus. The data are expressed as the number of spot forming cells (SFC) per $10^6$ splenocytes. Note the number of IFN-γ and IL-2 producing cells after splenocytes were stimulated.
Figure 5B:
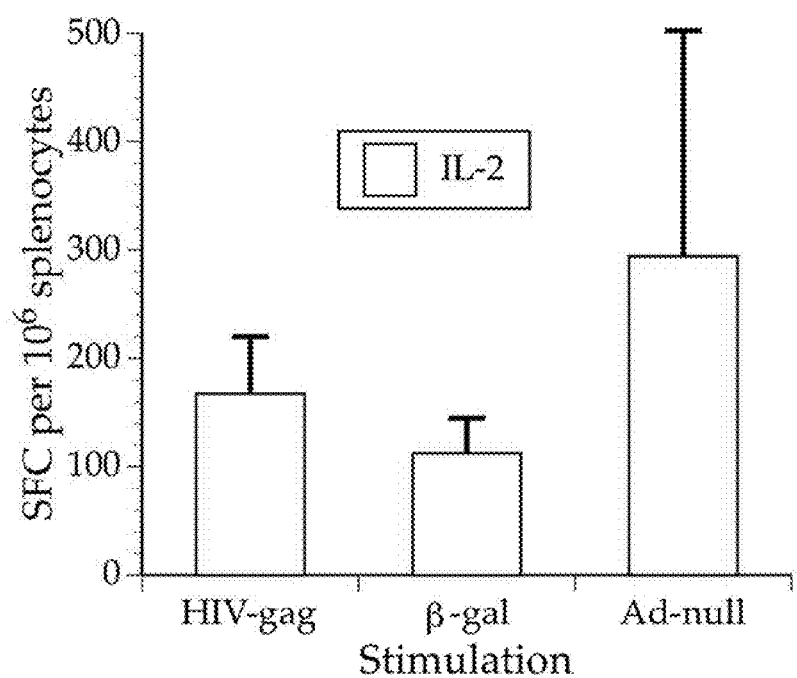

As shown in FIG. 5A, ELISpot analysis showed that mice exhibited the production interferon-γ (IFN-γ) upon re-stimulation to HIV-gag and Ad5null virions. Furthermore, as shown in FIG. 5B, ELISpot analysis also showed the production of interleukin-2 (IL-2) upon re-stimulation with HIV-gag, β-galactosidase, and Ad5null virions. These results indicated that cell-mediated immune responses could be generated in the same subjects after multiple injections with E2b deleted adenovirus vector vaccines encoding 2 differing target antigens. Moreover, the cell-mediated immune response against the second immunizing antigen occurred in the presence of immunity to Ad.

Thus, the E2b deleted adenovirus vectors of the present invention can be used to immunize against multiple antigens using regimens of multiple immunizations.

Example 4

Cell Mediated Immune (CMI) Response Induction in Adenovirus 5 Immune Cynomolgus Macaques This example shows that multiple injections of an E2b deleted adenovirus vector containing HIV-gag results in the production of HIV-gag immunity, even in the presence of Ad5 immunity.

Figure 6:
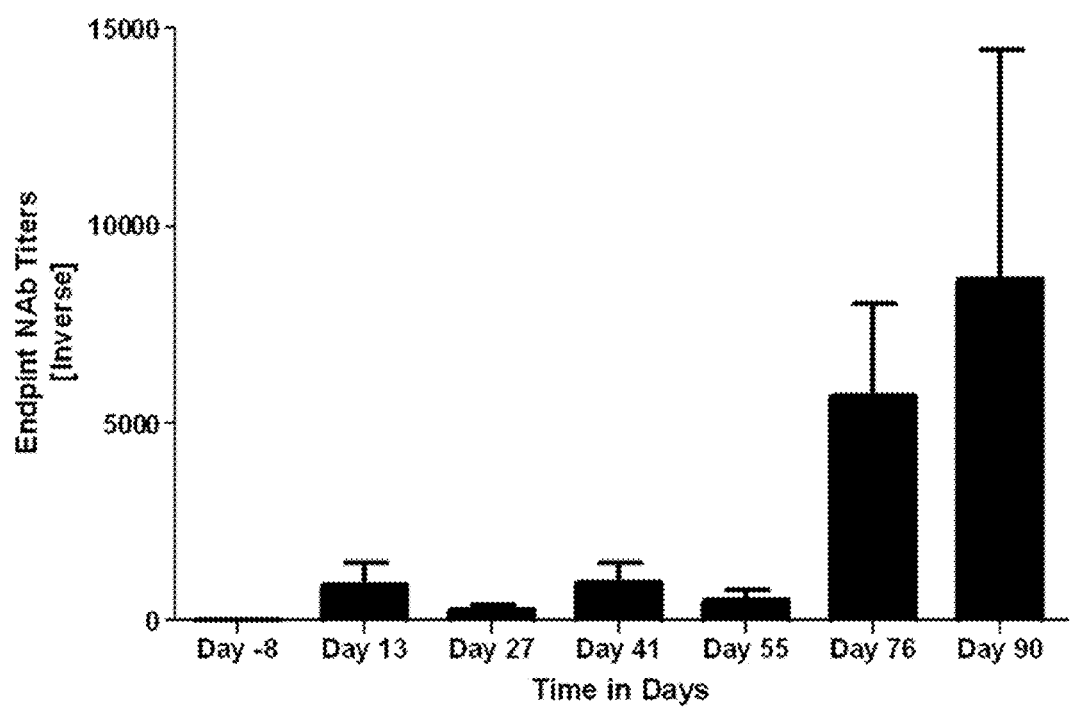
FIG. 6 is a bar graph showing the Ad5 neutralizing antibody (NAb) titers in non-human primates (NHP) during the vaccination protocol using Ad5 [E1-, E2b-]-gag. Three NHP were injected with a single does of $10^{10}$ VP viable wild type Ad5. Ad5 NAb was measured 30 days after administration and the NHP titers were $\geq 1:50$. The Ad5 immune NHP were then immunized three times on days 0, 27, and 58 with Ad5 [E1-, E2b-]-gag ($10^{10}$ VP/dose). Note the increasing levels of NAb induced during vaccination with Ad5 [E1-, E2b-]-gag. Vertical bars indicate the Standard Error of the Mean (SEM).
Figure 7:
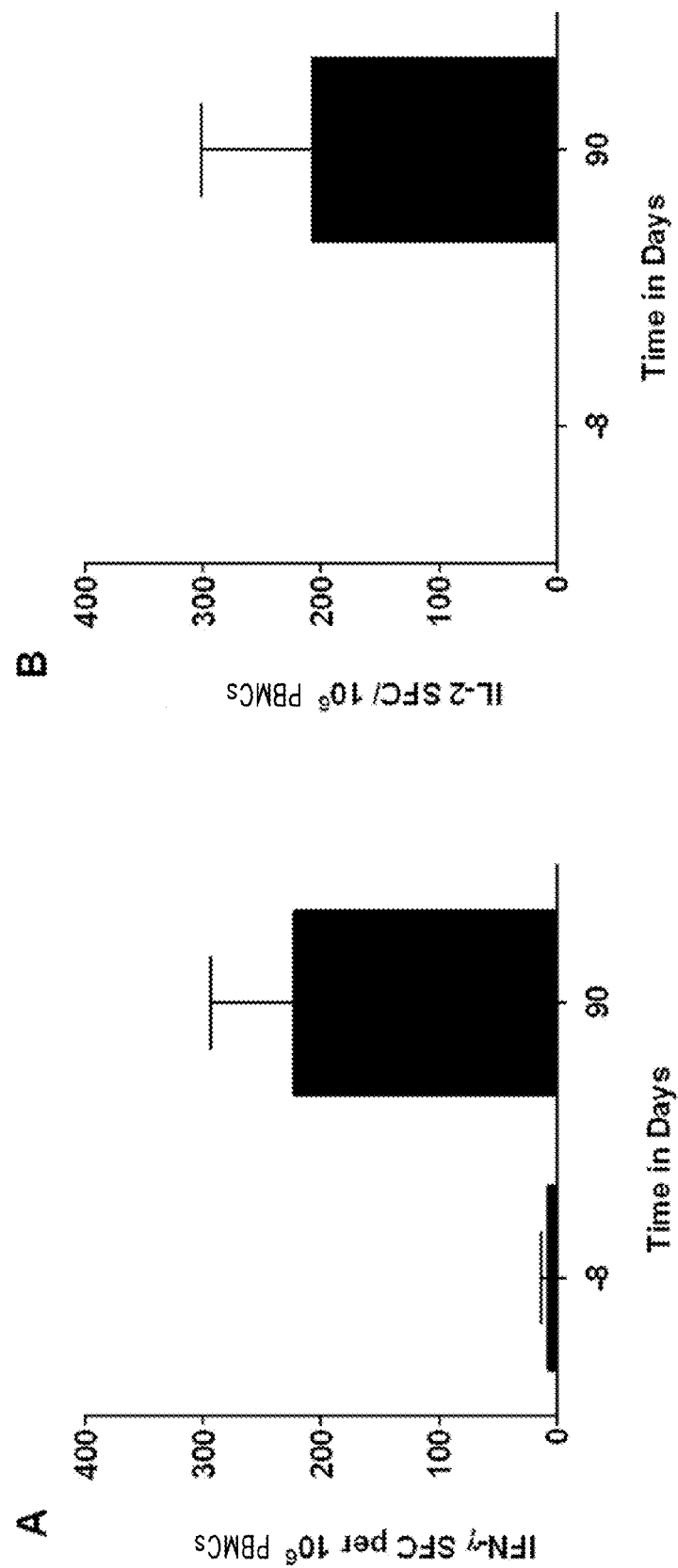
FIG. 7A and FIG. 7B are bar graphs showing numbers of peripheral blood mononuclear cells (PBMCs) in Ad5 immune cynomolgus macaques secreting IFN-γ and IL-2, respectively. PBMCs from individual NHP were collected and cell-mediated immune (CMI) responses were assayed 32 days (Day 90) after the final immunization with Ad5 [E1-, E2b-]-gag. Note the significantly ($P<0.05$) elevated levels of IFN-γ (FIG. 7A) and IL-2 (FIG. 7B) secreting cells from the PBMC sample taken after the vaccination protocol as compared to a baseline sample (Day-8) taken before vaccinations. The ELISpot data are expressed as the number of spot forming cells (SFC) per $10^6$ PBMCs. Vertical bars indicate the SEM.

Three non-human primates (NHP) were injected with a single dose of $10^{10}$ VP viable wild type Ad5. Ad5 neutralizing antibody (NAb) was measured 30 days after administration, and the NHP titers were ≧50 (FIG. 6). The Ad5 immune NHP were then immunized three times; days 0, 27, and 58; with Ad5 [E1-, E2b-]-gag ($10^{10}$ VP/dose). Peripheral blood mononuclear cells (PBMC) from individual NHP were collected at the indicated time points. CMI responses upon re-stimulation with HIV-gag protein were assayed 32 days after the final immunization with Ad5 [E1-, E2b-]-gag. ELISpot analysis indicated that PBMC from all three NHP responded similarly upon re-stimulation with HIV-gag protein with an average frequency of 223 SFC/$10^6$ PBMC producing INF-γ and 207 SFC/$10^6$ PBMC producing IL-2 (FIG. 7A and FIG. 7B, respectively). These values were significantly (P<0.05) elevated when compared to their baseline values. The Ad5 viral NAb titers ranged from 1/1000 to 1/20,000 at the termination of this study (FIG. 6).

As evidenced by the induction of specific CMI responses to the HIV-gag protein, these results indicate that NHP can be successfully immunized with the Ad5 [E1-, E2b-] vector platform in the presence of Adenovirus 5 immunity.

Example 5

A Modified HER2 Cancer Vaccine Vector Based on the Ad5 [E1-, E2b-] Platform

This example shows that multiple immunizations of Ad5 immune mice with Ad5 [E1-, E2b-]-HER2 induced HER2 specific cell mediated immune responses and antibody responses that had beneficial effects on tumor progression.

Production and Characterization of Ad5 HER2 Vector

The Ad5 [E1-, E2b-]-HER2 vector was constructed by recombination in BJ5183 bacterial cells and rescued by transfection into pre-terminal protein (pTP) and polymerase (pol) expressing E.C7 cells. The Ad5 [E1-, E2b-]-HER2 vector contains deletions in both the pol and pTP genes, since this arrangement has been demonstrated to result in decreased liver toxicity when compared to Ad5 [E1-]. The mini-gene cassette expressing HER2 was subcloned into the E1 region of a shuttle vector and recombined with E2b deleted (pol-, pTP-) Ad5 genomic DNA. The recombined Ad5 [E1-, E2b-]-HER2 was verified by restriction analysis and rescued as viruses by restriction enzyme release and transfection into E.C7 cells.

The HER2 gene utilized for these studies was a modified kinase-inactive HER2 having a K753A mutation that renders it non-oncogenic (Morse, M. A. et al., Int. J. Cancer, 2009, Vol. 9999, Issue 999A, page NA, published online 23 Oct. 2009 and Akiyama, T. et al., Mol. Cell. Biol. 1991, 11(2):833-842).

The Ad5 [E1-, E2b-]-HER2 viral vector was manufactured by releasing from E.C7 producer cells by Triton X-100, precipitated in PEG, purified on CsCl gradients, dialyzed against 20 mM HEPES (pH 7.4) containing 5% sucrose, aliquoted, and frozen in a dry ice-ethanol bath. Particle concentration was calculated both by absorption at 260 and 280 nm (normal ratio=1.3). The infectivity of the virus particles (VP) was measured in a plaque assay and the infectious units per total virus particles (IU/VP) was 1/90.

Figure 8:
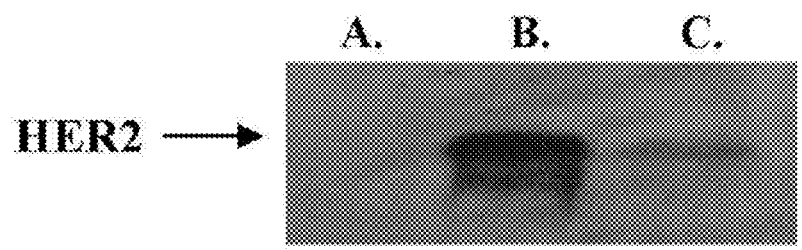
FIG. 8 is a Western blot image showing HER2 expression in human cells. Human A-549 cells were infected with saline (A); Ad5 [E1-, E2b-]-HER2 at a multiplicity of infection (MOI) of 900 (B); or Ad5 [E1-, E2b-]-HER2 at an MOI of 150 (C). After 24 hours, total cell protein was harvested and HER2 protein expression was assessed by Western blot.

Studies were performed to confirm HER2 gene expression of both Ad5 [E1-, E2b-]-HER2 vector platform. It was first determined that the HER2 antigen could be expressed on cells transfected with the vector platform. A549 cells were obtained from ATCC and transfected with Ad5 [E1-, E2b-]-HER2. Western Blot analysis was performed to determine HER2/neu expression by the Ad5 [E1-, E2b-]-HER2/neu vector platform. Briefly, $10^6$ human lung carcinoma cells (A-549) (ATCC number CCL-185) were infected at a multiplicity of infection (MOI) of 900 and 150 VP, incubated for 24 hr and then lysed. Cell lysates were separated on a 10% SDS-polyacrylamide gel and transferred onto a PVDF membrane (GE Healthcare, Piscataway, N.J.). The membranes were then blocked with TBS containing 5% (w/v) blocking reagent (GE Healthcare, Piscataway, N.J.) for 2 hours at room temperature and sequentially incubated with mouse anti-HER2 antibody (1:250) (Genway, San Diego, Calif.) and goat anti-mouse-HRP conjugated:antibody (1:1000) (Kirkegaard & Perry Laboratories, Gaithersburg, Md.) for one hour at room temperature. Reactivity was determined by chemilluminescence using an ECL Western Blotting analysis system (GE Healthcare, Piscataway, N.J.) according to the manufacturer's specifications. As shown in FIG. 8, a single HER2 expressing band was observed.

Figure 9:
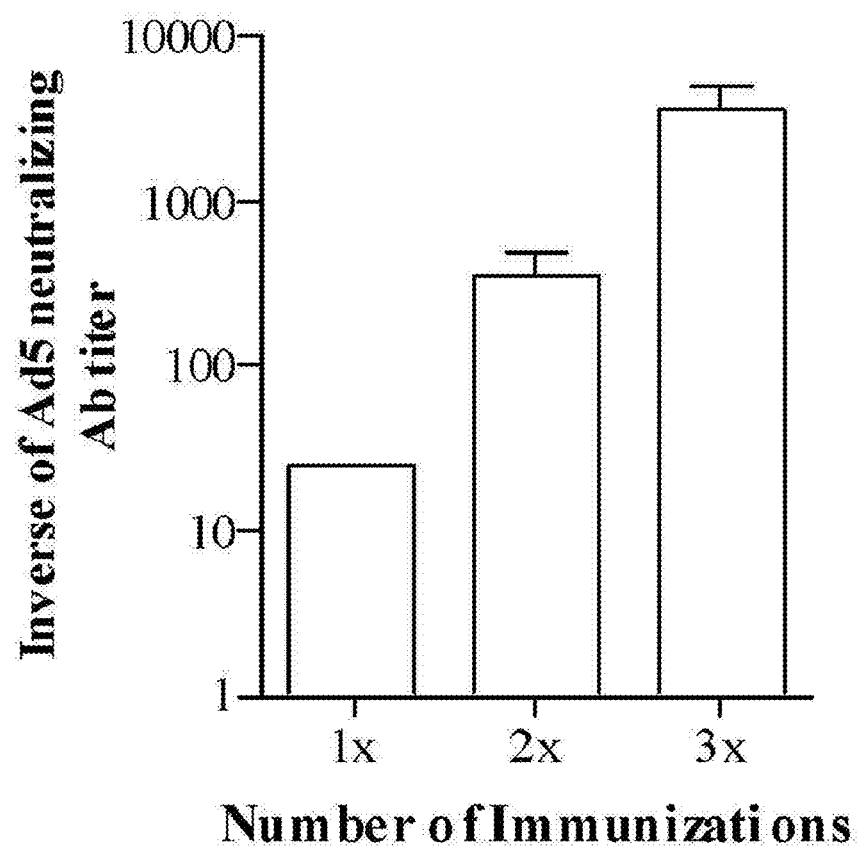
FIG. 9 is a bar graph showing neutralizing antibody (NAb) titers in BALB/c mice immunized 1, 2, or 3 times with $10^{10}$ Ad5-null VP. Values represent mean±SEM.

Induction of Ad5 Immunity in Mice as Evidenced by Levels of Ad5 Neutralizing Antibody To induce Ad5 immunity, Ad5 naïve BALB/c mice were injected intradermally twice at two week intervals with $10^{10}$ virus particles of Ad5-null (empty). Two weeks later, serum samples were collected and assessed for endpoint Ad5 neutralizing antibody (NAb) titers. As shown in FIG. 9, this protocol induced NAb activity in BALB/c mice. BALB/c mice were used because the HER2 expressing tumor line used for the immunotherapy studies is implanted in this strain of mouse. In the studies below, mice were made Ad5 immune by two injections with Ad5-null.

Immunization of Ad5 Immune Mice with Ad5 [E1-, E2b-]-HER2

Figure 10:
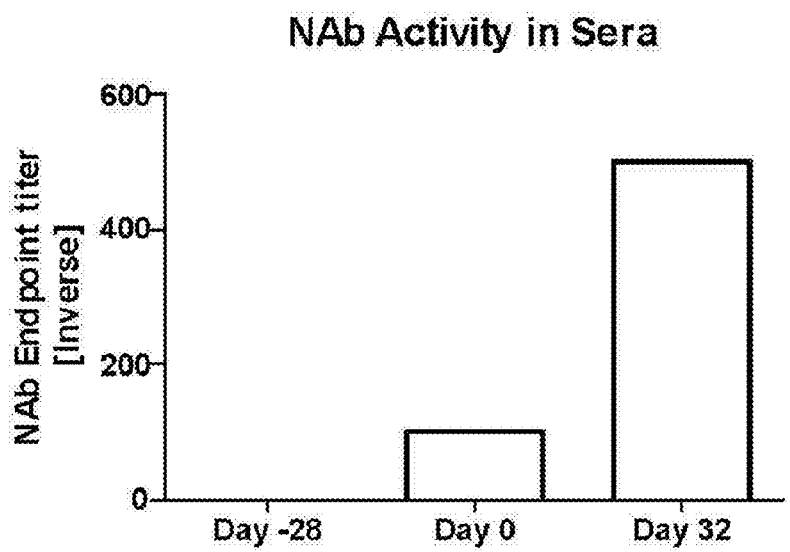
FIG. 10 is a bar graph showing serum Ad5 NAb levels in BALB/c mice vaccinated 3 times on days 0, 7, & 17 with $10^{10}$ Ad5 [E1-, E2b-]-HER2. Mice were made Ad5 immune by 2 injections with Ad5-null on days-28 and -14. Note the high levels in NAb activity on day 32 at which time splenocytes were assessed for CMI responses. Values represent the inverse of the endpoint NAb.

Experiments were performed to assess immune responses in Ad5 immune mice during multiple immunizations with Ad5 vector based vaccines. Two weeks following the last Ad5-null immunization, groups of female BALB/c mice, 4 to 8 weeks old, were immunized one, two or three times at weekly intervals with $10^{10}$ virus particles of Ad5 [E1-, E2b-]-HER2. Assessment of sera after two injections with Ad5-null revealed that the Ad5 NAb endpoint NAb titers were $1/100$. Thus, before mice were immunized, their pre-existing Ad5 NAb endpoint titers were $1/100$ (FIG. 10). Two weeks following the last immunization with Ad5 [E1-, E2b-]-HER2, mice were euthanized and their spleens were harvested for analysis of CMI and antibody responses.

Induction of CMI Responses

Figure 11:
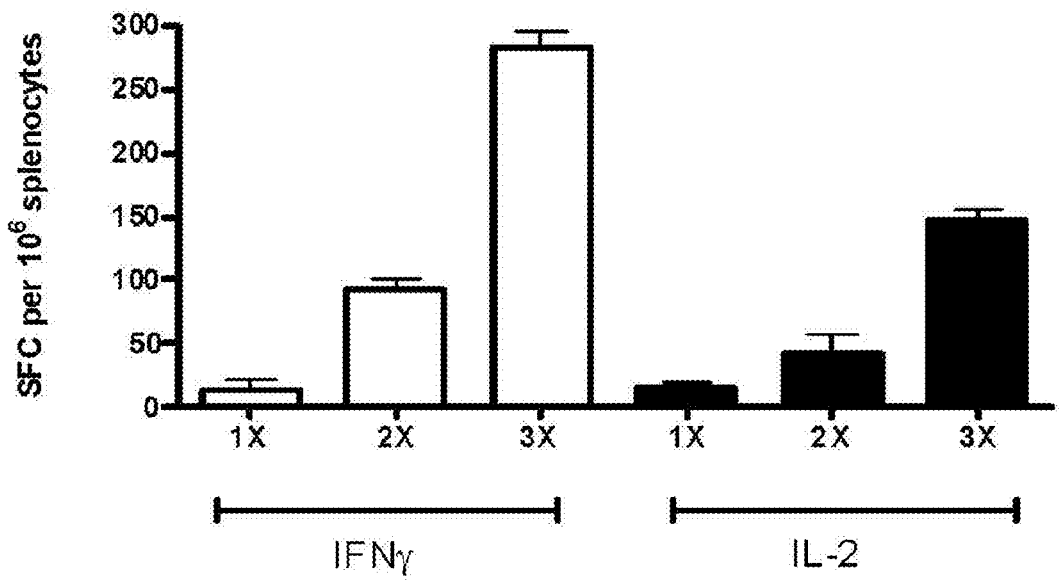
FIG. 11 is a bar graph showing INF-γ and IL-2 secreting splenocytes (SFC) from Ad5 immune mice immunized 1, 2, or 3 times with Ad5 [E1-, E2b-]-HER2. Note the highly elevated CMI responses after the third immunization (3×). For positive controls, splenocytes were exposed to Concanavalin A (Con A) (data not shown). Values represent the mean±SEM.

Cell mediated immune responses were assessed by ELISpot assays performed on splenocytes exposed to HER2 peptides. Splenocytes from Ad5 immune BALB/c mice that were immunized subcutaneously with Ad5 [E1-, E2b-]-HER2 were harvested and assessed for the number of IFN-γ and IL-2 secreting splenocytes. As shown in FIG. 11, elevated numbers of IFN-γ and IL-2 secreting cells were observed in spleens assayed from mice after two immunizations with Ad5 [E1-, E2b-]-HER2. Moreover, the highest numbers of IFN-γ and IL-2 secreting cells were observed after the third immunization.

Specificity studies revealed that immunizations induced specific HER2 associated CMI responses and not responses against other irrelevant antigens such as the cytomegalovirus (CMV) antigen or β-galactosidase. As shown in FIG. 10, the HER2 CMI responses occurred despite the presence of high levels ($1/500$ titer) of Ad5 NAb activity in sera resulting from multiple immunizations. These results demonstrate that multiple immunizations of Ad5 immune mice with Ad5 [E1-, E2b-]-HER2 induced HER2 specific CMI responses.

Induction of Humoral Responses

Figure 12:
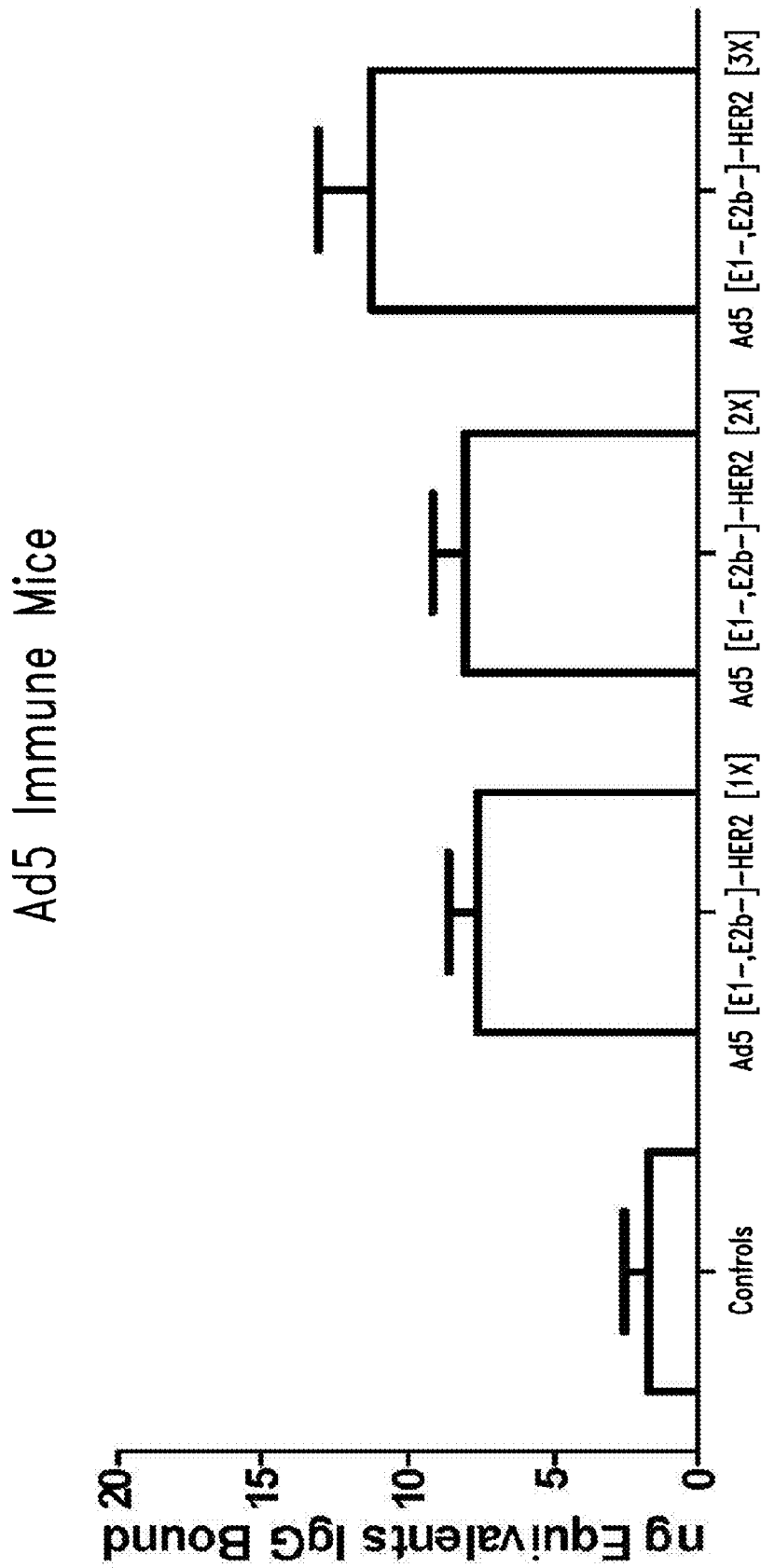
FIG. 12 is a bar graph showing anti-HER2 IgG antibody levels in Ad5 immune mice immunized one (1×), two (2×), or three (3×) times with Ad5 [E1-, E2b-]-HER2. Note the increasing antibody levels associated with increasing immunizations. Serum samples diluted 1/100 and antibody levels were assessed by ELISA with reference to a standard IgG curve to quantitate IgG antibody levels. Values represent Mean±SEM.

Studies were also performed to determine if anti-HER2 IgG antibody was induced after immunizations. An ELISA for circulating IgG antibody to HER2 was performed. As shown in FIG. 12, increasing quantities of detectable antibody to HER2 were observed after one, two, and three immunizations with Ad5 [E1-, E2b-]-HER2, with the greatest quantities of antibody observed after the third immunization. Statistical t test analyses revealed that antibody levels were significantly ($P<0.05$) elevated after one, two, or three immunizations as compared with control values. These results indicate that in addition to CMI responses, antibody responses directed toward the HER2 protein were also induced in Ad5 immune mice immunized with Ad5 [E1-, E2b-]-HER2.

Lack of Adverse Liver Effects in Immunized Mice

Figure 13A:
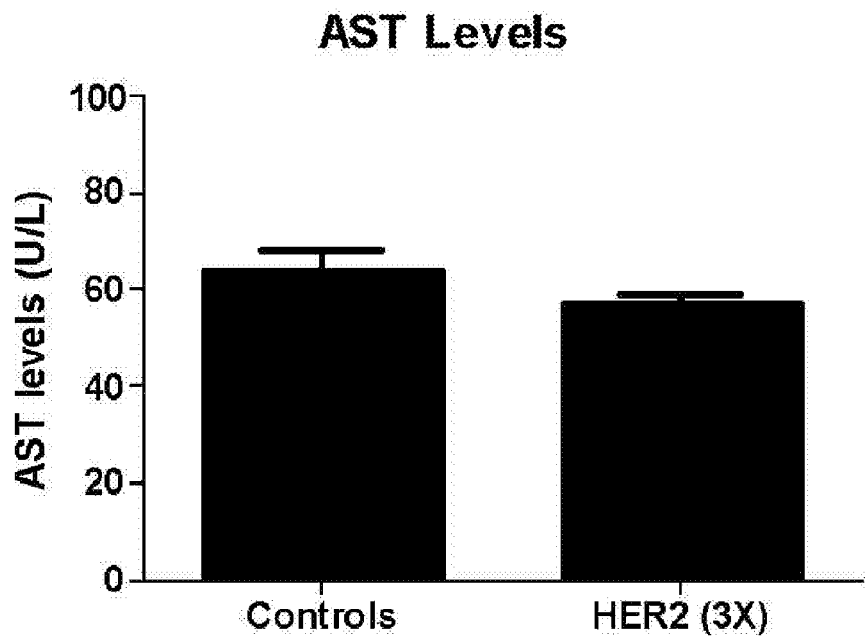
FIG. 13A is a bar graph showing serum AST levels in control mice and mice vaccinated 3 times [HER2 (3×)] with $10^{10}$ viral particles of Ad5 [E1-, E2b-]-HER2. Values represent mean±SEM.
Figure 13B:
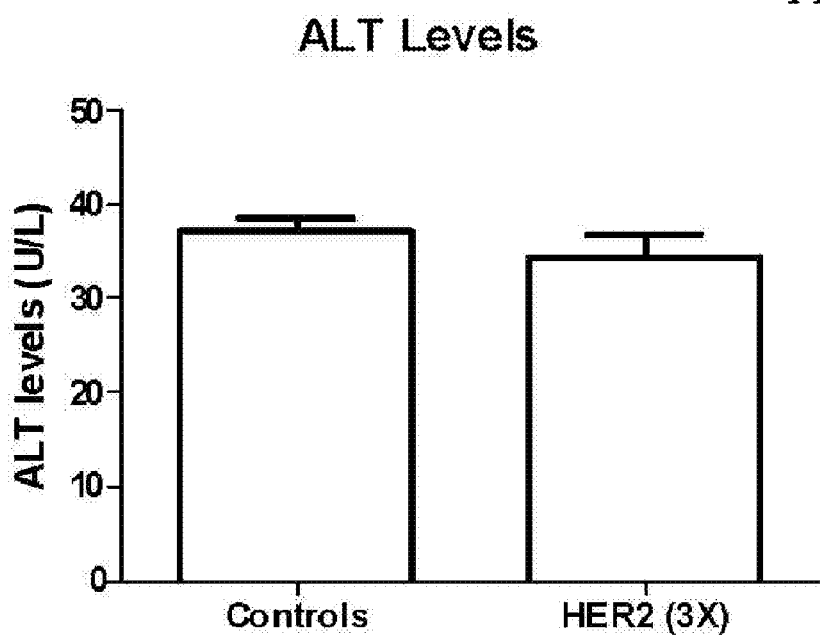
FIG. 13B is a bar graph showing serum ALT levels in control mice and mice vaccinated 3 times [HER2 (3×)] with $10^{10}$ viral particles of Ad5 [E1-, E2b-]-CEA. Values represent mean±SEM.

Toxicity studies were performed on serum from Ad5 immune mice immunized with Ad5 [E1-, E2b-]-HER2 as described above. Ad5 immune mice injected with buffer alone served as controls. Three days after the third immunization, aspartate aminotransferase (AST) and alanine aminotransferase (ALT) levels were assessed on the blood samples to determine liver toxicity due to immunizations (FIGS. 13A and 13B). AST and ALT levels were not elevated over controls following immunization with the Ad5 vector. These results demonstrate that mice can be safely immunized with Ad5 [E1-, E2b-]-HER2 to induce specific humoral and CMI responses against the HER2 antigen.

Challenge of Ad5 [E1-, E2b-]-HER2 Immunized Ad5 Immune Mice with HER2 Expressing Tumors Studies were performed to determine if Ad5 immune mice could first be immunized with the Ad5 [E1-, E2b-]-HER2 vector platform and resist a challenge of implanted HER2 expressing tumor cells. BALB/c mice were utilized for these studies. A HER2 expressing BALB/c murine tumor cell line (CT26-HER2) was used. This particular murine cell line is a carcinoma that has been genetically modified to express human HER2 and can be implanted into BALB/c mice.

Figure 14:
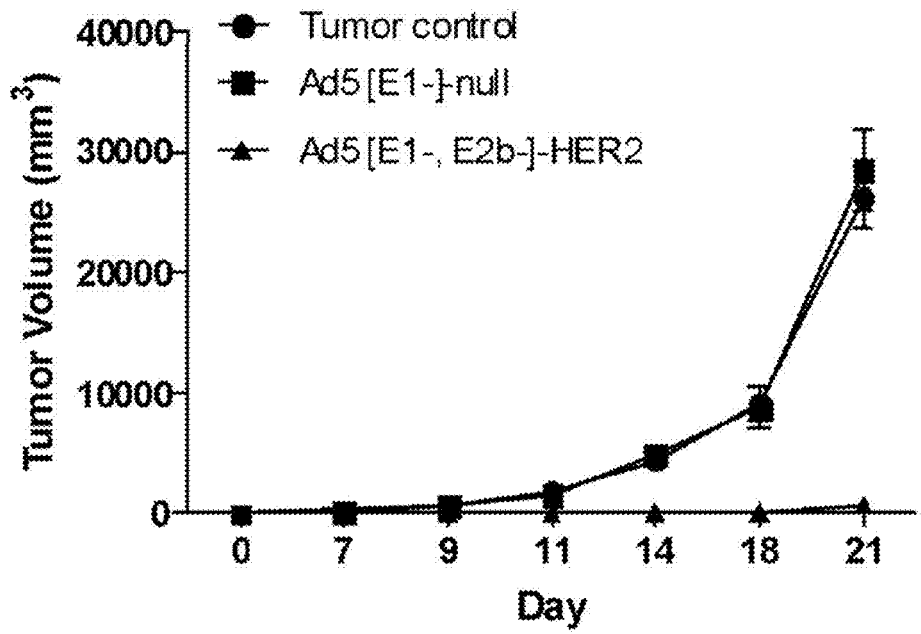
FIG. 14 is a line graph showing tumor volume. Ad5 immune mice were injected 3 times with Buffer solution, Ad5-Null (empty), or Ad5 [E1, E2b-]-HER2. Two weeks after the last immunization, they were challenged with HER2 expressing tumors. Note the significant lack of tumor growth in the Ad5 [E1-, E2b]-HER2 immunized mice. Values represent the mean±SEM.

Groups of 7 mice each were first injected two times at two week intervals with Ad5-null to render the mice Ad5 immune. Two weeks after the last Ad5-null injection, the mice were immunized three times at weekly intervals with injection buffer (Tumor Controls), Ad5-null (Vector Controls), or Ad5 [E1-, E2b-]-HER2 (Immunized Group). Two weeks following the last immunization (or injection), the mice were implanted subcutaneously with $1 \times 10^6$ CT26-HER2 cells. After implantation, tumor growth was monitored. The tumors were measured and the tumor volumes calculated. As shown in FIG. 14, mice immunized with Ad5 [E1-, E2b-]-HER2 resisted a challenge with HER2 expressing tumor. This was in comparison with receiving injections of buffer only or Ad5-null where the tumors grew to a point at which the mice were humanely exsanguinated. These results demonstrate that Ad5 immune mice immunized with Ad5 [E1-, E2b-]-HER2 can significantly slow the progress of tumor growth after a lethal challenge of HER2 expressing tumor cells.

Example 6

The Ad5 [E1-]-CEA Vector Vaccine Induces CEA Specific Immune Response Upon Re-Immunization in Ad5 Immune Mice This example shows that the Ad5 [E1-, E2b-] vector platform induces CMI responses against the tumor associated antigen (TAA) carcinoembryonic antigen (CEA) in the presence of pre-existing Ad5 immunity in mice.

Characterization of Ad5 CEA Vectors

Initial studies were performed to confirm CEA gene expression of two Ad5-CEA vector platforms. It was first determined that the CEA antigen could be expressed on cells transfected with the vaccine vector platforms. A549 cells were obtained from ATCC and transfected with Ad5 [E1-]-CEA or Ad5 [E1-, E2b-]-CEA. Western blot analysis revealed that cells transfected with the vector platforms expressed CEA antigen.

Induction of Ad5 Immunity in Mice

Figure 15:
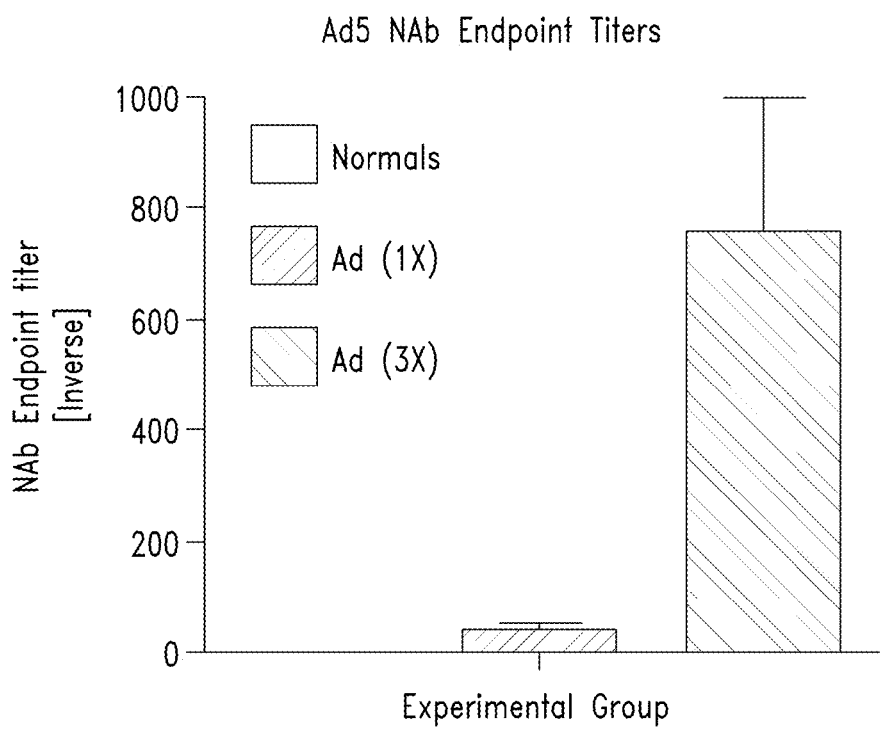
FIG. 15 is a bar graph showing the induction of NAb in C57BI/6 mice after injections with Ad5-Null vector platform (VP). Note the increasing levels of NAb induced in mice after repeated injections with Ad particles. Values represent mean±SEM.

To assess the levels of Ad5 immunity that could be induced, groups of Ad5 naïve C57Bl/6 mice were injected subcutaneously with the Ad5 vector platform (VP). Twenty eight to forty two days later, serum samples were collected and assessed for endpoint Ad5 NAb titers. As shown in FIG. 15, undetectable Ad5 NAb titers (endpoint Ad5 NAb titer $<1/25$) were observed in normal control mice. Ad5 NAb (endpoint titers of $1/25$ to $1/50$) was detectable after one injection but dramatically increased after three injections of $10^{10}$ Ad5. Therefore, in additional Ad5 immune studies, mice were injected twice with $10^{10}$ Ad5 VP to render the animals Ad5 immune.

Immunization of Ad5 Immune Mice with Ad5 [E1-]-CEA or Ad5 [E1-, E2b-]-CEA.

These experiments were designed to determine and compare the immunization induction potential of Ad5 [E1-]-CEA and Ad5 [E1-, E2b-]-CEA vaccines in Ad5 immune mice. Groups of female C57Bl/6 mice, 4 to 8 weeks old, were immunized 2 times at 2 week intervals with $10^{10}$ Ad5-null VP. Two weeks following the last Ad5-null immunization, the mice were immunized 3 times at weekly intervals with $10^{10}$ VP of Ad5 [E1-]-CEA or Ad5 [E1-, E2b-]-CEA. Two weeks following the last immunization, mice were euthanized and their spleens and sera harvested for analyses.

Figure 16A:
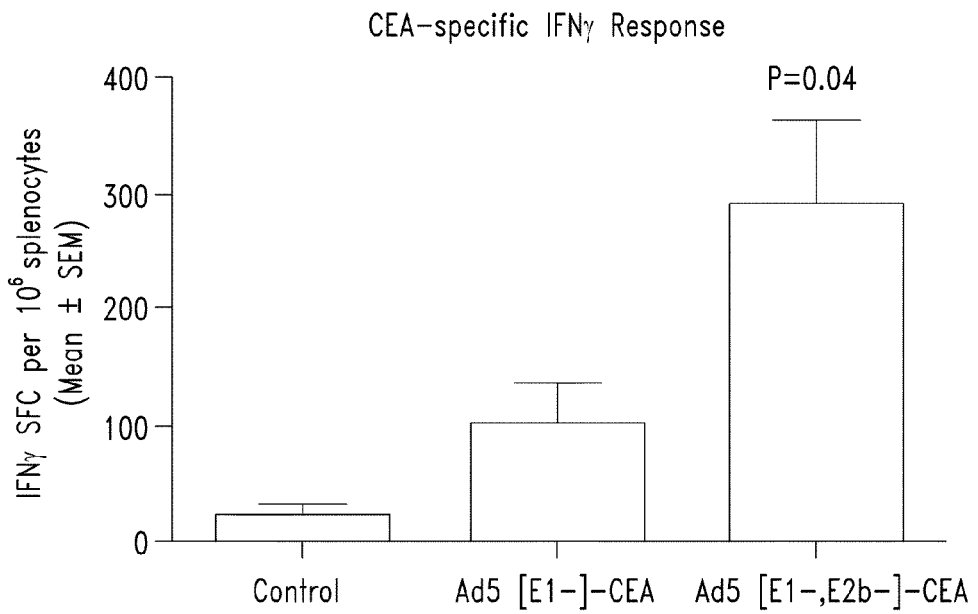
FIG. 16A is a bar graph showing INF-γ secreting splenocytes from Ad5 immune mice immunized with Ad5 [E1-]-CEA or Ad5 [E1, E2b-]-CEA. Note the significantly elevated response in splenocytes from the Ad5 [E1-, E2b]-CEA immunized group. Values represent mean±SEM.
Figure 16B:
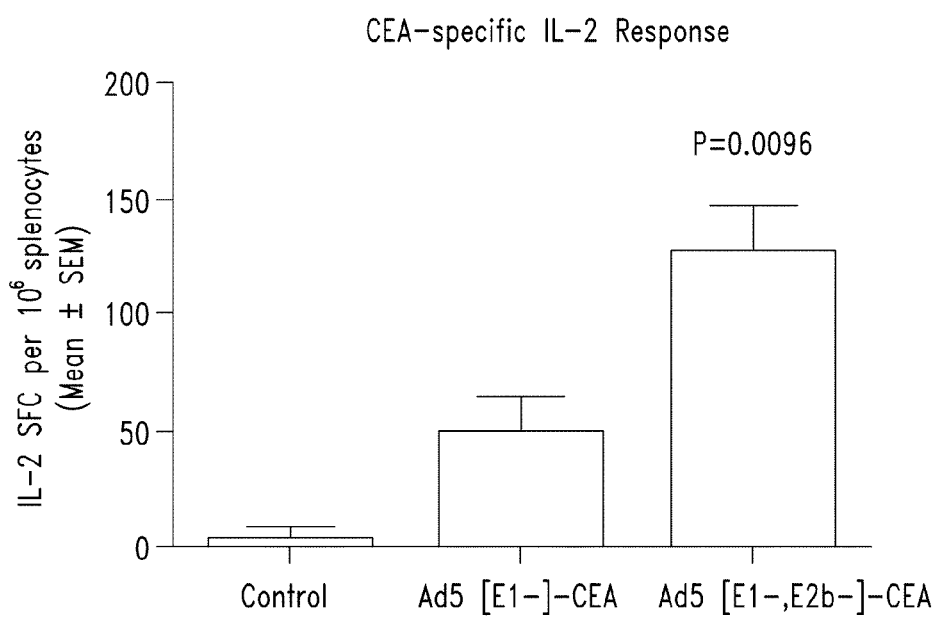
FIG. 16B is a bar graph showing IL-2 secreting splenocytes from Ad5 immune mice immunized with Ad5 [E1-]-CEA or Ad5 [E1-, E2b-]-CEA. Note the significantly elevated response in splenocytes from the Ad5 [E1-, E2b]-CEA immunized group. Values represent mean±SEM.

CMI responses were assessed by ELISpot assays performed on splenocytes exposed to intact CEA antigen. Splenocytes from Ad5 immune C57Bl/6 mice that were immunized subcutaneously with Ad5 E1-]-CEA or Ad5 [E1-, E2b-]-CEA were harvested and assessed for the number of IFN-γ and IL-2 secreting cells as described above. As shown in FIGS. 16A and 16B, significantly elevated numbers of both IFN-γ and IL-2 secreting cells were observed in spleens assayed from mice immunized with Ad5 [E1-, E2b-]-CEA as compared to immunized Ad5 [E1-]-CEA mice. Specificity studies revealed that immunizations with Ad5 CEA vectors induced specific CEA associated CMI responses and not responses against other irrelevant antigens such as the HIV-gag protein or β-galactosidase. These results demonstrate that immunization of Ad5 immune mice with Ad5 [E1-, E2b-]-CEA induce significantly higher CMI responses.

Lack of Adverse Liver Effects in Immunized Mice

Figure 17:
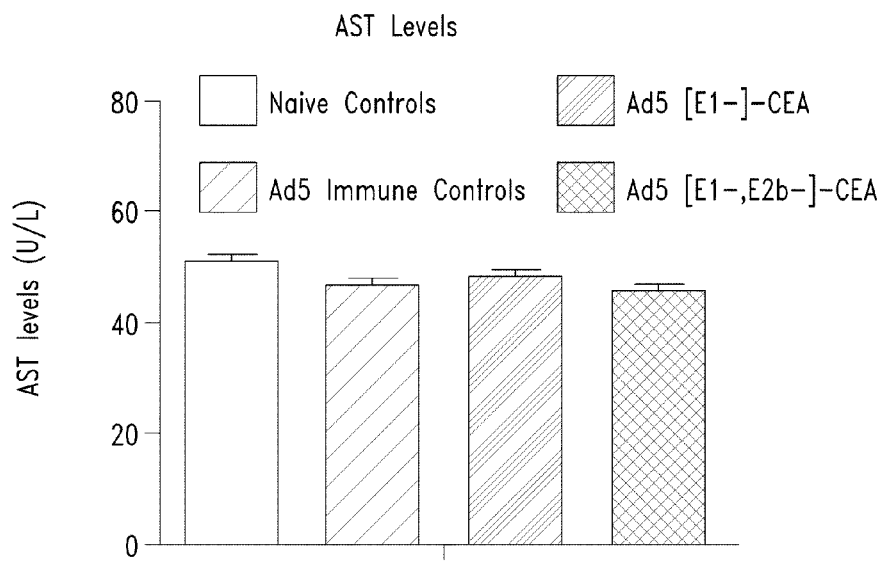
FIG. 17 is a bar graph showing serum AST levels in control mice and mice vaccinated with $10^{10}$ viral particles of Ad5 [E1-]-CEA or Ad5 [E1-, E2b-]-CEA. Values represent mean±SEM.

Toxicity studies were performed on serum from Ad5 immune female C57Bl/6 mice immunized with Ad5 [E1-]-CEA, Ad5 [E1-, E2b-]-CEA as described above. Ad5 naïve or Ad5 immune mice injected with buffer alone served as controls. Three days after the third immunization, aspartate aminotransferase (AST) levels were assessed on the blood samples to determine liver toxicity due to the treatment. AST levels were not elevated over controls following immunization with either vector (FIG. 17). Alanine aminotransferase (ALT) levels were also assessed and similar results were observed.

Ad5 [E1-, E2b-]-CEA Immunotherapy in Ad5 Immune Tumor Bearing Mice

Based upon the successful immunological results observed above, studies in which MC38 tumors were established in mice and then treated were performed as described below. For these studies a CEA expressing MC38 murine cell line was used. This cell line has been genetically modified to express human CEA and can be implanted into C57Bl/6 mice. After tumor establishment, the mice were treated with the novel Ad5 [E1-, E2b-]-CEA vector platform. To determine if Ad5 immune tumor bearing mice could be treated with the Ad5 [E1-, E2b-]-CEA vector, C57Bl/6 mice were injected two times subcutaneously with $10^{10}$ Ad5 [E1-]-null VP at 14 day intervals to render the mice Ad5 immune. Two weeks after the last injection, two groups of 7 C57Bl/6 mice were injected subcutaneously with $10^6$ CEA expressing MC38 tumor cells. Seven days later, when tumors were palpable, one group of mice was treated by distal subcutaneous injection with $10^{10}$ VP of Ad5 [E1-, E2b-]-CEA on days 7, 13 and 19. A group of 7 injection buffer only treated C57Bl/6 mice served as untreated controls. All mice were monitored for tumor size over a 21 day period and tumor volumes were determined as previously described.

Figure 18:
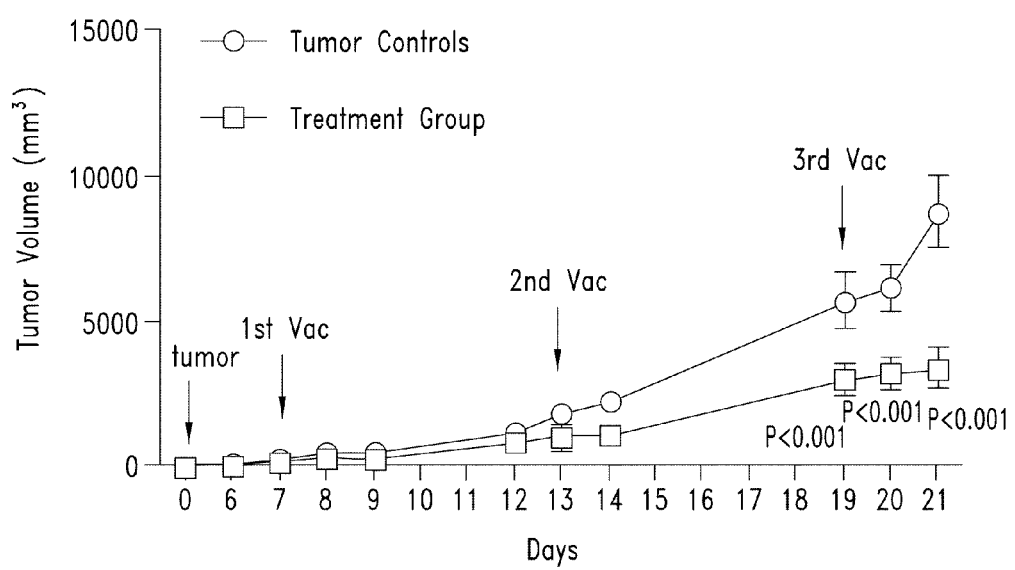
FIG. 18 is a line graph showing tumor volume. Ad5 immune C57BI/6 mice were injected with MC38 CEA expressing tumor cells and subsequently treated (Vac) with Ad5 [E1-, E2b-]-CEA vaccine as described. Note the significant reduction in tumor size by days 19-21 as compared to untreated control tumor bearing mice. Tumor measurements were taken and volumes were determined. Statistical analysis was performed using the Bonferroni post-tests analysis with PRISM software. Values represent mean±SEM.
Figure 19:
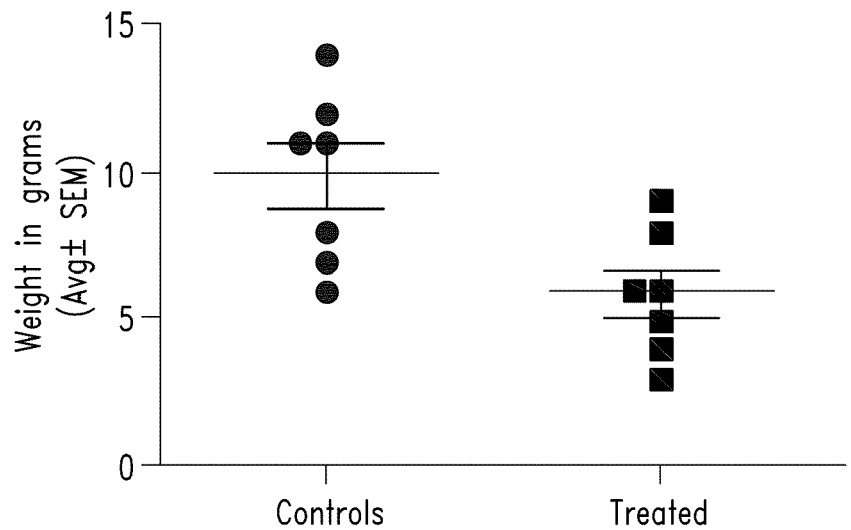
FIG. 19 is a graph showing tumor weights from treated and untreated Ad5 immune MC38 tumor bearing mice. Note the significant ($p=0.0124$) reduction in tumor weights from the mice treated with Ad5 [E1-, E2b-]-CEA. Values represent mean±SEM.

As shown in FIG. 18, the tumor growth by day 19 was significantly reduced in the Ad5 [E1-, E2b-]-CEA treated mice and remained so. At the end of the study (Day 22), the mice were sacrificed and the tumors were excised and weighed. As shown in FIG. 19, the tumors in the mice treated with Ad5 [E1-, E2b-]-CEA were significantly (P<0.05) smaller in weight than the untreated controls.

At the termination of the study, spleens were collected from mice and the CEA specific CMI response was determined by ELISpot assay. CEA specific IFN-γ secretion response was significantly higher in mice immunized with Ad5 [E1-, E2b-]-CEA than in mice who received MC-38 tumor cells alone. These results indicate that treatment of CEA expressing tumors in Ad5 immunized mice using the Ad5 [E1-, E2b-]-CEA vaccine can significantly decrease tumor growth progression.

Example 7

Immunizations with an Ad5 [E1-, E2b-] Vector Vaccine in Non-Human Primates with Pre-Existing Ad5 Immunity This example shows that multiple immunizations with an Ad5 [E1-, E2b-] vector vaccine in non-human primates (NHP) with pre-existing Ad5 immunity is effective.

An Ad5 [E1-, E2b-]-Simian immunodeficiency virus (SIV)-gag vector was constructed by recombination in BJ5183 bacterial cells and rescued by transfection into pre-terminal protein (pTP) and polymerase (pol) expressing E.C7 cells. The Ad5 [E1-, E2b-] vector contains deletions in both the pol and pTP genes, since this arrangement has been demonstrated to result in decreased liver toxicity when compared to Ad5 [E1-] virus. The mini-gene cassette expressing the particular antigen is subcloned into the E1 region of a shuttle vector and recombined with E2b deleted (pol-, pTP-) Ad5 genomic DNA. The SIV gag gene was constructed from Simian (macaque) immunodeficiency virus, isolate 239 genome (GenBank Accession # M33262.1). The SIV gag (951-1074) containing plasmid was synthesized by GeneArt (Regensburg, Germany). The recombined Ad5 [E1-, E2b-] vector was verified by restriction analysis and rescued as virus particles by restriction enzyme release and transfection into E.C7 cells. The Ad5 [E1-, E2b-] viral vector was manufactured by releasing from E.C7 producer cells by Triton X-100, precipitated in PEG, purified on CsCl gradients, dialyzed against 20 mM HEPES (pH 7.4) containing 5% sucrose, aliquoted, and frozen in a dry ice-ethanol bath. Particle concentration is calculated both by absorption at 260 and 280 nm (normal ratio=1.3) and by real-time PCR analysis. The former value is used to determine amounts of virus for in vivo experiments. The Ad5 [E1-, E2b-] vectors are further tested for antigen expression in infected cells. This is accomplished by transfection of A549 human lung carcinoma cells in vitro and subsequent analysis of isolated protein by Western blot assay for the detection of expressed antigen in transfected cells.

A total of 18 animals were used in the study. Seven NHP were immunized two times at two weeks intervals with $1 \times 10^{10}$ viral particles (VP) of Ad5-null (empty) to render the animals Ad5 immune prior to immunization with the vaccine (Group 1). Seven NHP were not immunized with Ad5-null to serve as naïve Ad5 [E1-, E2b-]-SIV-gag immunized controls (Group 2). Four NHP were immunized two times at two weeks intervals with $1 \times 10^{10}$ viral particles (VP) of Ad5-null (empty) to render the animals Ad5 immune and served as Ad5 immune non-Ad5 [E1-, E2b-]-SIV-gag immunized controls (Group 3). Prior to initiation of immunizations, the NHP were tested for the presence of Ad NAb. As shown in Table 1, all NHP pre-immunized with Ad5-null exhibited Ad5 neutralizing activity (NAb) with endpoint titers of 1/100 to 1/200. NHP that were not immunized with Ad5-Null had NAb endpoint titers 1/10 or less.

TABLE 1

| NHP | Endpoint NAb |
|---|---|
| Group 1-NHP-1 | 1/200 |
| Group 1-NHP-2 | 1/200 |
| Group 1-NHP-3 | 1/200 |

TABLE 1-continued

| NHP | Endpoint NAb |
|---|---|
| Group 1-NHP-4 | 1/200 |
| Group 1-NHP-5 | 1/200 |
| Group 1-NHP-6 | 1/100 |
| Group 1-NHP-7 | 1/200 |
| Group 2-NHP-1 | 1/10 |
| Group 2-NHP-2 | <1/10 |
| Group 2-NHP-3 | <1/10 |
| Group 2-NHP-4 | <1/10 |
| Group 2-NHP-5 | <1/10 |
| Group 2-NHP-6 | <1/10 |
| Group 2-NHP-7 | <1/10 |
| Group 3-NHP-1 | 1/200 |
| Group 3-NHP-2 | 1/200 |
| Group 3-NHP-3 | 1/200 |
| Group 3-NHP-4 | 1/100 |

Figure 20:
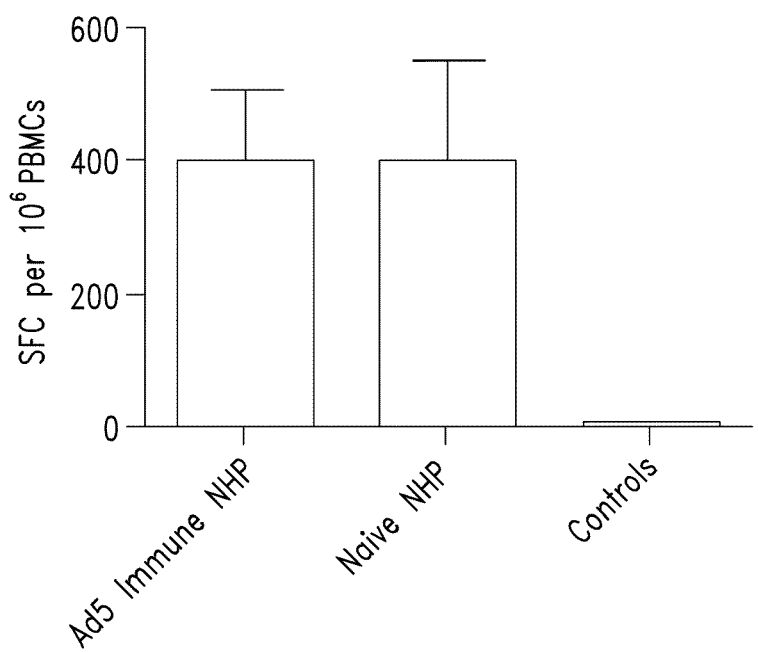
FIG. 20 is a bar graph showing INF-γ secreting splenocytes from non-human primates (NHP). Groups of NHP were immunized twice at 2 week intervals with Ad5 [E1-, E2b-]-SIV-gag. After immunizations, PBMCs were assessed for IFN-γ secreting lymphocytes (SFC). Significantly elevated numbers of IFN-γ secreting lymphocytes were observed after immunizations and these levels were similar in the Ad5 immune and naïve groups. Values represent the mean±SEM.

All the NHP in Groups 1 and 2 were then immunized subcutaneously two times at two week intervals with $1 \times 10^{10}$ VP Ad5 [E1-, E2b-]-SIV-gag. Two weeks after the second immunization with vaccine, PBMCs were isolated from each animal and numbers of IFN-γ secreting lymphocytes were assessed by ELISpot assay. As shown in FIG. 20, significantly (P<0.05) elevated numbers of IFN-γ secreting lymphocytes were detected in immunized NHP as compared with non-immunized Ad5 immune control NHP (Group 3). Moreover, the levels of IFN-γ secreting lymphocytes observed immunized Ad5 immune NHP were not significantly different from the levels of IFN-γ lymphocytes observed in non-Ad5 immune NHP. These results indicate that high levels of CMI responses can be achieved in NHP despite the presence of pre-existing immunity to Ad5 and these levels are comparable to those observed in naïve animals.

Example 8

A Modified E6 Cancer Vaccine Vector Based on the Ad5 [E1-, E2b-] Platform

This example illustrates how multiple immunizations of Ad5 immune mice with Ad5 [E1-, E2b-]-E6E7 could induce HPV E6E7 specific CMI and antibody responses that have beneficial effects on tumorigenesis.

Production and Characterization of Ad5 [E1-, E2b-]-E6E7 Vector

The early gene 6 (E6) of the human papilloma virus (HPV) encodes an oncoprotein involved in the tumorigenesis of HPV. The E6 protein contributes to tumorigenesis by binding to p53 in human cells. This leads to a downregulation of p53 target genes that, in turn, leads to faulty DNA replication and accumulation of mutations.

The early gene 7 (E7) of HPV encodes an oncoprotein involved in the tumorigenesis of HPV. The E7 protein contributes to tumorigenesis by binding to retinoblastoma protein (pRb) in human cells. This ultimately leads to a disruption in the cell cycle causing uncontrolled cellular proliferation.

The HPV E6 and E7 polynucleotide sequences utilized for these studies are modified so that the encoded polypeptide remains antigenic but is no longer oncogenic. For example, the modified E6 peptide may no longer be able to interact with p53 (e.g., deletion of the p53 binding site) but is capable of generating an immune response against the unmodified E6 protein. For transgene construction in these studies, the p53 binding site of the constructed gene will be eliminated. The p53 binding site may be eliminated by mutating or deleting a portion of the E6 protein. Similarly, the modified E7 peptide will no longer be able to interact with pRb (e.g., deletion of the pRb binding site), but will be capable of generating an immune response against the unmodified E7 protein. Therefore, the pRb binding site will be eliminated for transgene construction. The pRb binding site may be eliminated by mutating or deleting a portion of the E7 protein.

The modified E6 and E7 constructs could each be used separately for vaccines; however, the study described herein uses a construct encoding both E6 and E7, to be expressed either as separate polypeptides or as a fusion polypeptide.

Initial studies are performed to confirm gene expression of the Ad5 [E1-, E2b-]-E6E7 vector platform. To determine that E6E7 is expressed by cells transfected with the vaccine vector platform, A549 cells available from ATCC are transfected with Ad5 [E1-, E2b-]-E6E7. Western blot analysis is used to determine if cells transfected with the vector platform express E6E7. Briefly, $10^6$ human lung carcinoma cells (A-549) (ATCC number CCL-185) are infected at a multiplicity of infection (MOI) of 900 or 150 VP, incubated for 24 hours and then lysed. Cell lysates are separated on a 10% SDS-polyacrylamide gel and transferred onto a PVDF membrane (GE Healthcare, Piscataway, N.J.). The membranes are then blocked with TBS containing 5% (w/v) blocking reagent (GE Healthcare, Piscataway, N.J.) for 2 hours at room temperature and sequentially incubated with mouse anti-HER2 antibody (1:250) (Genway, San Diego, Calif.) and goat anti-mouse-HRP conjugated antibody (1:1000) (Kirkegaard & Perry Laboratories, Gaithersburg, Md.) for one hour at room temperature. Reactivity is determined by chemiluminescence using an ECL Western Blotting analysis system (GE Healthcare, Piscataway, N.J.) according to the manufacturer's specifications. It is expected that E6E7 protein bands will be observed after development.

Escalating Dose Trial of Ad5 [E1-, E2b-]-E6E7 Vaccine:

A study is performed to determine the effect of immunizations with various doses of Ad5 [E1-, E2b-]-E6E7 on the induction of CMI responses in mice. Groups of naïve female BALB/c mice, 4 to 8 weeks old, are immunized three times at weekly intervals with $10^8$, $10^9$, or $10^{10}$ VP of Ad5 [E1-, E2b-]-E6E7. Control mice are injected with buffer solution only. Two weeks after the last immunization, the mice are euthanized and CMI responses assessed. A dose response effect is expected to be observed with the highest CMI response levels observed after immunizations with $10^{10}$ viral particles (VP) of Ad5 [E1-, E2b-]-E6E7.

Induction of Ad5 Immunity in Mice as Evidenced by Levels of Ad5 Neutralizing Antibody To induce Ad5 immunity, Ad5 naïve mice are injected intradermally twice at two week intervals with $10^{10}$ virus particles of Ad5-null (empty). Two weeks later, serum samples are collected and assessed for endpoint Ad5 neutralizing antibody (NAb) titers. As described above and shown in FIG. 9, this protocol induces NAb activity in mice. Therefore, mice will be made Ad5 immune by two injections with Ad5-null.

Immunization of Ad5 Immune Mice with Ad5 [E1-, E2b-]-E6E7

Experiments are performed to assess immune responses in Ad5 immune mice using multiple immunizations with Ad5 vector based vaccines. Two weeks following the last Ad5-null (empty vector) immunization, groups of female BALB/c mice, 4 to 8 weeks old, are immunized one, two or three times at weekly intervals with $10^{10}$ virus particles of Ad5 [E1-, E2b-]-E6E7. Thus, before mice are immunized with Ad5 [E1-, E2b-]-E6E7, they will have measurable pre-existing Ad5 NAb endpoint titers. Two weeks following the last immunization with Ad5 [E1-, E2b-]-E6E7, mice are euthanized and their spleens harvested for analysis of CMI and antibody responses over the course of one, two, and three immunizations with Ad5 [E1-, E2b-]-E6E7.

Induction of CMI Responses

CMI responses will be assessed by ELISpot assays performed on splenocytes exposed to E6 and E7 peptides. Splenocytes from Ad5 immune mice that were immunized with Ad5 [E1-, E2b-]-E6E7 are harvested and assessed for the number of IFN-γ and IL-2 secreting splenocytes. An elevation in numbers of IFN-γ and IL-2 secreting cells in spleens assayed from mice after immunizations with Ad5 [E1-, E2b-]-E6E7 indicates an E6E7-specific CMI response.

Specificity studies can be used to confirm that immunizations induced specific E6 and E7 associated CMI responses and not responses against other irrelevant antigens. These assays can demonstrate that multiple immunizations of Ad5 immune mice with Ad5 [E1-, E2b-]-E6E7 induces E6 and E7 specific CMI responses.

Induction of Humoral Responses

Studies are also performed to determine if anti-E6 and anti-E7 IgG antibodies are induced after immunizations. For example, an ELISA for circulating IgG antibody to E6 and E7 can be performed. Increasing quantities of detectable antibody to E6 and E7 observed after one, two, or three immunizations with Ad5 [E1-, E2b-]-E6E7 indicate that in addition to CMI responses, antibody responses directed toward the E6 and E7 proteins are also induced in Ad5 immune mice immunized with Ad5 [E1-, E2b-]-E6E7.

Detection of Adverse Liver Effects in Immunized Mice

Toxicity studies are performed on serum from Ad5 immune mice immunized with Ad5 [E1-, E2b-]-E6E7 as described above. Ad5 immune mice injected with buffer alone serve as controls. Three days after the third immunization, aspartate aminotransferase (AST) and alanine aminotransferase (ALT) levels are assessed in the blood samples to determine if any liver toxicity due to the immunizations is present. If AST and ALT levels are not elevated over controls following immunization with the Ad5 vector, it indicates that mice can be safely immunized with Ad5 [E1-, E2b-]-E6E7 to induce specific humoral and CMI responses against E6 and E7.

Tumor Challenge of Ad5 [E1-, E2b-]-E6E7 Immunized Ad5 Immune Mice

Studies are performed to determine if Ad5 immune mice immunized with the Ad5 [E1-, E2b-]-E6E7 vector platform can resist a challenge of implanted tumor cells expressing E6 and/or E7.

Groups of 7 mice each are injected two times at two week intervals with Ad5-null to render the mice Ad5 immune. Two weeks after the last Ad5-null injection, the mice are injected three times at weekly intervals with injection buffer (Tumor Controls), immunized with Ad5-null (No Transgene, vector control group) (Vector Controls), or with Ad5 [E1-, E2b-]-E6E7 (Immunized Group). Two weeks following the last immunization (or injection), the mice are implanted subcutaneously with $1 \times 10^6$ E6E7 expressing murine tumor cells. After implantation, tumor progression is monitored. The tumors are measured and the volumes calculated. If mice immunized with Ad5 [E1-, E2b-]-E6E7 resist a challenge with E6E7 expressing tumor in comparison with mice receiving injections of buffer only or Ad5-null, it indicates that Ad5 immune mice immunized with Ad5 [E1-, E2b-]-E6E7 can slow the progress of tumor growth after a lethal challenge of E6E7 expressing tumor cells. It is expected that tumor progression will occur in the tumor control and Ad5-null vector control groups. In contrast, little or no tumor growth or progression is expected to be observed in the Ad5 [E1-, E2b-]-E6E7 treated group.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of generating an immune response against one or more target antigens in an individual comprising:
   (a) administering to the individual a first vector comprising: i) a replication defective adenovirus vector, wherein said adenovirus vector has a deletion in the E2b region, and ii) a nucleic acid encoding a first target antigen;
   (b) subsequently administering to the individual a second vector comprising: i) the replication defective adenovirus vector of step (a), and ii) a nucleic acid encoding a second target antigen, wherein the second target antigen of the second vector is the same or different from the first target antigen of the first vector;
   thereby generating an immune response against the first target antigen and the second target antigen.

2. The method of claim 1, wherein the first and second vectors are not gutted vectors.

3. The method of claim 1, wherein the individual has pre-existing immunity to an adenovirus.

4. The method of claim 1, wherein the first and second target antigens of the first and the second vectors are derived from the same infectious organism.

5. The method of claim 1, wherein the first and second target antigens of the first and the second vectors are derived from different infectious organisms.

6. The method of claim 1, wherein the first target antigen of the first vector comprises an HIV protein, or a variant or fragment thereof.

7. The method of claim 6, wherein the second target antigen of the second vector comprises an E. coli β-galactosidase.

8. The method of claim 6, wherein the HIV protein is an HIV-gag protein.

9. The method of claim 1, wherein the first target antigen of the first vector comprises an HIV protein, or a variant or fragment thereof, and the second target antigen of the second adenovirus vector comprises an HIV protein, or a variant or fragment thereof.

10. The method of claim 9, wherein the first target antigen of the first vector comprises an HIV protein, or a variant or fragment thereof, and the second target antigen of the second adenovirus vector comprises an HIV protein, or a variant or fragment thereof, that is different from the HIV protein of the first adenovirus vector.

11. The method of claim 1, wherein the first target antigen of the first vector comprises a cancer protein, or a variant or fragment thereof.

12. The method of claim 11, wherein the first target antigen of the first vector comprises a Her2/neu antigen, or a variant or fragment thereof.

13. The method of claim 11, wherein the first target antigen of the first vector comprises a carcinoembryonic protein, or a variant or fragment thereof.

14. The method of claim 1, wherein the first target antigen of the first vector comprises a human papillomavirus protein, or a variant or fragment thereof.

15. The method of claim 14, wherein the human papillomavirus protein is viral protein E6.

16. The method of claim 14, wherein the human papillomavirus protein is viral protein E7.

17. The method of claim 1, wherein the first target antigen of the first vector comprises an antigen selected from the group consisting of: a bacterial antigen, a viral antigen, an antigen derived from a protozoan protein, an antigen derived from a fungal protein, an antigen derived from a mold protein, an antigen derived from a mammalian protein, and an antigen derived from an avian protein, or a variant or fragment thereof.

18. The method of claim 1, wherein the first target antigen of the first vector comprises an antigen derived from a virus selected from the group consisting of: a Venezuelan Equine Encephalitis Virus (VEEV), a Western Equine Encephalitis Virus, and a Japanese Encephalitis Virus, or a variant or fragment thereof.

19. The method of claim 1, wherein the first target antigen of the first vector comprises a Leishmania protein.

20. The method of claim 1, wherein the first target antigen of the first vector comprises a cancer protein selected from the group consisting of:
carcinoembryonic antigen, Her2/Neu, a human papilloma virus protein and WT-1, or a variant or fragment thereof.

21. The method of claim 20, wherein the variant or fragment is not oncogenic or has reduced oncogenicity compared to the wild type cancer protein.

22. The method of claim 1, wherein the first target antigen of the first vector comprises an influenza virus protein, or a fragment or variant thereof.

23. The method of claim 22, wherein the influenza virus protein is derived from an influenza virus selected from the group consisting of: H5N1, H3N2, H9N1, H1N1, H2N2, H7N7, H1N2, H9N2, H7N2, H7N3, and H10N7.

24. The method of claim 22, wherein the influenza virus protein is selected from the group consisting of: haemagglutinin, neuraminidase, and matrix protein M1.

25. The method of claim 1, wherein the first vector is not a gutted vector.

26. The method of claim 1, wherein the second vector is not a gutted vector.

* * * * *